(12) United States Patent
Michelson

(10) Patent No.: US 8,480,717 B2
(45) Date of Patent: *Jul. 9, 2013

(54) ORTHOPEDIC IMPLANT WITH LOCKING ELEMENT

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,281

(22) Filed: Sep. 11, 2012

(65) Prior Publication Data

US 2013/0013002 A1    Jan. 10, 2013

Related U.S. Application Data

(60) Continuation of application No. 13/406,178, filed on Feb. 27, 2012, now Pat. No. 8,262,708, which is a continuation of application No. 10/938,380, filed on Sep. 11, 2004, now Pat. No. 8,123,788, which is a continuation of application No. 10/802,906, filed on Mar. 17, 2004, now Pat. No. 8,048,075, which is a continuation of application No. 10/098,991, filed on Mar. 15, 2002, now Pat. No. 7,077,844, which is a division of application No. 09/669,912, filed on Sep. 26, 2000, now Pat. No. 6,383,186, which is a division of application No. 09/022,344, filed on Feb. 11, 1998, now Pat. No. 6,139,550.

(60) Provisional application No. 60/037,139, filed on Feb. 11, 1997.

(51) Int. Cl.
*A61B 17/80* (2006.01)
*A61B 17/66* (2006.01)

(52) U.S. Cl.
USPC .......................................... 606/289; 606/280

(58) Field of Classification Search
USPC .................................................. 606/280, 289
See application file for complete search history.

(56) References Cited

U.S. PATENT DOCUMENTS

| 74,489 | A | 2/1868 | Bidwell |
| 824,867 | A | 7/1906 | Houghton |
| 1,105,105 | A | 7/1914 | Sherman |
| 2,423,511 | A | 7/1947 | Luben et al. |
| 2,460,613 | A | 2/1949 | Whelan et al. |
| 2,526,959 | A | 10/1950 | Lorenzo |
| 2,550,867 | A | 5/1951 | Rosan |
| 2,757,457 | A | 8/1956 | Ziegelski, Sr. |

(Continued)

FOREIGN PATENT DOCUMENTS

| CA | 2 154 470 A1 | 8/1994 |
| CA | 2 144 353 A1 | 11/1995 |

(Continued)

OTHER PUBLICATIONS

Provisional U.S. Appl. No. 60/008,365 to Bray, filed Dec. 8, 1995, 27 pages.

(Continued)

*Primary Examiner* — Kevin T Truong
*Assistant Examiner* — David Bates
(74) *Attorney, Agent, or Firm* — Martin & Ferraro, LLP

(57) ABSTRACT

An orthopedic implant with a locking element for locking a bone screw in a bone screw receiving hole of the implant.

15 Claims, 30 Drawing Sheets

U.S. PATENT DOCUMENTS

| | | | |
|---|---|---|---|
| 2,825,329 A | 3/1958 | Caesar | |
| 3,244,170 A | 4/1966 | McElvenny | |
| 3,386,437 A | 6/1968 | Treace | |
| 3,604,414 A | 9/1971 | Borges | |
| 3,709,219 A | 1/1973 | Halloran | |
| 3,741,205 A | 6/1973 | Markolf | |
| 3,750,652 A | 8/1973 | Sherwin | |
| 3,840,014 A | 10/1974 | Ling et al. | |
| 3,842,825 A | 10/1974 | Wagner | |
| 3,866,523 A | 2/1975 | Geschwender | |
| 3,960,147 A | 6/1976 | Murray | |
| 4,047,524 A | 9/1977 | Hall | |
| 4,069,586 A | 1/1978 | Skelton | |
| 4,081,309 A | 3/1978 | Jenkins | |
| 4,102,339 A | 7/1978 | Weber et al. | |
| 4,164,794 A | 8/1979 | Spector et al. | |
| 4,219,015 A | 8/1980 | Steinemann | |
| 4,338,926 A | 7/1982 | Kummer et al. | |
| 4,388,921 A | 6/1983 | Sutter et al. | |
| RE31,628 E | 7/1984 | Allgower et al. | |
| 4,484,570 A | 11/1984 | Sutter et al. | |
| 4,488,543 A | 12/1984 | Tornier | |
| 4,493,317 A | 1/1985 | Klaue | |
| 4,503,848 A | 3/1985 | Caspar et al. | |
| 4,542,539 A | 9/1985 | Rowe, Jr. et al. | |
| 4,563,489 A | 1/1986 | Urist | |
| 4,573,458 A | 3/1986 | Lower | |
| 4,596,574 A | 6/1986 | Urist | |
| 4,599,086 A | 7/1986 | Doty | |
| 4,628,923 A | 12/1986 | Medoff | |
| 4,651,724 A | 3/1987 | Berentey et al. | |
| 4,683,108 A | 7/1987 | Balog | |
| 4,733,657 A | 3/1988 | Kluger | |
| 4,743,256 A | 5/1988 | Brantigan | |
| 4,781,183 A | 11/1988 | Casey et al. | |
| 4,794,918 A | 1/1989 | Wolter | |
| 4,838,252 A | 6/1989 | Klaue | |
| 4,863,475 A | 9/1989 | Andersen et al. | |
| 4,896,661 A | 1/1990 | Bogert et al. | |
| 4,898,161 A | 2/1990 | Grundei | |
| 4,903,691 A | 2/1990 | Heinl | |
| 4,917,704 A | 4/1990 | Frey et al. | |
| 4,923,471 A | 5/1990 | Morgan | |
| 4,929,247 A | 5/1990 | Rayhack | |
| 4,950,270 A | 8/1990 | Bowman et al. | |
| 4,955,908 A | 9/1990 | Frey et al. | |
| 4,957,495 A | 9/1990 | Kluger | |
| 4,957,496 A | 9/1990 | Schmidt | |
| 4,959,065 A | 9/1990 | Arnett et al. | |
| 4,961,740 A | 10/1990 | Ray et al. | |
| 5,000,166 A | 3/1991 | Karpf | |
| 5,013,313 A | 5/1991 | Surer | |
| 5,019,079 A | 5/1991 | Ross | |
| 5,041,113 A | 8/1991 | Biedermann et al. | |
| 5,041,116 A | 8/1991 | Wilson | |
| 5,052,373 A | 10/1991 | Michelson | |
| 5,053,036 A | 10/1991 | Perren et al. | |
| 5,057,111 A | 10/1991 | Park | |
| 5,059,194 A | 10/1991 | Michelson | |
| 5,071,437 A | 12/1991 | Steffee | |
| 5,084,051 A | 1/1992 | Tormala et al. | |
| 5,085,660 A | 2/1992 | Lin | |
| 5,108,395 A | 4/1992 | Laurain | |
| 5,108,399 A | 4/1992 | Eitenmuller et al. | |
| 5,127,912 A | 7/1992 | Ray et al. | |
| 5,127,914 A | 7/1992 | Calderale et al. | |
| 5,129,899 A | 7/1992 | Small et al. | |
| 5,147,361 A | 9/1992 | Ojima et al. | |
| 5,151,103 A | 9/1992 | Tepic et al. | |
| 5,167,662 A | 12/1992 | Hayes et al. | |
| 5,180,381 A | 1/1993 | Aust et al. | |
| 5,190,544 A | 3/1993 | Chapman et al. | |
| 5,209,751 A | 5/1993 | Farris et al. | |
| 5,211,664 A | 5/1993 | Tepic et al. | |
| 5,217,497 A | 6/1993 | Mehdian | |
| 5,234,430 A | 8/1993 | Huebner | |
| 5,234,431 A | 8/1993 | Keller | |
| 5,250,048 A | 10/1993 | Gundolf | |
| 5,261,910 A | 11/1993 | Warden et al. | |
| 5,275,601 A | 1/1994 | Gogolewski et al. | |
| 5,290,288 A | 3/1994 | Vignaud et al. | |
| 5,300,073 A | 4/1994 | Ray et al. | |
| 5,300,074 A | 4/1994 | Frigg | |
| 5,306,307 A | 4/1994 | Senter et al. | |
| 5,318,567 A | 6/1994 | Vichard | |
| 5,324,290 A | 6/1994 | Zdeblick et al. | |
| 5,338,197 A | 8/1994 | Kwan | |
| 5,344,421 A | 9/1994 | Crook | |
| 5,348,026 A | 9/1994 | Davidson | |
| 5,364,399 A | 11/1994 | Lowery et al. | |
| 5,380,324 A | 1/1995 | Muller et al. | |
| 5,380,327 A | 1/1995 | Eggers et al. | |
| 5,380,328 A | 1/1995 | Morgan | |
| 5,395,371 A | 3/1995 | Miller et al. | |
| 5,397,363 A | 3/1995 | Gelbard | |
| 5,405,391 A | 4/1995 | Hednerson et al. | |
| 5,417,533 A | 5/1995 | Lasner | |
| 5,423,826 A | 6/1995 | Coates et al. | |
| 5,429,639 A | 7/1995 | Judet | |
| 5,443,467 A | 8/1995 | Biedermann et al. | |
| 5,456,685 A | 10/1995 | Huebner | |
| 5,458,653 A | 10/1995 | Davidson | |
| 5,468,242 A | 11/1995 | Reisberg | |
| 5,478,340 A | 12/1995 | Kluger | |
| 5,478,348 A | 12/1995 | Bajada | |
| 5,484,440 A | 1/1996 | Allard | |
| 5,487,741 A | 1/1996 | Maruyama et al. | |
| 5,487,743 A | 1/1996 | Laurain et al. | |
| 5,492,442 A | 2/1996 | Lasner | |
| 5,520,687 A | 5/1996 | Howland | |
| 5,520,690 A | 5/1996 | Errico et al. | |
| 5,527,310 A | 6/1996 | Cole et al. | |
| 5,527,311 A | 6/1996 | Procter et al. | |
| 5,527,314 A | 6/1996 | Brumfield et al. | |
| 5,531,554 A | 7/1996 | Jeanson et al. | |
| 5,531,746 A | 7/1996 | Errico et al. | |
| 5,534,027 A | 7/1996 | Hodorek | |
| 5,545,163 A | 8/1996 | Miller et al. | |
| 5,545,164 A | 8/1996 | Howland | |
| 5,545,165 A | 8/1996 | Biedermann et al. | |
| 5,545,166 A | 8/1996 | Howland | |
| 5,549,612 A * | 8/1996 | Yapp et al. | 606/293 |
| 5,558,674 A | 9/1996 | Heggeness et al. | |
| 5,562,663 A | 10/1996 | Wisnewski et al. | |
| 5,562,672 A | 10/1996 | Huebner et al. | |
| 5,569,251 A | 10/1996 | Baker | |
| 5,578,034 A | 11/1996 | Estes | |
| 5,582,612 A | 12/1996 | Lin | |
| 5,593,409 A | 1/1997 | Michelson | |
| 5,601,553 A | 2/1997 | Trebing et al. | |
| 5,607,426 A | 3/1997 | Ralph et al. | |
| 5,616,142 A | 4/1997 | Yuan et al. | |
| 5,616,144 A | 4/1997 | Yapp et al. | |
| 5,620,443 A | 4/1997 | Gertzbein et al. | |
| 5,643,265 A | 7/1997 | Errico et al. | |
| 5,662,652 A | 9/1997 | Schafer et al. | |
| 5,662,655 A | 9/1997 | Laboureau et al. | |
| 5,672,175 A | 9/1997 | Martin | |
| 5,676,666 A * | 10/1997 | Oxland et al. | 606/86 B |
| 5,676,703 A | 10/1997 | Gelbard | |
| 5,681,311 A | 10/1997 | Foley et al. | |
| 5,702,396 A | 12/1997 | Hoenig et al. | |
| 5,718,705 A | 2/1998 | Sammarco | |
| 5,725,588 A | 3/1998 | Errico et al. | |
| 5,733,287 A | 3/1998 | Tepic et al. | |
| 5,735,853 A | 4/1998 | Olerud | |
| 5,735,899 A | 4/1998 | Schwartz et al. | |
| 5,755,796 A | 5/1998 | Ibo et al. | |
| 5,766,254 A | 6/1998 | Gelbard | |
| 5,772,437 A | 6/1998 | Rangert et al. | |
| 5,772,661 A | 6/1998 | Michelson | |
| 5,776,199 A | 7/1998 | Michelson | |
| 5,782,830 A | 7/1998 | Farris | |
| 5,797,914 A | 8/1998 | Leibinger | |
| D402,032 S | 12/1998 | Stone | |
| 5,849,012 A | 12/1998 | Abboudi | |
| 5,860,973 A | 1/1999 | Michelson | |

| | | | |
|---|---|---|---|
| 5,868,749 A | 2/1999 | Reed | |
| D406,646 S | 3/1999 | Stone | |
| 5,876,402 A | 3/1999 | Errico et al. | |
| 5,876,446 A | 3/1999 | Agrawal et al. | |
| 5,879,389 A | 3/1999 | Koshino | |
| 5,888,223 A | 3/1999 | Bray, Jr. | |
| 5,899,904 A | 5/1999 | Errico et al. | |
| 5,931,838 A | 8/1999 | Vito | |
| 5,954,722 A | 9/1999 | Bono | |
| 5,984,967 A | 11/1999 | Zdeblick et al. | |
| 6,022,350 A * | 2/2000 | Ganem | 606/272 |
| 6,030,389 A | 2/2000 | Wagner et al. | |
| 6,102,951 A | 8/2000 | Sutter et al. | |
| 6,123,709 A | 9/2000 | Jones | |
| 6,139,550 A | 10/2000 | Michelson | |
| 6,152,927 A | 11/2000 | Farris et al. | |
| 6,193,719 B1 | 2/2001 | Gournay et al. | |
| 6,193,721 B1 | 2/2001 | Michelson | |
| 6,235,034 B1 | 5/2001 | Bray | |
| 6,342,055 B1 | 1/2002 | Eisermann et al. | |
| 6,364,880 B1 | 4/2002 | Michelson | |
| 6,383,186 B1 | 5/2002 | Michelson | |
| 6,398,783 B1 | 6/2002 | Michelson | |
| 6,416,528 B1 | 7/2002 | Michelson | |
| 6,428,542 B1 | 8/2002 | Michelson | |
| 6,454,771 B1 | 9/2002 | Michelson | |
| 6,527,776 B1 | 3/2003 | Michelson | |
| 6,592,586 B1 | 7/2003 | Michelson | |
| 6,610,099 B1 | 8/2003 | Albrektsson et al. | |
| 6,616,666 B1 | 9/2003 | Michelson | |
| 6,620,163 B1 | 9/2003 | Michelson | |
| 6,712,818 B1 | 3/2004 | Michelson | |
| 6,916,320 B2 | 7/2005 | Michelson | |
| 6,923,810 B1 | 8/2005 | Michelson | |
| 6,926,718 B1 | 8/2005 | Michelson | |
| 6,936,050 B2 | 8/2005 | Michelson | |
| 6,936,051 B2 | 8/2005 | Michelson | |
| 6,969,390 B2 | 11/2005 | Michelson | |
| 7,041,105 B2 | 5/2006 | Michelson | |
| 7,044,952 B2 | 5/2006 | Michelson | |
| 7,074,221 B2 | 7/2006 | Michelson | |
| 7,077,844 B2 | 7/2006 | Michelson | |
| 7,097,645 B2 | 8/2006 | Michelson | |
| 7,112,202 B2 | 9/2006 | Michelson | |
| 7,115,130 B2 | 10/2006 | Michelson | |
| 7,118,573 B2 | 10/2006 | Michelson | |
| 7,137,984 B2 | 11/2006 | Michelson | |
| 7,534,254 B1 | 5/2009 | Michelson | |
| 7,625,381 B2 | 12/2009 | Michelson | |
| 7,651,497 B2 | 1/2010 | Michelson | |
| 7,704,250 B2 | 4/2010 | Michelson | |
| 7,704,255 B2 | 4/2010 | Michelson | |
| 7,803,157 B2 | 9/2010 | Michelson | |
| 8,048,075 B2 | 11/2011 | Michelson | |
| 8,123,788 B2 | 2/2012 | Michelson | |
| 8,262,708 B2 | 9/2012 | Michelson | |
| 2002/0115742 A1 | 8/2002 | Trieu et al. | |
| 2004/0220572 A1 | 11/2004 | Michelson | |
| 2005/0059971 A1 | 3/2005 | Michelson | |
| 2005/0187552 A1 | 8/2005 | Michelson | |

FOREIGN PATENT DOCUMENTS

| | | |
|---|---|---|
| DE | 33 01 298 A1 | 2/1984 |
| DE | 36 30 863 A1 | 3/1988 |
| DE | 88 04 457 U1 | 6/1988 |
| DE | 4409833 | 10/1995 |
| DE | 4414781 | 11/1995 |
| DE | 195 42 116 A1 | 5/1997 |
| EP | 0 179 695 A1 | 4/1986 |
| EP | 0 242 842 A2 | 10/1987 |
| EP | 0 276 153 A2 | 7/1988 |
| EP | 0 455 255 A1 | 11/1991 |
| EP | 0 491 211 A1 | 6/1992 |
| EP | 0 538 895 A2 | 4/1993 |
| EP | 0 554 915 | 8/1993 |
| EP | 0 672 397 A1 | 9/1995 |
| EP | 0 689 800 A2 | 1/1996 |
| EP | 0 699 057 A1 | 3/1996 |
| EP | 1 106 144 A1 | 6/2001 |
| FR | 2 570 594 A1 | 3/1986 |
| FR | 2 739 151 A1 | 3/1997 |
| FR | 2 740 321 A1 | 4/1997 |
| SU | 1375252 A1 | 2/1988 |
| SU | 1560165 A1 | 4/1990 |
| SU | 1804317 A3 | 3/1993 |
| WO | WO 88/03781 A1 | 6/1988 |
| WO | WO 90/02526 A1 | 3/1990 |
| WO | WO 94/17744 A1 | 8/1994 |
| WO | WO 94/26193 | 11/1994 |
| WO | WO 95/25474 A1 | 9/1995 |
| WO | WO 05/28164 A1 | 10/1995 |
| WO | WO 95/28973 | 11/1995 |
| WO | WO 95/31941 A1 | 11/1995 |
| WO | WO 95 35067 | 12/1995 |
| WO | WO 96/05778 A1 | 2/1996 |
| WO | WO 96 08206 | 3/1996 |
| WO | WO 96/32071 A1 | 10/1996 |

OTHER PUBLICATIONS

Defendant's Third Supplemental Response to Plaintiffs' Interrogatory Nos. 8-11. Warsaw Orthopedic, Inc. and Medtronic Sofamor Danek, Inc. v. EBI, L.P. and Biomet, Inc. in U.S. District Court for the District of New Jersey; Civil Action No. 2:06-CV-0490; pp. 1-46.

NuVasive, Inc's Preliminary Invalidity Contentions Pursuant to Patent Local Rule 3.3 Regarding U.S. Patent No. 5,860,973, U.S. Patent No. 6,945,933, and U.S. Patent No. 6,592,586; *Medtronic Sofamor Danek USA, Inc., et al. v. NuVasive, Inc.*; United States District Court for the Southern District of California; Case No. 3:08-CV-1512 MMA (AJB); dated Sep. 18, 2009; 16 pages; Appendix A.1 (pp. 1-22); Appendix A.2 (pp. 1-16); Appendix A.3 (pp. 1-21); Appendix A.4 (pp. 1-14); Appendix A.5 (pp. 1-38).

Medtronic Sofamor Danek USA, Inc., et al.'s Preliminary Claim Constructions Regarding U.S. Patent Nos. 6,592,586; 5,860,973; 6,945,933; 7,582,058; 7,207,949; and 7,470,236 Pursuant to Patent L.R. 4.1; *Medtronic Sofamor Danek USA, Inc.; Warsaw Orthopedic, Inc.; Medtronic Puerto Rico Operations Co.; and Medtronic Sofamor Danek Deggendorf, GmbH v. NuVasive, Inc.*; United States District Court Southern District of California; Case No. 3:08-cv-01512-MMA-AJB; dated Sep. 30, 2009; 11 pages.

Medtronic Sofamor Danek USA, Inc., et al.'s Responsive Claim Constructions Regarding U.S. Patent Nos. 6,592,586; 5,860,973; 6,945,933; 7,582,058; 7,207,949; and 7,470,236 Pursuant to Patent L.R. 4.1; *Medtronic Sofamor Danek USA, Inc.; Warsaw Orthopedic, Inc.; Medtronic Puerto Rico Operations Co.; and Medtronic Sofamor Danek Deggendorf, GmbH v. NuVasive, Inc.*; United States District Court Southern District of California; Case No. 3:08-cv-01512-MMA-AJB; dated Oct. 9, 2009; 12 pages.

Nuvasive, Inc.'s Preliminary Claim Constructions and Identification of Extrinsic Evidence Pursuant to Patent L.R. 4.1 for U.S. Patent No. 6,592,586, U.S. Patent No. 5,860,973, U.S. Patent No. 6,945,933, U.S. Patent No. 7,207,949, U.S. Patent No. 7,470,236, and U.S. Patent No. 7,582,058; *Medtronic Sofamor Danek USA, Inc., et al. v. NuVasive, Inc.*; United States District Court Southern District of California; Case No. 3:08-CV-1512 MMA (AJB); dated Sep. 30, 2009; 7 pages.

Nuvasive, Inc.'s Responsive Claim Constructions and Identification of Extrinsic Evidence Pursuant to Patent L.R. 4.1 for U.S. Patent No. 6,592,586, U.S. Patent No. 5,860,973, U.S. Patent No. 6,945,933, U.S. Patent No. 7,207,949, U.S. Patent No. 7,470,236, and U.S. Patent No. 7,582,058; *Medtronic Sofamor Danek Usa, Inc., et al. v. NuVasive, Inc.*; United States District Court Southern District of California; Case No. 3:08-CV-1512 MMA (AJB); dated Oct. 9, 2009; 18 pages.

*Medtronic Sofamor Danek USA, Inc. et al., v. Nuvasive, Inc.*; Medtronic's Third Supplemental Disclosure of Asserted Claims and Infringement Contentions; 5 pages; dated Nov. 6, 2009; Attachment 15, 2 pages.

Joint Claim Construction Chart, Worksheet, and Hearing Statement Pursuant to Patent L.R. 4.2 for U.S. Patent Nos. 6,592,586; 5,860,973; 6,945,933; 7,582,058; and 7,470,236; *Medtronic Sofamor Danek USA, Inc., et al. v. NuVasive, Inc.*; United States District Court Southern District of California; Case No. 3:08-cv-01512 MMA (AJB); Document 102; dated Nov. 23, 2009; 4 pages; Exhibit A, 59 pages, Exhibit F, 46 pages.

Medtronic Sofamor Danek USA, Inc. et al.'s Opening Claim Construction Brief; *Medtronic Sofamor Danek Usa, Inc., et al.* v. *NuVasive, Inc.*; United States District Court Southern District of California; Case No. 3:08-CV01512 MMA (AJB); dated Jan. 11, 2010; 70 pages.

Nuvasive Inc.'s Supplemental Response to Plaintiffs' Interrogatory Nos. 1, 3, 4, 5 and 15; *Medtronic Sofamor Danek USA, Inc., et al.* v. *NuVasive, Inc.*; United States District Court Southern District of California; Case No. 3:08-CV-1512 MMA (AJB); dated Feb. 12, 2010; 13 pages.

*Medtronic Sofamor Danek USA, Inc. et al.,* v. *Nuvasive, Inc.*; Medtronic's Fourth Supplemental Disclosure of Asserted Claims and Infringement Contentions; 8 pages; dated Feb. 12, 2010; Attachment 17, 5 pages.

*Medtronic Sofamor Danek USA, Inc., et al.* v. *Nuvasive, Inc.*; Order Construing Disputed Claim Terms of United States Patent Nos. 5,860,973; 6,945,933; 6,592,586; and 7,470,236; 22 pages; dated Apr. 1, 2010.

*Medtronic Sofamor Danek Usa, Inc., et al.* v. *Nuvasive, Inc.*; Plaintiff Medtronic Sofamor Danek USA, Inc., et al.'s Supplemental Objections and Responses to NuVasive, Inc.'s Second Set of Interrogatories (No. 16); 13 pages; dated May 10, 2010.

*Medtronic Sofamor Danek, Inc.,* v. *Nuvasive, Inc.*; Nuvasive, Inc.'s Corrected Final Invalidity Contentions Regarding U.S. Patent Nos. 5,860,973; 6,592,586; and 6,945,933; 17 pages; dated Jun. 14, 2010; Appendix A.1, 22 pages; Appendix A.2, 16 pages; Appendix A.3, 21 pages; Appendix A.4, 14 pages; Appendix A.5, 38 pages; Appendix A.6, 30 pages; Appendix A.7, 37 pages; Appendix A.8, 64 pages.

*Warsaw Orthopedic, Inc.,* v. *NuVasive, Inc.*; Opening Expert Witness Report of Dr. Michael Marks Regarding Invalidity of the Asserted Claims of U.S. Patent No. 6,592,586; 49 pages; dated Dec. 3, 2010; Exhibit A, 12 pages; Exhibit B, 5 pages; Exhibit H, 140 pages; Exhibit I, 132 pages; Exhibit J, 93 pages; Exhibit K, 80 pages; Exhibit L, 82 pages; Exhibit M, 79 pages; Exhibit N, 80 pages; Exhibit O, 92 pages.

*Warsaw Orthopedic, Inc.,* v. *Nuvasive, Inc.*; Medtronic's Opposition to Nuvasive Inc.'s Motions for Summary Judgment (Redacted Version); 30 pages; Mar. 9, 2011.

*Warsaw Orthopedic, Inc.,* v. *Nuvasive, Inc.*; Medtronic's Responses to Nuvasive's Statement of Undisputed Facts and Medtronic's Statement of Additional Material Facts (Redacted Version); 77 pages; Mar. 9, 2011.

*Warsaw Orthopedic, Inc.,* v. *Nuvasive, Inc.*; Nuvasive's Opposition to Warsaw's Motions for Summary Judgment (Redacted Version); 31 pages; Mar. 9, 2011.

*Warsaw Orthopedic, Inc.,* v. *Nuvasive, Inc.*; Nuvasive's Response to Warsaw's Statement of Undisputed Material Facts (Redacted Version); 89 pages; Mar. 10, 2011.

*Warsaw Orthopedic, Inc.,* v. *Nuvasive, Inc.*; Medtronic's Responses to Nuvasive's Statement of Additional Material Facts (Redacted Version); 39 pages; Mar. 16, 2011.

*Warsaw Orthopedic, Inc.,* v. *Nuvasive, Inc.*; Nuvasive's Reply in Support of Motions for Summary Judgment (Redacted Version); 13 pages; Mar. 16, 2011.

*Warsaw Orthopedic, Inc.,* v. *Nuvasive, Inc.*; Nuvasive's Reply to Warsaw's Statement of Additional Material Facts (Redacted Version); 67 pages; Mar. 16, 2011.

*Warsaw Orthopedic, Inc.,* v. *Nuvasive, Inc.*; Reply Memorandum in Support of Medtronic's Motion for Summary Judgment (Redacted Version); 14 pages; Mar. 16, 2011.

*Medtronic Sofamor Danek USA, Inc., et al,* v. *Nuvasive, Inc.*; Notice and Order Providing Tentative Rulings Re: Parties' Cross Motions for Summary Judgment; 1 page; Mar. 22, 2011.

*Warsaw Orthopedic, Inc.* v. *Nuvasive, Inc.*; Nuvasive, Inc.'s Notice Pursuant to 35 U.S.C. § 282; 11 pages; Jul. 29, 2011.

*Warsaw Orthopedic, Inc.* v. *Nuvasive, Inc.*; Judgment Following Jury Verdict; 9 pages; Sep. 29, 2011.

*Warsaw Orthopedic, Inc.* v. *Nuvasive, Inc.*; Nuvasive, Inc.'s Preliminary Invalidity Contentions Pursuant to Patent Local Rule 3.3 Regarding U.S. Patent No. 6,916,320; 137 pages; Sep. 21, 2012.

*Warsaw Orthopedic, Inc.* v. *Nuvasive, Inc.*; Nuvasive, Inc.'s Preliminary Claim Construction and Identification of Extrinsic Evidence; 8 pages; Oct. 5, 2012.

Expert Report of Robert Piziali, Ph.D., *Medtronic Sofamor Danek USA, Inc., Warsaw Orthopedic, Inc., Medtronic Puerto Rico Operations Company, Medtronic Sofamor Danek Deggendorf, GmbH,* v. *Globus Medical, Inc.* in the United States District Court for the Eastern District of Pennsylvania; Civil Action No. 06-CV-4248-JG; pp. 1-97, Appendix I-CV (pp. 1-11), Appendix II (pp. 1-7), Appendix III (1 page), Appendix IV (3 pages), and Appendix V (65 pages).

Supplement to Expert Report of Robert Piziali, Ph.D., *Medtronic Sofamor Danek USA, Inc., Warsaw Orthopedic, Inc., Medtronic Puerto Rico Operations Company, Medtronic Sofamor Danek Deggendorf, GmbH,* v. *Globus Medical, Inc.* in the United States District Court for the Eastern District of Pennsylvania; Civil Action No. 06-CV-4248-JG; pp. 1-12, Appendix I-CV (pp. 1-11), Appendix II (6 pages), Appendix III (1 pages), Appendix IV (4 pages), and Appendix V (446 pages).

Expert Report of Dr. Paul McAfee, *Medtronic Sofamor Danek USA, Inc., Warsaw Orthopedic, Inc., Medtronic Puerto Rico Operations Company, Medtronic Sofamor Danek Deggendorf, GmbH,* v. *Globus Medical, Inc.* in the United States District Court for the Eastern District of Pennsylvania; Civil Action No. 06-CV-4248-JG; dated Mar. 14, 2008; pp. 1-19.

Supplement to Expert Report of Dr. Paul C. McAfee, MD, *Medtronic Sofamor Danek USA, Inc., Warsaw Orthopedic, Inc., Medtronic Puerto Rico Operations Company, Medtronic Sofamor Danek Deggendorf, GmbH,* v. *Globus Medical, Inc.* in the United States District Court for the Eastern District of Pennsylvania; Civil Action No. 06-CV-4248-JG; dated Apr. 2, 2008; pp. 1-21.

Expert Report of Dr. Paul McAfee, *Medtronic Sofamor Danek USA, Inc., Warsaw Orthopedic, Inc., Medtronic Puerto Rico Operations Company, Medtronic Sofamor Danek Deggendorf, GmbH,* v. *Globus Medical, Inc.* in the United States District Court for the Eastern District of Pennsylvania; Civil Action No. 06-CV-4248-NS; dated May 15, 2008; pp. 1-51, Appendix A (pp. 1-24), Appendix B (1 page), Appendix C (pp. 1-4).

Bohler and Gaudernak, Anterior Plate Stabilization for Fracture-Dislocations of the Lower Cervical Spine, The Journal of Trauma, vol. 20, No. 3, pp. 203-205 (Mar. 1980).

Hitchon, P. et al.; "Techniques in Spinal Fusion and Stabilization;" Thieme; 1995; 365 pages.

Kotani et al., Biomechanical Analysis of Cervical Stabilization Systems, Spine, vol. 19, No. 22, pp. 2529-2539 (Nov. 1994).

Taha and Zuccarello, ORION Anterior Cervical Plate System, Neurosurgery, vol. 38, No. 3, pp. 607-610 (Mar. 1996).

Weis et al., In Vitro Biomechanical Comparison of Multistrand Cables with Conventional Cervical Stabilization, Spine, vol. 21, No. 8, pp. 2108-2114 (Sep. 1996).

Peak Fixation System Anterior Compression Plate Product Catalog; 8 pages; (Depuy Motech, Inc. 1996), prior to Jul. 1, 2004.

DePuy Motech Peak Anterior Compression Plate Brochure; 1996; 2 pages.

Dickman et al., Technique of Screw Fixation of the Cervical Spine, BNI Quarterly, vol. 8, No. 2 pp. 9-26 (1992), prior to Jul. 1, 2004.

Baldwin et al., Failure of a titanium anterior cervical plate implant: microstructural analysis of failure, Case Report, *J. Neurosurgery,* vol. 83, No. 4, cover page and pp. 741-743 (Oct. 1995).

Baskin, Jonathan J., et al.; "Techniques of Anterior Cervical Plating;" *Operative Techniques in Neurosurgery;* vol. 1, No. 2; Jun. 1998; pp. 90-102.

Bauer, et al.; "Atlas of Spinal Operations;" Thieme; 1993; 459 pages.

Ebraheim et al., Osteosynthesis of the Cervical Spine With an Anterior Plate, *Orthopedics,* vol. 18, No. 2, cover page and pp. 141-147 (Feb. 1995).

Kostuik et al., Anterior Cervical Plate Fixation with the Titanium Hollow Screw Plate System, *Spine,* vol. 18, No. 10, pp. 1273-1278 (1993), prior to Jul. 1, 2004.

LaRocca, Henry, et al.; "Spine—Symposium on Internal Fixation;" vol. 16, No. 3S; Mar. 1991; 187 pages; including: Ripa, et al.; "Series of Ninety-Two Traumatic Cervical Spine Injuries Stabilized with Anterior ASIF Plate Fusion Technique;" pp. S46-S55.

Rengachary et al.; "Neurosurgery;" Second Edition, vol. II, Part VIII; 1996; 2 cover pages and pp. 2983-2986.
Rengachery et al., "Stabilization of the Cervical Spine with the Locking Plate System" in *Techniques in Spinal Fusion and Stabilization*, pp. 176-190 (1995), prior to Jul. 1, 2004.
Sherk, et al.; "The Cervical Spine: An Atlas of Surgical Procedures;" Lippincot; 1994; 341 pages.
SpineTech Inc.; Cervi-Lok Cervical Fixation System; 1994; 2 pages.
Suh et al., Anterior Cervical Plate Fixation with the Titanium Hollow Screw Plate System, A Preliminary Report, *Spine*, vol. 15, No. 10, cover page and pp. 1079-1081 (Nov. 1990).
Zimmer Product Encyclopedia (Zimmer USA Jun. 1978).
Codman Anterior Cervical Plate System (advertised in Spine, vol. 20, No. 13 (Sep. 1995)).
AESCULAP Scientific Information Booklet; *Anterior Cervical Fusion and Interbody Stabilization with the Trapezial Osteosynthetic Plate Technique* by Wolfhard Casper; Feb. 1986.
Article from Plastic and Reconstructive Surgery; *Comparison of Compression and Torque Measurements of Self-Tapping and Pretapped Screws* by John T. Phillips, M.D., F.R.C.S. (C), and Berton A. Rahn, M.D., D.D.S.; Mar. 1989.
Article from The Journal of Prosthetic Dentistry; *Bone-implant interface structures after nontappinq and tapping insertion of screw-type titanium alloy endosseous implants* by Keiichi Satomi, D.D.S.; Yasumasa Akagawa, D.D.S., Ph.D.; and Hiroshima Tsuru, D.D.S., Ph.D.; Mar. 1988; vol. 59, No. 3.
Brochure by Synthes Spine for *Cervical Spine Locking Plate*; 1991.
ORION Brochure, Anterior Cervical Plate System, Surgical Technique, as described by Gary L. Lowery, M.D., Ph.D. (Jul. 1996); pp. 1-24 plus 1 page.
CODMAN Brochure; *Anterior Cervical Plate System*; Sep. 1995.
Advertisement for The AcuFix Anterior Cervical Plate System; Spinal Concepts; Prior to Jul. 1, 2004.
European Search Report for EP 98 904937; date completed Jun. 21, 2001.
European Search Report for EP 98 906158; date completed Jun. 26, 2001.
Article from The Surgeon; The Anterior Plating of the Cervical Spine with the Titanium Hollow Screw System by E. Morscher, F. Sutter, H. Jenny and S. Olerud; (1986).
ACROMED; AcroPlate Anterior Cervical System: Ordering Information for Implants and Instruments; (Jan. 1994).
ACROMED; Kaneda Anterior Spinal Instrumentation System, Technique Manual; Prior to Jul. 1, 2004.
ACROMED; University Plate Titanium Anterior System: Ordering Information for Implants and Instruments; (Sep. 1994).
Caspar et al.; Experimental and Clinical Studies, Anterior Cervical Fusion and Caspar Plate Stabilization for Cervical Trauma; Neurosurgery; vol. 25; No. 4; Oct. 1989; pp. 491-502.
Caspar, Wolfhard; Anterior Cervical Fusion and Interbody Stabilization with the Trapezial Osteosynthetic Plate Technique; AESCULAP Scientific Information Booklet.
Cervi-Lok Cervical Fixation System, Surgical Technique Manual; Spine-Tech, Inc.; 1995; 21 pages.
Cloward Instrument Corporation; Brochure, New Cloward Cervical Dislocation Reducer; Catalog No. C17-1000; 1 page; Prior to Jul. 1, 2004.
Cloward Instrument Corporation; Brochure, New Cloward Lumbar Vertebra Spreader; Catalog. No. C61-1025/C61-1026; 1 page; Prior to Jul. 1, 2004.
Cloward Instrument Corporation; Catalog, Cloward Instruments; 1993; 40 pages.
Davne et al.; "Complications of Lumbar Spinal Fusion with Transpedicular Instrumentation;" *Spine*; Jun. 1992; pp. S184-S189.
Foley et al.; Aline Anterior Cervical Plating System: Surgical Technique; Surgical Dynamics; 1998; pp. 1-16.
Stryker Implants; alpha plate; 1997.
Synthes Spine; New Additions, Cervical Spine Locking Plate System; 1995; pp. 1-17, plus 3 pages.
Synthes Spine; Product Profile; Nov. 1993; pp. 1-8.
Synthes Spine; The Titanium, Anterior Thoracolumbar Locking Plate System, Technique Guide; Apr. 1994; pp. 1-13.
European Search Report dated Jan, 20, 2004 of corresponding European Patent Application No. 03028649.
Relevant portions of the '586 patent file history. Including: File Wrapper Jacket (1 page); Application filed Jul. 17, 2000 (pp. 1-161); Restriction requirement mailed May 18, 2001 (5 pages); Reply to Restriction Requirement mailed Sep. 18, 2001 (2 pages); Office Action mailed Dec. 6, 2001 (6 pages); Fee Record Sheet (1 page); Bib Data Sheet (1 page); Amendment faxed Jun. 6, 2002 (35 pages); Amendment faxed Aug. 29, 2002 (21 pages); Notice of Allowability mailed Sep. 10, 2002 (8 pages); Amendment mailed Dec. 10, 2002 (27 pages); Amendment faxed Feb. 25, 2003 (13 pages); Notice of Allowability mailed Mar. 4, 2003 (5 pages); Amendment mailed Apr. 8, 2003 (2 pages); Office Communication mailed May 8, 2003 (2 pages).
Relevant portions of U.S. Appl. No. 09/669,912. Including: File Wrapper Jacket (1 page); Amendment mailed Sep. 24, 2001 (18 pages).
Relevant portions of U.S. Appl. No. 11/110,161. Including: Continuing Application Transmittal filed Apr. 20, 2005 (1 page); Office Action mailed Sep. 3, 2008 (13 pages).
Relevant portions of the '542 patent file history. Including: File Wrapper Jacket (1 page); Amendment faxed Nov. 19, 2001 (15 pages); Notice of Allowability signed Dec. 4, 2001 (4 pages); and Amendment faxed Mar. 6, 2002 (12 pages).
Relevant portions of the '050 patent file history. Including: Continuing Application Transmittal filed Apr. 9, 2003 (1 page); Notice of Allowability with two initialed PTO/SB/08s mailed Feb. 24, 2005 (9 pages).
Relevant portions of the '320 patent file history. Including: Divisional Application Transmittal filed Sep. 24, 2002 (1 page); Amendment mailed Sep. 24, 2002 (8 pages); Office Action mailed Nov. 26, 2004 (7 pages); Interview Summary mailed Mar. 1, 2005 (2 pages); Amendment faxed Mar. 2, 2005 (13 pages).
Relevant portions of the '390 patent file history. Including: Continuing Application Transmittal with claims filed Mar. 11, 2003 (8 pages); Notice of Allowance with initialed PTO/SB/08s and 892 mailed Feb. 24, 2005 (15 pages).
Relevant portions of the '051 patent file history. Including: Continuing Application Transmittal filed Apr. 10, 2003 (1 page); Notice of Allowability with initialed PTO/SB/08s mailed Feb. 24, 2005 (9 pages).
Relevant portions of U.S. Appl. No. 10/802,906. Including: Continuing Application Transmittal filed Mar. 17, 2004 (1 page); Office Action mailed Dec. 10, 2008 (10 pages).
NuVasive Helix ACP Surgical Technique; 2008; cover page, pp. 1-21, and back page.
Relevant portions of U.S. Appl. No. 10/938,380. Including: Continuing Application Transmittal filed Sep. 10, 2004 (1 page); Office Action mailed Oct. 2, 2007 (10 pages); Amendment and Information Diclosure Statement faxed Jan. 2, 2008 (20 pages).
Relevant portions of U.S. Appl. No. 10/938,380. Including: Advisory Action mailed Jan. 7, 2009 (3 pages); Continuing Application Transmittal mailed Sep. 10, 2004 (1 page).
Relevant portions of U.S. Appl. No. 10/938,380. Including: Office Action mailed Oct. 2, 2007 (10 pages); Amendment with Information Disclosure Statement faxed Jan. 2, 2008 (20 pages).
Relevant portions of U.S. Appl. No. 09/618,036. Including: File Wrapper Jacket (1 page); Application filed Jul. 17, 2000 (pp. 1, 79-160); Amendment faxed Jul. 11, 2002 (11 pages); Office Action with initialed PTO/SB/08s and PTO-892 mailed Aug. 5, 2002 (11 pages); Amendment faxed Jan. 9, 2003 (26 pages); Amendment faxed Jan. 14, 2003 (12 pages); Notice of Allowability with initialed PTO/SB/08 mailed Jan. 21, 2003 (6 pages).
Relevant portions of U.S. Appl. No. 09/022,293. Incluing: File wrapper jacket (1page); Patent Application Transmittal filed Feb. 11, 1998 (1 page); Fee Transmittal mailed Feb. 11, 1998 (1 page); Application filed on Feb. 11, 1998 (pp. 1, 73-148); Restriction Requirement mailed Mar. 23, 1999 (5 pages); Reply to Restriction Requirement mailed Jul. 22, 1999 (2 pages); Office Action with initialed PTO/SB/08 and PTO-82 mailed Oct. 13, 1999 (14 pages); Reply to Office Action mailed Apr. 13, 2000 (17 pages, 2 copies); Notice of Allowability with initialed PTO/SB/08 mailed Sep. 26, 2000 (5 pages).

Relevant portions of U.S. Appl. No. 09/022,293. Including: File Wrapper Jacket (1 page); Restriction Requirement mailed Mar. 23, 1999 (6 pages); Reply to Restriction Requirement mailed Jul. 22, 1999 (2 pages); Office Action mailed Oct. 13, 1999 (11 pages); Application filed on Feb. 11, 1998 (pp. 1-149); Reply to Office Action mailed Apr. 13, 2000 (17 pages); Notice of Allowability signed Sep. 22, 2000 (3 pages).

Relevant portions of U.S. Appl. No. 09/022,293. Including: File Wrapper Jacket (1 page); Application filed on Feb. 11, 1998 (pp. 1-102); Restriction Requirement mailed Mar. 23, 1999 (6 pages); Reply to Restriction Requirement mailed Jul. 22, 1999 (2 pages); Office Action mailed Oct. 13, 1999 (11 pages); Reply to Office Action mailed Apr. 13, 2000 (17 pages).

Request for Inter Partes Reexamination of U.S. Patent No. 6,428,542, dated Mar. 9, 2009, cover page and pp. 1-71.

Corrected Request for Inter Partes Reexamination of U.S. Patent No. 6,428,542, dated Apr. 6, 2009, cover page and pp. 1-74.

Second Corrected Request for Inter Partes Reexamination of U.S. Patent No. 6,428,542, dated May 20, 2009, pp. 1-82.

Request for Inter Partes Reexamination of U.S. Patent No. 6,592,586, dated Mar. 9, 2009, cover page and pp. 1-101.

Corrected Request for Inter Partes Reexamination of U.S. Patent No. 6,592,586, dated May 18, 2009, pp. 1-108.

Request for Inter Partes Reexamination of U.S. Patent No. 6,936,050, dated Mar. 9, 2009, cover page and pp. 1-53.

Request for Inter Partes Reexamination of U.S. Patent No. 6,916,320, dated Mar. 9, 2009, cover page and pp. 1-33.

Corrected Request for Inter Partes Reexamination of U.S. Patent No. 6,916,320, dated Apr. 6, 2009, pp. 1-35.

Request for Inter Partes Reexamination of U.S. Patent No. 6,969,390, dated Mar. 9, 2009, cover page and pp. 1-71.

Corrected Request for Inter Partes Reexamination of U.S. Patent No. 6,969,390, dated May 18, 2009, pp. 1-80.

Request for Inter Partes Reexamination of U.S. Patent No. 6,936,051, dated Mar. 9, 2009, cover page and pp. 1-51.

Office Action from U.S. Appl. No. 11/110,161 mailed Jun. 24, 2009; 5 pages.

Preliminary Amendment from U.S. Appl. No. 09/618,038; mailed Dec. 22, 2000; 20 pages.

Supplemental Preliminary Amendment from U.S. Appl. No. 09/618,038; mailed Sep. 20, 2001; 9 pages.

Notice of Allowance from U.S. Appl. No. 09/618,038; mailed Jan. 28, 2002; 5 pages.

Preliminary Amendment from U.S. Appl. No. 09/618,037; mailed Apr. 18, 2001; 19 pages.

Notice of Allowance from U.S. Appl. No. 09/618,037; mailed Mar. 21, 2002; 4 pages.

Office Action from Reexamination Proceeding No. 95/000,446; mailed Jun. 30, 2009; 16 pages.

Amendment from Reexamination Proceeding No. 95/000,446; mailed Aug. 29, 2009; 46 pages.

Action Closing Prosecution from Reexamination Proceeding No. 95/000,446; mailed Feb. 7, 2010; 35 pages.

Amendment from Reexamination Proceeding No. 95/000,446; mailed Mar. 17, 2010; 44 pages.

Right of Appeal Notice from Reexamination Proceeding No. 95/000,446; mailed Apr. 28, 2010; 36 pages.

Third Party Comments to Patent Owner's New Amendment of May 28, 2010 from Reexamination Proceeding No. 95/000,446; dated Sep. 20, 2010; 28 pages.

Right of Appeal Notice from Reexamination Proceeding No. 95/000,446; mailed Sep. 29, 2010; 35 pages.

Third Party Requester's Brief on Appeal from Reexamination Proceeding No. 95/000,446; dated Dec. 29, 2010; 57 pages.

Respondent's Brief from Reexamination Proceeding No. 95/000,446; dated Jan. 31, 2011; 21 pages.

Examiner's Answer from Reexamination Proceeding No. 95/000,446; mailed Mar. 11, 2011; 4 pages.

Third Party Requester's Rebuttal Brief on Appeal from Reexamination Proceeding No. 95/000,446; dated Apr. 11, 2011; 15 pages.

Board of Patent Appeals and Interferences Decision on Appeal from Reexamination Proceeding No. 95/000,446; dated Aug. 5, 2011; 26 pages.

Request to Reopen Prosecution Before the Examiner Under 37 C.F.R. § 41.77(b)(1) from Reexamination Proceeding No. 95/000,446; dated Sep. 6, 2011; 71 pages.

Third Party Requester Comments After Patent Owner's Request to Reopen Prosecution and the Accompanying Claim Amendment and Declaration of Dr. Gary L. Lowery Under 37 C.F.R. § 1.132 from Reexamination Proceeding No. 95/000,446; dated Oct. 6, 2011; 77 pages.

Examiner's Determination under 37 C.F.R. § 41.77(d) from Reexamination Proceeding No. 95/000,446; mailed Dec. 16, 2011; 27 pages.

Patent Owner's Comments on Statement of Reasons for Patentability and/or Confirmation Pursuant to 37 C.F.R. § 41.77(e) from Reexamination Proceeding No. 95/000,446; dated Jan. 17, 2012; 13 pages.

Amendment om Reexamination Proceeding No. 95/000,446; dated Jan. 17, 2012; 54 pages.

Third Party Requester Comments under 37 C.F.R. § 41.77(e) After Examiner's Determination under 37 C.F.R. § 41.77(d) from Reexamination Proceeding No. 95/000,446; dated Jan. 17, 2012; 6 pages.

Reply to Patent Owner's Comments under 37 C.F.R. § 41.77(e) from Reexamination Proceeding No. 95/000,446; dated Feb. 17, 2012; 9 pages.

Decision Granting Petitions under §§ 1.182 and 1.183 from Reexamination Proceeding No. 95/000,446; dated Dec. 31, 2012; 10 pages.

Amendment from U.S. Appl. No. 09/618,157; faxed Aug. 13, 2002; 40 pages.

Amendment from U.S. Appl. No. 09/618,157; faxed Nov. 4, 2002; 52 pages.

Notice of Allowance from U.S. Appl. No. 09/618,157; mailed Nov. 12, 2002; 7 pages.

Office Action from U.S. Appl. No. 09/754,733; mailed Dec. 5, 2001; 7 pages.

Amendment from U.S. Appl. No. 09/754,733; faxed Apr. 5, 2002; 29 pages.

Notice of Allowance from U.S. Appl. No. 09/754,733; mailed Jul. 15, 2002; 8 pages.

Amendment from U.S. Appl. No. 10/409,805; mailed Sep. 11, 2003; 3 pages.

Notice of Allowance from U.S. Appl. No. 10/409,805; mailed Jun. 15, 2005; 4 pages.

Office Action from Reexamination Proceeding No. 95/000,451; mailed Jun. 17, 2009; 11 pages.

Amendment from Reexamination Proceeding No. 95/000,451; faxed Aug. 17, 2009; 26 pages.

Third Party Comments After Patent Owner's Response and in Response to the Notice of Oct. 15, 2009 from Reexamination Proceeding No. 95/000,451; dated Oct. 30, 2009; 60 pages.

Action Closing Prosecution from Reexamination Proceeding No. 95/000,451; mailed Feb. 16, 2010; 27 pages.

Amendment from Reexamination Proceeding No. 95/000,451; dated Mar. 16, 2010; 24 pages.

Right of Appeal Notice from Reexamination Proceeding No. 95/000,451; dated Apr. 28, 2010; 25 pages.

Corrected Third Party Comments to Patent Owner's Proposed Amendment After the Close of Prosecution from Reexamination Proceeding No. 95/000,451; dated May 13, 2010; 28 pages.

Third Party Requester's Brief on Appeal from Reexamination Proceeding No. 95/000,451; dated Jul. 28, 2010; 45 pages.

Respondent's Brief on Appeal from Reexamination Proceeding No. 95/000,451; faxed Aug. 30, 2010; 27 pages.

Corrected Third Party Requester's Brief on Appeal from Reexamination Proceeding No. 95/000,451; dated Sep. 27, 2010; 44 pages.

Examiner's Answer from Reexamination Proceeding No. 95/000,451; mailed Mar. 23, 2011; 4 pages.

Third Party Requester's Rebuttal Brief on Appeal from Reexamination Proceeding No. 95/000,451; dated Apr. 25, 2011; 12 pages.

Board of Patent Appeals and Interferences Decision on Appeal from Reexamination Proceeding No. 95/000,451; dated Aug. 5, 2011; 34 pages.

Request to Reopen Prosecution Before the Examiner Under 37 C.F.R. § 41.77(b)(1) from Reexamination Proceeding No. 95/000,451; dated Sep. 6, 2011; 52 pages.

Third Party Requester Comments After Patent Owner's Request to Reopen Prosecution and the Accompanying Claim Amendment and Declaration of Dr. Gary L. Lowery Under 37 C.F.R. § 1.132 from Reexamination Proceeding No. 95/000,451; dated Oct. 6, 2011; 76 pages.
Examiner's Determination from Reexamination Proceeding No. 95/000,451; mailed Dec. 16, 2011; 19 pages.
Amendment from Reexamination Proceeding No. 95/000,451; dated Jan. 16, 2012; 31 pages.
Patent Owner's Comments on Statement of Reasons for Patentability and/or Confirmation Pursuant to 37 C.F.R. § 41.77(e) from Reexamination Proceeding No. 95/000,451; dated Jan. 16, 2012; 6 pages.
Third Party Requester Comments under 37 C.F.R. § 41.77(e) After Examiner's Determination under 37 C.F.R. § 41.77(d) from Reexamination Proceeding No. 95/000,451; dated Jan. 17, 2012; 8 pages.
Reply to Patent Owner's Comments under 37 C.F.R. § 41.77(e) from Reexamination Proceeding No. 95/000,451; dated Feb. 16, 2012; 6 pages.
Decision Dismissing Petitions under §§ 1.182 and 1.183 from Reexamination Proceeding No. 95/000,451; dated Dec. 31, 2012; 9 pages.
Action Closing Prosecution from Reexamination Proceeding No. 95/000,448; mailed Jun. 18, 2009; 18 pages.
Right of Appeal Notice from Reexamination Proceeding No. 95/000,448; mailed Aug. 13, 2009; 19 pages.
Third Party Requester's Brief on Appeal from Reexamination Proceeding No. 95/000,448; dated Nov. 12, 2009; 38 pages.
Respondent's Brief from Reexamination Proceeding No. 95/000,448; faxed Dec. 14, 2009; 20 pages.
Examiner's Answer from Reexamination Proceeding No. 95/000,448; mailed Feb. 16, 2010; 24 pages.
Third Party Requester's Rebuttal Brief on Appeal from Reexamination Proceeding No. 95/000,448; dated Mar. 16, 2010; 10 pages.
Board of Patent Appeals and Interferences Decision on Appeal from Reexamination Proceeding No. 95/000,448; mailed Oct. 21, 2010; 19 pages.
Request to Reopen Prosecution Before the Examiner Under 37 CFR 41.77(b)(1) from Reexamination Proceeding No. 95/000,448; faxed Nov. 22, 2010; 16 pages.
Corrected Third Party Requester Comments After Patent Owner's Request to Reopen Prosecution and the Accompanying Claim Amendment from Reexamination Proceeding No. 95/000,448; filed Feb. 2, 2011; 114 pages.
Office Action from Reexamination Proceeding No. 95/000,448; mailed Mar. 10, 2011; 48 pages.
Third Party Requester Comments Pursuant to 37 CFR § 41.77(e) from Reexamination Proceeding No. 95/000,448; dated Apr. 11, 2011; 33 pages.
Board of Patent Appeals and Interferences Decision on Appeal from Reexamination Proceeding No. 95/000,448; mailed Sep. 27, 2012; 37 pages.
Notice of Allowance from U.S. Appl. No. 10/410,902; mailed Jun. 16, 2005; 4 pages.
Office Action from Reexamination Proceeding No. 95/000,449; mailed Jun. 18, 2009; 11 pages.
Amendment from Reexamination Proceeding No. 95/000,449; faxed Aug. 17, 2009; 16 pages.
Third Party Comments After Patent Owner's Response from Reexamination Proceeding No. 95/000,449; dated Oct. 30, 2009; 17 pages.
Action Closing Prosecution from Reexamination Proceeding No. 95/000,449; mailed Feb. 16, 2010; 17 pages.
Right of Appeal Notice from Reexamination Proceeding No. 95/000,449; mailed Mar. 24, 2010; 18 pages.
Third Party Requester's Brief on Appeal from Reexamination Proceeding No. 95/000,449; dated Jun. 23, 2010; 38 pages.
Respondent's Brief from Reexamination Proceeding No. 95/000,449; faxed Jul. 23, 2010; 19 pages.
Examiner's Answer from Reexamination Proceeding No. 95/000,449; mailed Aug. 23, 2010; 3 pages.
Third Party Requester's Rebuttal Brief on Appeal from Reexamination Proceeding No. 95/000,449; dated Sep. 23, 2010; 12 pages.
Board of Patent Appeals and Interferences Decision on Appeal from Reexamination Proceeding No. 95/000,449; mailed Mar. 9, 2011; 20 pages.
Request to Reopen Prosecution Before the Examiner Under 37 C.F.R. § 41.77(b)(1) from Reexamination Proceeding No. 95/000,449; dated Apr. 11, 2011; 149 pages.
Record of Oral Hearing from Reexamination Proceeding No. 95/000,449; hearing held Jan. 5, 2011, record mailed May 27, 2011; 19 pages.
Third Party Requester Comments After Patent Owner's Request to Reopen Prosecution and the Accompanying Claim Amendment from Reexamination Proceeding No. 95/000,449; dated Jul. 5, 2011; 65 pages.
Office Action from Reexamination Proceeding No. 95/000,449; dated Aug. 11, 2011; 20 pages.
Amendment from Reexamination Proceeding No. 95/000,449; dated Sep. 12, 2011; 8 pages.
Patent Owner's Comments on Statement of Reasons for Patentability and/or Confirmation Pursuant to 37 C.F.R. § 41.77(e) from Reexamination Proceeding No. 95/000,449; dated Sep. 12, 2011; 4 pages.
Third Party Requester's Comments Under 37 C.F.R. § 41.77(e) After Examiner's Determination Under 37 C.F.R. § 41.77(d) from Reexamination Proceeding No. 95/000,449; dated Sep. 12, 2011; 4 pages.
Reply to Patent Owner's Comments Under 37 C.F.R. § 41.77(e) from Reexamination Proceeding No. 95/000,449; dated Oct. 12, 2011; 4 pages.
Board of Patent Appeals and Interferences Decision on Appeal from Reexamination Proceeding No. 95/000,449; dated Jun. 25, 2012; 18 pages.
Request for Rehearing under 37 C.F.R. § 41.79 from Reexamination Proceeding No. 95/000,449; dated Jul. 25, 2012; 19 pages.
Amendment from U.S. Appl. No. 10/410,918; mailed Sep. 11, 2003; 3 pages.
Notice of Allowance from U.S. Appl. No. 10/410,918; mailed Feb. 24, 2005; 7 pages.
Notice of Allowance from U.S. Appl. No. 10/410,918; mailed Jun. 15, 2005; 4 pages.
Amendment from U.S. Appl. No. 10/664,776; mailed Sep. 17, 2003; 3 pages.
Office Action from U.S. Appl. No. 10/664,776; mailed Mar. 16, 2005; 4 pages.
Amendment from U.S. Appl. No. 10/664,776; faxed Sep. 16, 2005; 5 pages.
Office Action from U.S. Appl. No. 10/664,776; mailed Nov. 14, 2005; 8 pages.
Amendment from U.S. Appl. No. 10/664,776; faxed May 15, 2006; 8 pages.
Office Action from U.S. Appl. No. 10/664,776; mailed Jun. 30, 2006; 7 pages.
Reply to Office Action from U.S. Appl. No. 10/664,776; faxed Aug. 4, 2006; 2 pages.
Interview Summary from U.S. Appl. No. 10/664,776; mailed Aug. 11, 2006; 4 pages.
Notice of Allowance from U.S. Appl. No. 10/664,776; mailed Aug. 23, 2006; 6 pages.
Amendment from U.S. Appl. No. 10/883,086; faxed Sep. 10, 2004; 5 pages.
Reply to Communication from U.S. Appl. No. 10/883,086; faxed Feb. 23, 2005; 5 pages.
Office Action from U.S. Appl. No. 10/883,086; mailed Aug. 1, 2005; 6 pages.
Amendment from U.S. Appl. No. 10/883,086; faxed Feb. 1, 2006; 8 pages.
Office Action from U.S. Appl. No. 10/883,086; mailed Feb. 16, 2006; 5 pages.
Amendment from U.S. Appl. No. 10/883,086; mailed Aug. 15, 2006; 6 pages.
Office Action from U.S. Appl. No. 10/883,086; mailed Oct. 26, 2006; 5 pages.
Reply to Office Action from U.S. Appl. No. 10/883,086; faxed Jan. 22, 2007; 2 pages.
Notice of Allowance from U.S. Appl. No. 10/883,086; mailed Sep. 13, 2007; 4 pages.

Office Action from U.S. Appl. No. 10/883,086; mailed Jan. 7, 2008; 7 pages.
Amendment from U.S. Appl. No. 10/883,086; faxed Apr. 3, 2008; 10 pages.
Notice of Allowance from U.S. Appl. No. 10/883,086; mailed Aug. 13, 2008; 4 pages.
Office Action from U.S. Appl. No. 10/883,086; mailed Jan. 13, 2009; 7 pages.
Amendment from U.S. Patent Application No. 10/883,086; mailed Jul. 13, 2009; 12 pages.
Notice of Allowance from U.S. Appl. No. 10/883,086; mailed Dec. 1, 2009; 4 pages.
Amendment from U.S. Appl. No. 11/110,161; mailed Oct. 8, 2008; 10 pages.
Restriction Requirement from U.S. Appl. No. 11/110,161; mailed Jun. 24, 2009; 5 pages.
Amendment and Election of Species from U.S. Appl. No. 11/110,161; filed Nov. 23, 2009; 8 pages.
Office Action from U.S. Appl. No. 11/110,161; mailed Feb. 19, 2010; 7 pages.
Amendment from U.S. Appl. No. 11/110,161; faxed Aug. 19, 2010; 10 pages.
Supplemental Amendment from U.S. Appl. No. 11/110,161; dated Mar. 30, 2012; 14 pages.
Office Action from U.S. Appl. No. 09/022,344; mailed Sep. 10, 1999; 6 pages.
Reply to Office Action from U.S. Appl. No. 09/022,344; mailed Feb. 28, 2000; 4 pages.
Notice of Allowance from U.S. Appl. No. 09/022,344; mailed May 3, 2000; 6 pages.
Notice of Allowance from U.S. Appl. No. 09/022,344; mailed Aug. 16, 2000; 2 pages.
Preliminary Amendment from U.S. Appl. No. 09/669,912; mailed Sep. 26, 2000; 7 pages.
Office Action from U.S. Appl. No. 09/669,912; mailed Mar. 23, 2001; 9 pages.
Amendment from U.S. Appl. No. 09/669,912; faxed Dec. 17, 2001; 24 pages.
Notice of Allowance from U.S. Appl. No. 09/669,912; mailed Dec. 18, 2001; 4 pages.
Amendment from U.S. Appl. No. 10/098,991; mailed Mar. 15, 2002; 9 pages.
Notice of Allowance from U.S. Appl. No. 10/098,991; mailed Oct. 4, 2004; 10 pages.
Amendment from U.S. Appl. No. 10/098,991; faxed Jan. 4, 2005; 6 pages.
Notice of Allowance from U.S. Appl. No. 10/098,991; mailed Jan. 26, 2005; 4 pages.
Amendment from U.S. Appl. No. 10/098,991; faxed Apr. 26, 2005; 15 pages.
Notice of Allowance from U.S. Appl. No. 10/098,991; mailed Feb. 17, 2006; 9 pages.
Amendment from U.S. Appl. No. 10/802,906; mailed Jun. 25, 2004; 3 pages.
Office Action from U.S. Appl. No. 10/802,906; mailed May 16, 2005; 6 pages.
Amendment from U.S. Appl. No. 10/802,906; faxed Nov. 15, 2005; 7 pages.
Office Action from U.S. Appl. No. 10/802,906; mailed Mar. 20, 2006; 6 pages.
Amendment After Final from U.S. Appl. No. 10/802,906; faxed Aug. 7, 2006; 16 pages.
Advisory Action from U.S. Appl. No. 10/802,906; mailed Aug. 21, 2006; 3 pages.
Amendment from U.S. Appl. No. 10/802,906; mailed Aug. 30, 2006; 12 pages.
Office Action from U.S. Appl. No. 10/802,906; mailed Oct. 31, 2006; 10 pages.
Amendment from U.S. Appl. No. 10/802,906; faxed Apr. 30, 2007; 13 pages.
Office Action from U.S. Appl. No. 10/802,906; mailed Jul. 30, 2007; 10 pages.
Amendment from U.S. Appl. No. 10/802,906; faxed Nov. 30, 2007; 16 pages.
Office Action from U.S. Appl. No. 10/802,906; mailed Apr. 8, 2008; 13 pages.
Reply After Final from U.S. Appl. No. 10/802,906; faxed Jun. 9, 2008; 7 pages.
Advisory Action from U.S. Appl. No. 10/802,906; mailed Jun. 26, 2008; 3 pages.
Pre-Appeal Brief Request for Review from U.S. Appl. No. 10/802,906; faxed Jul. 8, 2008; 5 pages.
Amendment from U.S. Appl. No. 10/802,906; faxed Oct. 14, 2008; 13 pages.
Reply to Office Action from U.S. Appl. No. 10/802,906; faxed Jun. 10, 2009; 7 pages.
Office Action from U.S. Appl. No. 10/802,906; mailed Oct. 2, 2009; 11 pages.
Amendment from U.S. Appl. No. 10/802,906; faxed Sep. 30, 2010; 12 pages.
Office Action from U.S. Appl. No. 10/802,906; mailed Dec. 8, 2010; 10 pages.
Reply to Office Action from U.S. Appl. No. 10/802,906; filed Jun. 3, 2011; 3 pages.
Notice of Allowance from U.S. Appl. No. 10/802,906; mailed Aug. 19, 2011; 4 pages.
Office Action from U.S. Appl. No. 10/883,087; mailed Sep. 16, 2005; 5 pages.
Amendment from U.S. Appl. No. 10/883,087; faxed Mar. 10, 2006; 7 pages.
Office Action from U.S. Appl. No. 10/883,087; mailed May 25, 2006; 6 pages.
Amendment from U.S. Appl. No. 10/883,087; faxed Nov. 22, 2006; 6 pages.
Office Action from U.S. Appl. No. 10/883,087; mailed Feb. 20, 2007; 5 pages.
Reply to Office Action from U.S. Appl. No. 10/883,087; mailed Mar. 14, 2007; 2 pages.
Office Action from U.S. Appl. No. 10/883,087; mailed Jun. 14, 2007; 6 pages.
Amendment from U.S. Appl. No. 10/883,087; faxed Sep. 7, 2007; 8 pages.
Office Action from U.S. Appl. No. 10/883,087; mailed Nov. 26, 2007; 8 pages.
Reply After Final from U.S. Appl. No. 10/883,087; faxed Feb. 13, 2008; 4 pages.
Office Action from U.S. Appl. No. 10/883,087; mailed Apr. 14, 2008; 10 pages.
Amendment from U.S. Appl. No. 10/883,087; faxed Jul. 14, 2008; 8 pages.
Office Action from U.S. Appl. No. 10/883,087; mailed Oct. 17, 2008; 8 pages.
Reply After Final from U.S. Appl. No. 10/883,087; faxed Dec. 16, 2008; 5 pages.
Office Action from U.S. Appl. No. 10/883,087; mailed Jan. 27, 2009; 9 pages.
Reply to Office Action from U.S. Appl. No. 10/883,087; mailed Jul. 24, 2009; 8 pages.
Notice of Allowance from U.S. Appl. No. 10/883,087; mailed Oct. 19, 2009; 4 pages.
Amendment from U.S. Appl. No. 10/938,380; mailed Nov. 26, 2004; 11 pages.
Office Action from U.S. Appl. No. 10/938,380; mailed Oct. 6, 2008; 7 pages.
Reply After Final from U.S. Appl. No. 10/938,380; faxed Dec. 8, 2008; 13 pages.
Amendment rom U.S. Appl. No. 10/938,380; mailed Sep. 23, 2009; 8 pages.
Office Action from U.S. Appl. No. 10/938,380; mailed Feb. 18, 2010; 11 pages.
Amendment from U.S. Appl. No. 10/938,380; faxed Aug. 18, 2010; 9 pages.
Office Action from U.S. Appl. No. 10/938,380; mailed Nov. 24, 2010; 8 pages.

Amendment from U.S. Appl. No. 10/938,380; filed Mar. 24, 2011; 13 pages.
Office Action from U.S. Appl. No. 10/938,380; mailed Apr. 11, 2011; 9 pages.
Amendment from U.S. Appl. No. 10/938,380; filed Oct. 11, 2011; 14 pages.
Notice of Allowance from U.S. Appl. No. 10/938,380; mailed Dec. 8, 2011; 8 pages.
Notice of Allowance from U.S. Appl. No. 13/406,178; mailed Aug. 1, 2012; 7 pages.

* cited by examiner

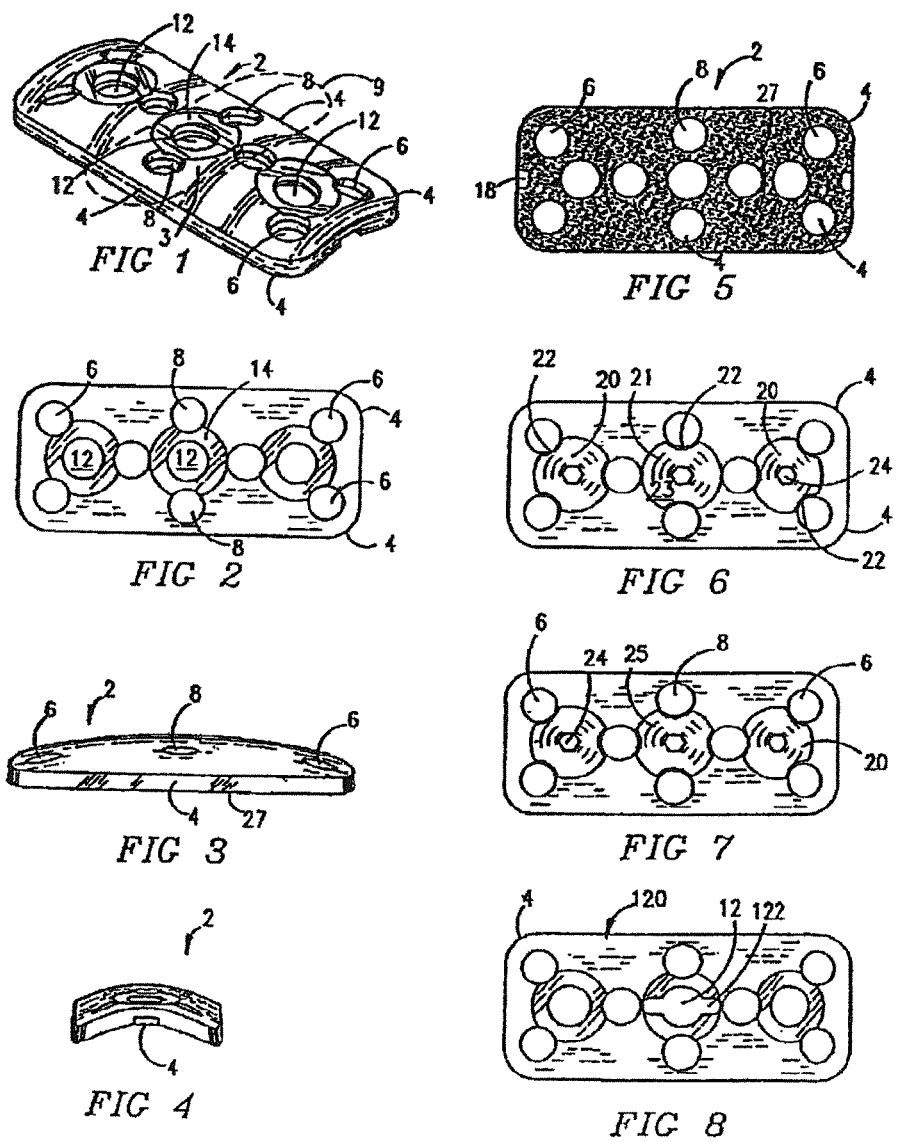

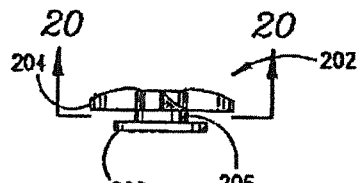
*FIG. 19*
*FIG. 23*
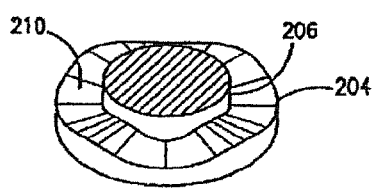
*FIG. 20*
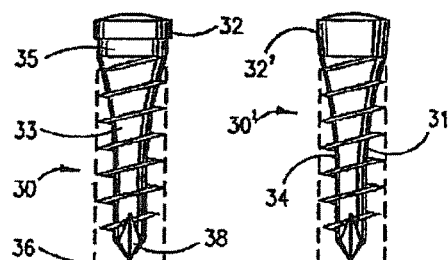
*FIG. 24*   *FIG. 25*
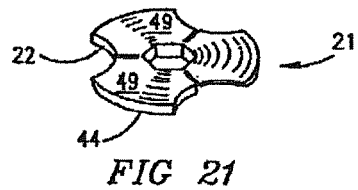
*FIG. 21*
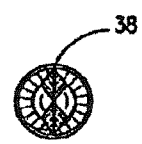
*FIG. 26*
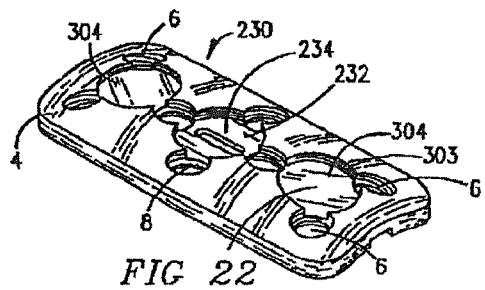
*FIG. 22*
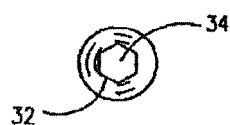
*FIG. 27*

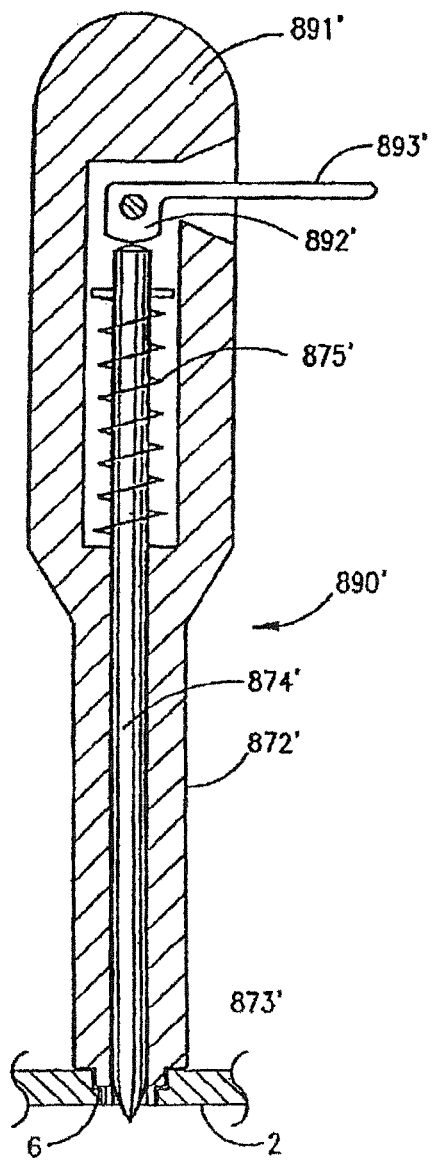
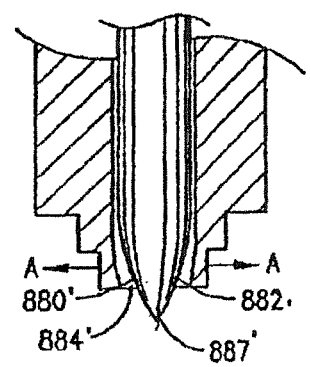
FIG 39D
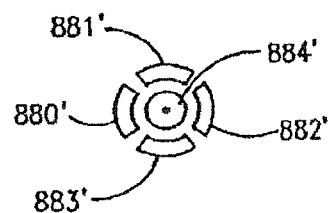
FIG 39B    FIG 39C

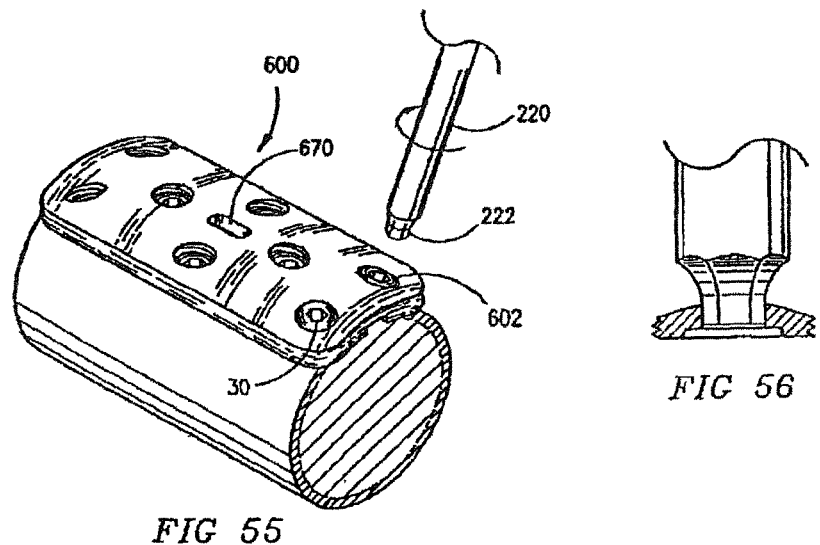
FIG 55
FIG 56
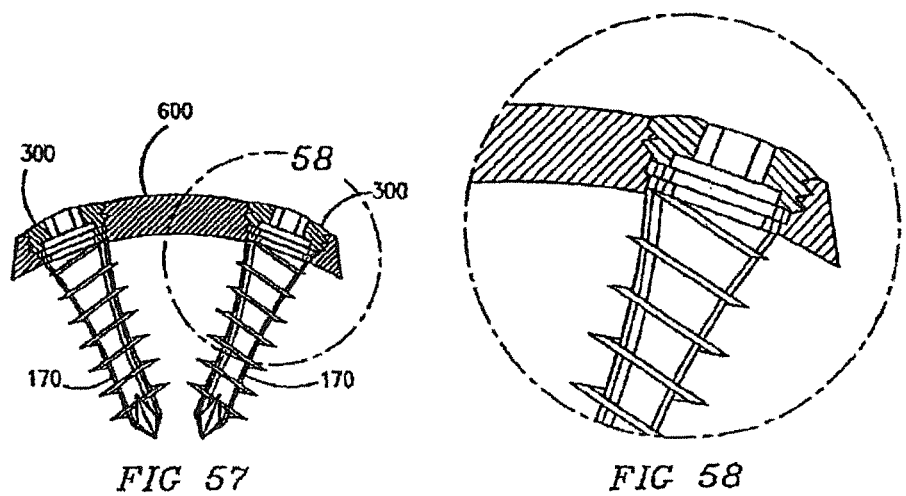
FIG 57
FIG 58

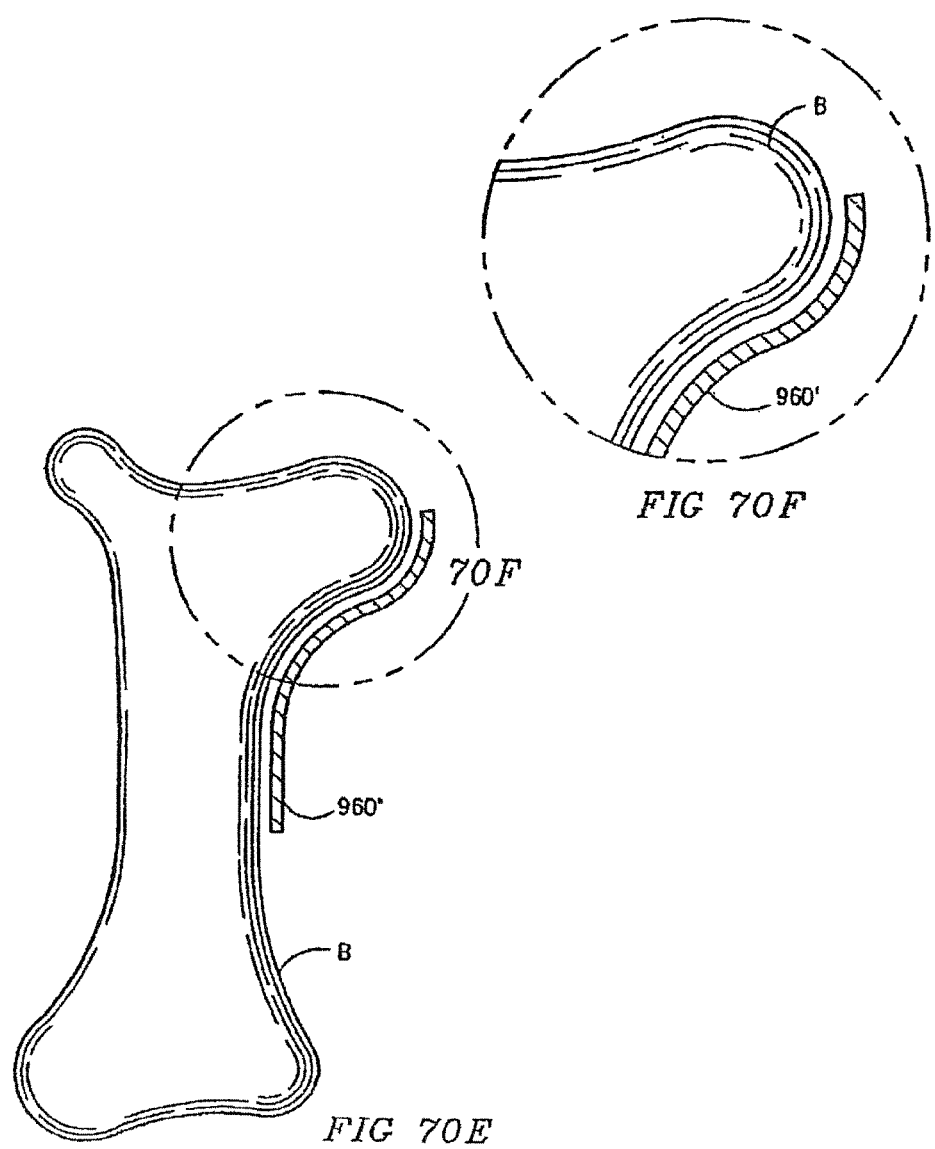

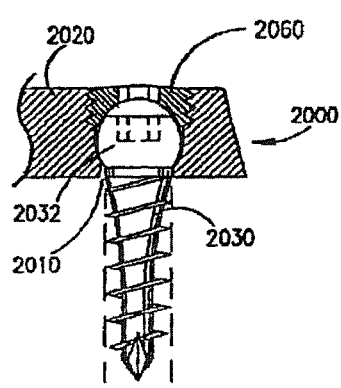
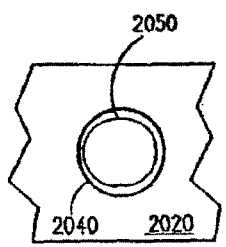
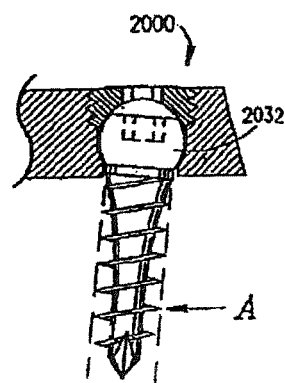
FIG 82　　　　　FIG 83　　　　　FIG 84
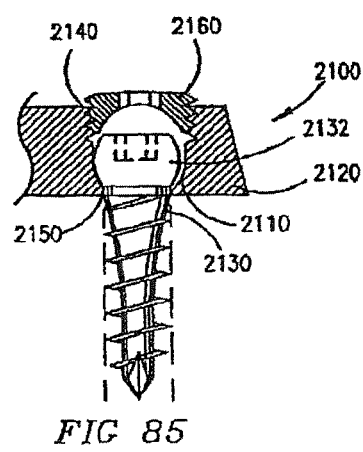
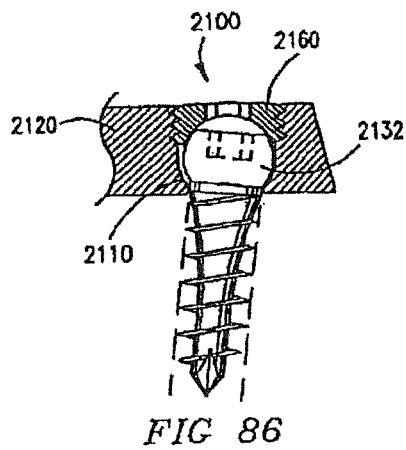
FIG 85　　　　　　　　　FIG 86

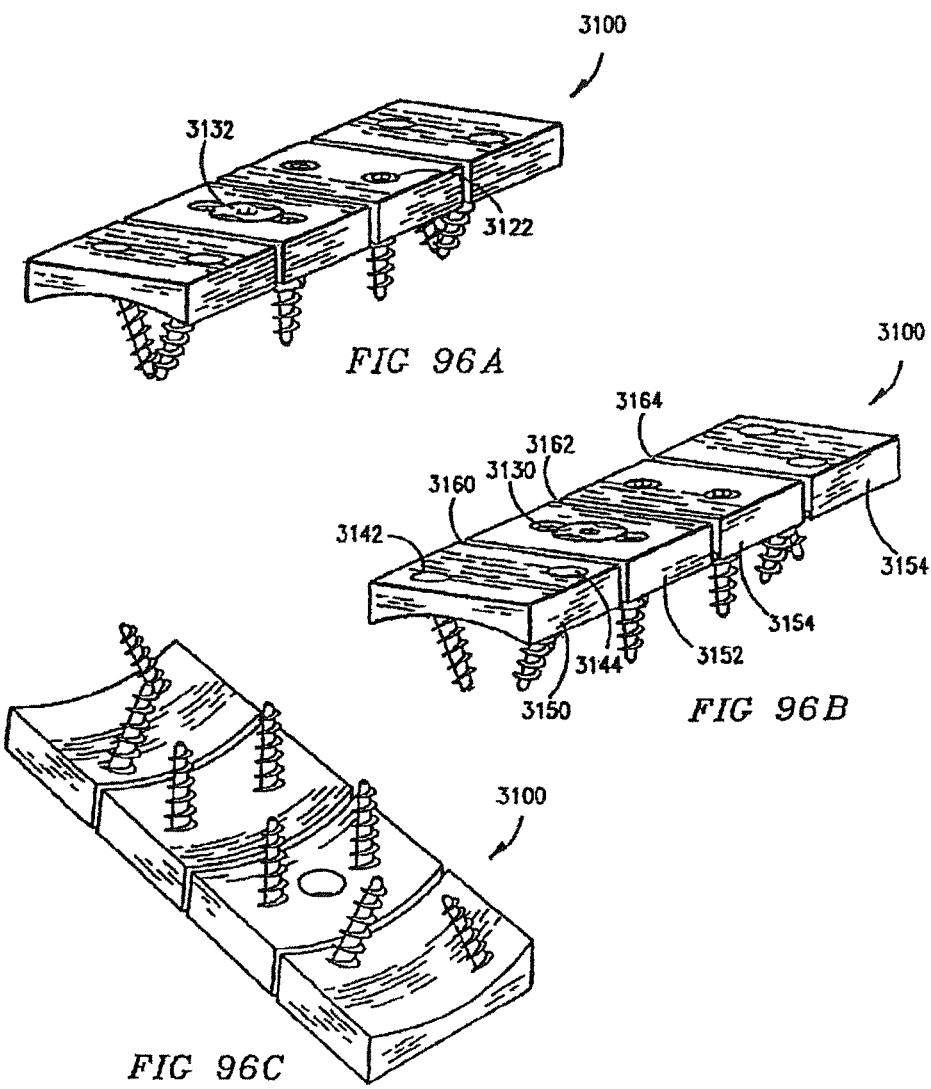

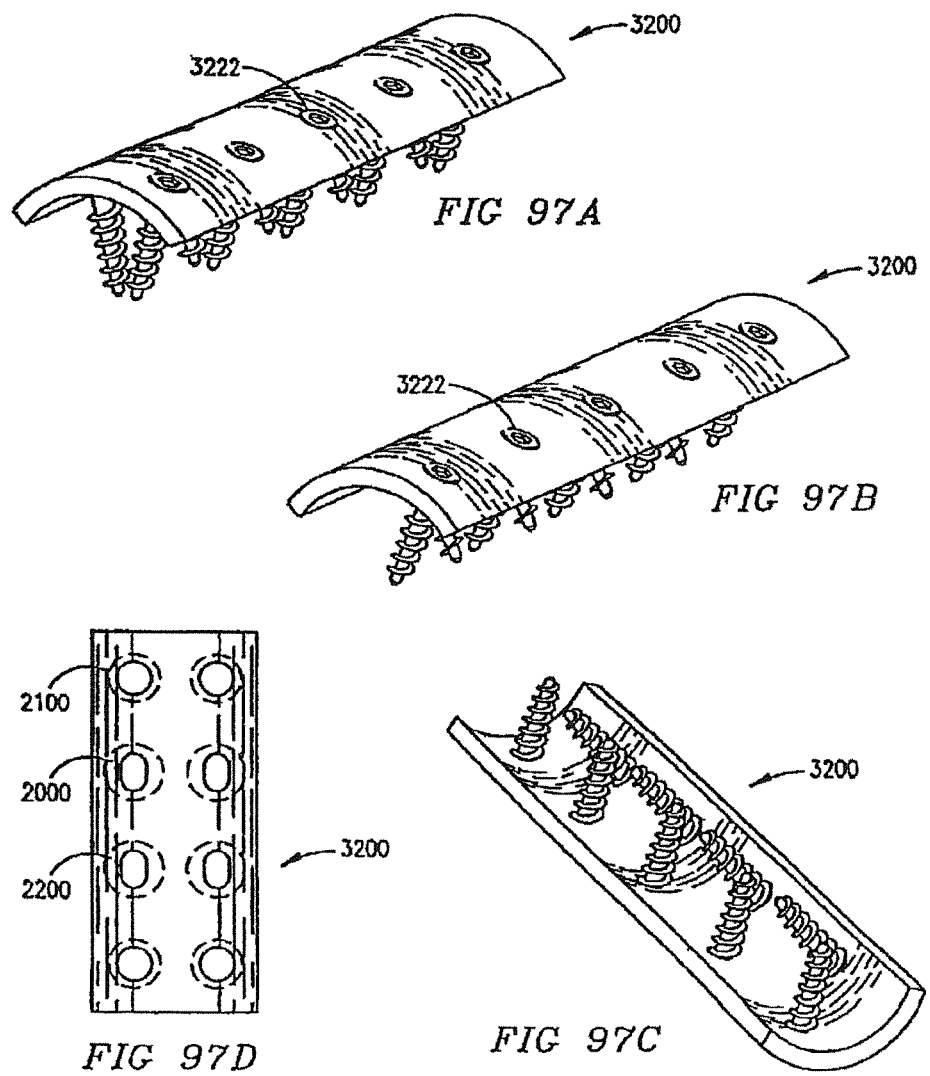

ORTHOPEDIC IMPLANT WITH LOCKING ELEMENT

RELATED APPLICATIONS

This application is a continuation of application Ser. No. 13/406,178, filed Feb. 27, 2012, now U.S. Pat. No. 8,262,708; which is a continuation of application Ser. No. 10/938,380, filed Sep. 11, 2004, now U.S. Pat. No. 8,123,788; which is a continuation of application Ser. No. 10/802,906, filed Mar. 17, 2004, now U.S. Pat. No. 8,048,075; which is a continuation of application Ser. No. 10/098,991, filed Mar. 15, 2002, now U.S. Pat. No. 7,077,844; which is a divisional of application Ser. No. 09/669,912, filed Sep. 26, 2000, now U.S. Pat. No. 6,383,186; which is a divisional of application Ser. No. 09/022,344, filed Feb. 11, 1998, now U.S. Pat. No. 6,139,550; which claims the benefit of provisional application Ser. No. 60/037,139, filed Feb. 11, 1997; all of which are incorporated herein by reference.

BACKGROUND OF THE INVENTION

1. Field of the Invention

The present invention relates generally to skeletal plate systems for aligning and maintaining bone portions of the same bone or of different bones in a selected spatial relationship for healing or fusion of the bone portions, respectively. In particular, the present invention relates to skeletal plating systems comprising a plate that is flat and/or convex over a substantial portion of the lower surface of the plate along the longitudinal axis of the plate, bone screws, and locks for locking the bone screws to the plate; to segmentable plates; crossing screw plates; and combination bone screw-lock-plate systems permitting or causing, intersegmental bone compression and/or shortening.

2. Description of the Related Art

It is current practice in orthopedic surgery to use plating systems for joining portions of a broken bone, or for fusion of portions of separate bones. Such systems are composed essentially of plates and screws for aligning and holding the bone portions in a desired position relative to one another. Plating systems have usefulness in the spine, and have general skeletal use on the flat bones, such as the scapula and the pelvis by way of example, and for use on tubular bones, such as the humerus, ulna, radius, femur, and tibia by way of example.

Problems associated with such plating systems have included hardware breakage, hardware loosening, inability to gain adequate fixation, and distraction pseudoarthrosis where the plate will not allow the bone portions to come together over time resulting in a failure to get solid bone healing. These occurrences may cause problems, be associated with surgical failure, and require further surgical procedures to repair the damage, remove the failed hardware, and/or to reattempt skeletal stabilization.

Plates are usually provided to the surgeon for use in sets having a range of sizes so as to provide for such features as biological variability in size, the numbers of segments to be joined, and the length of the portions of bone to be joined. By way of example, it would be common for a plating system for use on the anterior cervical spine and for joining from two to five vertebrae to comprise of from forty to sixty plates. This requires manufacturers to make a large number of different plates, resulting in increased manufacturing costs and inventory costs and increased costs for hospitals to stock large numbers of plates. Further, in the event that a plate is used and another of its kind is needed before it can be replaced, the ability to provide to a patient the best care could be compromised.

Known plating systems additionally experience problems in connection with those procedures where bone grafts are placed between vertebral bodies to achieve an interbody fusion which heals by a process called "creeping substitution". In this process, dead bone at the interfaces between the graft and the adjacent vertebra is removed by the body, as a prelude to the new growth of bone forming cells and the deposition of new bone. While the plates allow for proper alignment of the vertebrae and their rigid fixation, they can therefore, at the same time unfortunately, hold the vertebrae apart while the resorption phase of the creeping substitution process forms gaps in the bone at the fusion site with the result that the desired fusion does not occur. Such failure in an attempted fusion is known as pseudoarthrosis. A similar phenomenon occurs at the interface of a fractured bone's fragments and is known as non-union. When such a failure occurs, the hardware itself will usually break or become loosened over time requiring further surgery to remove the broken hardware and to again attempt fusion or fracture repair.

Based on a consideration of the features of all of the known plating systems, there remains a need for an improved plating system having the following combination of features:

1) The plate and screws should be sufficiently strong to perform their intended function without mechanical failure;
2) The hardware, and specifically the screws, should be capable of achieving adequate purchase into the bone;
3) Means should be provided for locking each and every bone screw to the plate, and the locking means should be of sufficient size and strength to reliably perform its intended functions;
4) Bone screw locking means should preferably be retainable by the plate prior to bone screw insertion, or should be reliably attachable to a driver to prevent any small parts from becoming loose in the wound;
5) Bone screw orientation should be provided to create maximum screw purchase into bone and high resistance from being dislodged from the bone;
6) An improved and lower cost of production method for the manufacturer of medical plates should be provided;
7) A plate system should be provided for use in various sizes of patients which can be easily made to a selected length by a surgeon to fit the desired application in order to substantially reduce the number of plates required; and
8) Bone screw and plating system should be provided that prevent holding apart of bone portions during the process of creeping substitution and causes, or permits, or both causes and permits the bone portions to move toward each other to permit and promote the fusion or healing of the bone portions.

SUMMARY OF THE INVENTION

The present invention meets the above stated needs by providing various embodiments which are combinable, and may all be utilizable in the same plating system, such embodiments include (1) a skeletal plating system comprising a plate, that is flat over a substantial portion of its lower surface along the longitudinal axis of the plate and/or that has a lower surface that is convex curved along a substantial portion of the longitudinal axis of the plate, bone screws, and locks for locking the bone screws to the plate for skeletal use; (2) a skeletal plating system that permits a pair of bone screws to be inserted into a bone portion in a crossed over orientation and locked in place to the plate; (3) a segmentable skeletal plating system constructed so as to be selected for length by the surgeon; and (4) a combination screw-lock-plating system capable of allowing or urging bone portions together.

1. General Use Skeletal Plating-System a. Multiple Lock System

The plating system of a first embodiment of the present invention comprises a general use skeletal plate having a bottom surface for placement against bone portions, wherein a substantial portion of the bottom surface of the plate is either flat or convex along the longitudinal axis of the plate. It is appreciated that a lesser portion of the lower surface of the plate may be otherwise shaped. The plate of the present invention has a plurality of bone screw receiving holes which extend through the plate, from the upper surface to the lower surface. The plate and its component parts, may be made of any implant quality material suitable for this purpose and suitable for use in the human body, such as, but not limited to, titanium or its alloys. The plate and/or the associated components may be made of a bioresorbable material and may comprise or be coated at least in part with fusion promoting chemical substances, such as bone morphogenetic proteins and the like.

Bone screws are each insertable into a respective bone screw receiving hole for attaching the plate to bone. A locking element, preferably, but not necessarily, in the form of a screw, is engageable in the locking screw hole of the plate and has a head formed to lock at least two of the bone screws to the plate. In the preferred embodiment, the locking elements are pre-installed prior to use by the surgeon in a manner so as to not impede installation of the bone screws into the bone screw receiving holes.

As a result, the problems previously associated with the locking screws of the type applied after the insertion of the bone screws, including the problems of instrumentation to position and deliver to the plate the locking means, backing out, breakage, stripping and misthreading associated with the prior art more delicate locking screws resembling "watchmaker's parts", are eliminated.

b. Single-Lock System

The plating system of the second embodiment of the present invention comprises a single-lock plate for skeletal use having a bottom surface for placement against bone portions, wherein a substantial portion of the bottom surface of the plate is either flat or convex along the longitudinal axis of the plate. The single-lock plate has a locking element that fits within a bone screw receiving hole or into a recess overlapping a bone screw receiving hole to lock a respective one of the bone screws in place. According to this second embodiment of the invention, each of the bone screws is locked to the plate by means of an individual locking element which covers at least a portion of the bone screw. Since in the preferred embodiment of the single-lock plate, no other holes need be formed in the plate to attach the locking elements to the plate, the plate remains quite strong, or alternatively can be made thinner or narrower while keeping the requisite strength for the particular application.

The locking elements can be in many forms to achieve their intended purpose, such as, but not limited to, screws, threaded caps, rivets, set screws, projecting elements, and the like.

In common, neither the single-lock nor the multiple lock plating system requires that the head of the bone screw be hollow, as per some prior known plating systems. It will be appreciated that bone screws are weakened when their heads or head and neck portions are hollow so as to accommodate a second screw at least in part, if not wholly within.

2. Crossing Screw Plating System

In a further embodiment of the present invention, combinable in application with either the multiple lock or the single-lock systems and other novel features herein taught, a plate provides for the crossing over of the shafts of at least a pair of bone screws within a bone portion. A crossed orientation of the screws within the bone provides a more secure engagement of the plate to the bone to which it is to be applied because longer screws may be used and because an area of bone is wedged and trapped between the screws as compared to plates which do not allow paired screws to cross. The use of further screws crossed and/or not crossed in combination with the crossed screw pair can be utilized to trap a still larger section of bone. The plate of the present invention may have multiple bone screw receiving bores (with fixed central longitudinal axes) in which the bores are oriented in a staggered configuration, such that the center points of each of the paired bone screw hole receiving bores are on different transverse lines to permit at least a pair of bone screws to be inserted in a crossed-over configuration within a bone portion. Preferably, the screw bores have defined longitudinal axes in the transverse plane of the plate though the screws may be capable of a variation in positioning as will subsequently be described. In the preferred embodiment, the included angle formed by the shafts of the crossed screws is between 25 to 90 degrees. For spinal use, by way of example, the paired screws are staggered, but are still alignable within the same vertebra so as to be diagonally crossed within that same vertebra and preferably crossed within the posterior two thirds of the vertebral body.

3. Segmentable Plating System

In a further embodiment of the present invention a segmentable plating system is disclosed combinable with the multiple lock and single-lock plating system and the crossing screw teaching, as well as combinable with other novel features herein taught. The segmentable plating system provides a single plate, or a limited set of plates, for aligning and maintaining bone portions in selected spatial relationship in which the plates are manufactured so as to be strong in use, but separable into shorter lengths by the surgeon as needed, thereby eliminating the need to stock a multitude of plate lengths.

By way of example, for application in the spine, an embodiment of the segmentable plating system of the present invention comprises a plate that is capable of spanning multiple segments of a cervical spine and has predetermined separation zones. The separation zones may be positioned in a segmentable plate such that when a portion of the segmentable plate would be applied to the vertebrae, the remaining separation zones in the plate, if any, would be supported by an underlying vertebrae. In use, the surgeon would determine the appropriate plate length needed and if the length needed was less than the length of the provided plate, the surgeon would remove the unneeded portion of the plate at the appropriate separation zone. By way of example, this procedure may be easily performed when the plate is made of titanium or one of its alloys, as the properties of titanium are such that when the plate is bent and then returned to its original position, a clean separation is made at the bend. The parts of the segmentable plates that are being separated can be held to either side of the separation zone to ensure that a precise separation is effected. The separation zones of the segmentable plate, by way of example, may comprise of the plate being scored along its upper, lower, or both upper and lower surfaces. The depth of such scores being dependent on the thickness of the plate, and being sufficient to create surface notchings and a path of least resistance for the plate separation, and yet of limited depth and shape, so as to not weaken the plate so as to render it less than sufficiently strong for its intended use.

By way of example, for application to the anterior aspect of the cervical spine four segmentable plates each having generally a similar length for example sufficient to span five vertebrae (a length of from 80 to 120 mm), and each having different spacings between pairs of bone screw holes could comprise a complete set of plates allowing a surgeon to have all lengths and hole spacings needed to fuse from two to five vertebrae. While the described plates may be separable into a multitude of usable portions, because of regulatory issues involving the identification of each implant with a distinct and singular implant identification number for tracking purposes it may be desirable to configure the plates of the present invention such that each plate will yield only one usable portion, such as is taught in the present invention.

The segmentable plating system of the present invention also has application in reconstructive surgery. For example, during repair of a broken eye socket, the segmentable plating system of the present invention can be used to align and maintain the broken bone portions in correct spatial relationship. The curved characteristic of an eye socket would require the plate used to repair the socket to match the curvature. The segmentable plate of the present invention may be made of a malleable metal, with the malleability of the plate being enhanced by the segmentation of the plate, such that it can more easily be contoured by the surgeon to the appropriate curvature. The correct length of the segmentable plate can also be easily obtained by the surgeon as already described. It should be noted that if for example surgical titanium alloy is selected for the plate material, then the separation zones allow the plate to be more easily bent, but without separating. The present invention makes a virtue of the material property of that alloy in that it may be bent without damage, but fails with surprisingly little force if first bent and then bent back. Back bending is therefore only done for plate separation and is not needed for contouring which requires only primary bending.

The ability to separate a plate into segments also provides significant advantages in the manufacturing process. By way of example, in the process of investment casting, a process commonly used to produce plates. The investment casting cost of material is minor relative to the labor involved in the casting process for the production of each plate regardless of size. It is far more economical to cast one eight inch long plate, which is later separable into four two inch long plates, than to make four two inch castings. If machining is included in production, as from bare stock or stamping or casting, that work can be automated, but the placing of the piece into the machine and securing it (fixturing) generally requires hands on attention, is time consuming, and is a potential manufacturing bottleneck. An eight inch long plate yielding four two inch plates potentially separable at the end by the machine doing the machining, may be fixtured only once. In contrast, the prior art method of manufacturing would require each of the four two inch long plates to be fixtured separately, one at a time. Therefore, the manufacturer can cast one long segmentable plate which can then be separated in the later manufacturing stages to yield multiple plates at an overall lower cost. Similarly, if the plate were in the alternative to be manufactured by machining from solid stock, great labor could be saved by fixturing and securing a single long plate that is later separable into multiple plates rather than having to fixture and secure each of those plates individually.

4. Combination Screw-Lock-Plating System Capable of Intersegmentable Compression and Shortening In a further alternative embodiment combinable with both the single-lock and multiple lock plate designs, the crossed screw teaching, and the segmentable plate teaching as well as other novel aspects of the present invention taught herein, three types of combination screw-lock-plate systems are taught, each capable of intersegmentable shortening and/or compression. Each of the taught systems is designed to counteract and compensate for the lack of contact between bone portions to be joined that may occur as a result of creeping substitution described above. The present invention will allow the vertebrae to move toward an interposed bone graft, and each other if necessary, instead of keeping the vertebrae apart during the occurrence of the resorption phase of the creeping substitution process. Unlike prior art "dynamic" and/or compression plating systems, the present invention may allow for the preservation and/or enhancement of lordosis while otherwise restricting the motion of the bone screws relative to the plate.

The three types of screw-plate-lock systems, which are themselves combinable with one another, are as follows: (1) Passive Dynamic; (2) Self-Compressing; and (3) Active Dynamic and are described below.

a. Locked Passive Dynamic Plating System

As used in this description, the term "locked" means the screws are locked to the plate and can not back out. The term "dynamic" means the screw is capable of movement even though it is locked within the plate to allow bone portions to move closer together. The term "passive" means motion of the screw relative to the plate is allowed, but not caused.

The passive dynamic system allows a bone screw to move relative to the plate even after being locked to the plate when a force is presented against the screw. This system does not cause screw movement, but only allows for movement of the screw to occur and thus is a "passive" system. In a preferred embodiment, motion of the screw relative to the plate is confined to but one direction, that direction permitting bone portions to move closer to one another along the longitudinal axis of the plate.

In the passive dynamic system, a plate having a screw hole passing through the top and bottom surfaces of the plate for receiving a bone screw, may have a round opening at the top of the plate and may have a bottom opening that is oblong-shaped with a length greater than the diameter of a bone screw shaft locatable the screw hole when in use. The head of the bone screw is secured to the plate against backing out and generally against significant linear motion with a locking element, while the shaft of the bone screw is capable of angular motion relative to the plate. The oblong-shaped bottom opening of the screw hole allows the shaft of the bone screw to travel relative to the plate while the bone screw head rotates. The movement of the screw is greatest at the distal end of the screw, allowing for differential shortening of the bone portions being joined. For example, if such a plating system is applied to the anterior aspect of the cervical spine, lordosis (a convex curvature forward of the aligned vertebrae of the neck when viewed from the side) is enhanced when said passive movement occurs.

b. Self-Compressing Locking Plate System

In the self-compressing system, as a bone screw undergoes final tightening, or as it is being locked to the plate with a locking element the bone screw is forced to move in one allowed and desired direction. The bone screw can not move back once it is locked to the plate by the locking element. A purpose of the self-compressing system is to provide a fixed and locked angle of the bone screw relative to the plate for providing compression of bone portions to be joined, such as for example the cervical vertebrae adjacent a disc space, with movement of the bone screw as it is seated to the plate, producing compression and lordosis.

Unlike prior screw systems, the screws are only allowed to move in one direction, that being the direction that would bring bone portions to be joined closer together by angular motion, rather than to produce translational motion of a screw as a whole, without angular change. This induction of a compressive load across bone portions to be joined or fused, induces bone growth and when bone resorption occurs at the interface of the bone portions to be joined, those bone portions are urged to move closer together, thus avoiding the formation of a gap so as to mitigate against non-union or pseudoarthrosis.

The self-compressing system may comprise a plate having a bone screw receiving hole passing through the top and bottom surfaces of the plate with a top opening that is round and has a rounded seat. The bone screw receiving hole has a bottom opening that has a central longitudinal axis that is offset from the central longitudinal axis of the top opening. The bone screw may have a partially rounded head which fits within the upper portion of the bone screw opening and permits movement of the screw head within the top opening in order to provide the appropriate angle for the bone screw shaft with respect to the plate as the bone screw shaft passes through the bottom opening.

Further it is known in the art that compressive forces across the bone further induce bone growth and formation and the present invention teaches novel ways of maintaining bone to bone contact, compressive loading, and even a means for enhancing and increasing the compressive load. A further benefit of the present invention can be appreciated by way of example in regard to use of the present invention on the anterior cervical spine for spinal fusion.

c. Active Dynamic Locking Plating System

In the active dynamic system, a pre-load force is applied to a bone screw such that while the screw may undergo no added motion initially, there is a selective force applied to the screwhead and the screw is capable of motion in only one direction, such that should resorption occur at the interfaces of the bone portions to be joined then the screw is not only free to move in that, and only that direction, but is also urged to do so as it moves to relieve the preload force. Features of these systems may be combined with each other.

By way of example only and not limitation, a plating system may utilize bone screw holes that have a lower surface opening that is oblong and extends from the center aligned to the longitudinal axis of the bone screw receiving bore in a direction for which screw motion is desired. A loading means such as a Bellville washer, lock washer, or other springing means is employed to bear upon the screw head when the screw is locked within the plate from backing out. Such a system urges the bone portions together over time as resorption permits.

For any given use, (plate, screw, hole, and spring) it is simple to determine correct resistance, that being an amount less than would break the bone to which the force is being applied. The Belville-type washer can have a tab which fits into a recess formed within the top opening of the screw hole in order to facilitate proper orientation of the washer or the washer or spring means can be other than round so as to be directionally orientable when placed within the top opening of the screw hole.

When features of these self compressing and active dynamic systems are combined, such a system forces bone portions close upon tightening and then both allows and urges such further motion, as resorption permits over time. The bone screw will only move further in the pre-oriented direction if there is space available and if there is an opposing force present less than the pre-loaded force on the screw.

OBJECTS OF THE INVENTION

It is an object of the present invention to provide an improved plating system which has the above described features and which avoids many of the shortcomings of previously known systems.

It is another object of the present invention to provide a locking mechanism where a plurality of bone screws used for attaching a plate to a bone portion can be easily and reliably locked in place at the same time by a single operation, and wherein the locking mechanisms for locking the bone screws may be pre-installed by the manufacturer prior to the insertion of the bone screws by the physician so that the physician does not have to attach the locking mechanism to the plate as a separate procedure during the operation.

A further object of the invention is to provide plates which are textured or otherwise treated to promote bone growth beneath the plate.

Yet another object of the invention is to provide a system in which the bone screws and locking mechanisms, when fully installed, have a low profile.

It is another object of the present invention to provide for a plating system which may be at least in part bioresorbable.

It is another object of the present invention to provide for a plating system comprising at least in part of bone ingrowth materials and surfaces.

It is another object of the present invention to provide for a plating system comprising at least in part of bone growth promoting substances.

It is another object of the present invention to provide plates with an improved holding ability within the bone due to a locked screw to plate crossover configuration.

It is another object of the present invention to provide a locked plating system capable of selected and specific screw motion so as to accommodate shortening of the bones to be joined.

It is another object of the present invention is to provide means for preventing distraction pseudoarthrosis of the anterior cervical spine, while providing for cervical lordosis.

The above and other objects and features of the invention will become more readily apparent from the following description of preferred embodiments of the invention, provided with reference to the accompanying drawings, which illustrate embodiments of the invention solely by way of non-limiting example.

BRIEF DESCRIPTION OF THE DRAWINGS

FIG. 1 is a perspective view of the first embodiment of a multiple locking plate.

FIG. 2 is a top plan view of the multiple locking plate shown in FIG. 1.

FIG. 3 is a side view of the multiple locking plate shown in FIG. 1.

FIG. 4 is an end view of the multiple locking plate shown in FIG. 1.

FIG. 5 is a bottom view of the multiple locking plate shown in FIG. 1.

FIG. 6 is a top view of the multiple locking plate shown in FIGS. 1-5, with locking elements installed, in an open configuration.

FIG. 7 is a top view of a modification of a plate of FIGS. 1-6 with a four bone screw locking element in place.

FIG. 8 is a top view of a further embodiment of the multiple locking plate of FIG. 1 with an elongated central slot for increased compression capability.

FIG. 19 is a side view of a rivet locking element.

FIG. 20 is a top perspective view of the bottom portion of the head of rivet of FIG. 19 viewed along lines 20-20.

FIG. 21 is a top perspective view of the head portion of a three bone screw locking element.

FIG. 22 is a perspective view of a multiple locking plate formed to utilize locking elements in the form of threaded caps.

FIG. 23 is a side view of a locking element for use with the plate of FIG. 22.

FIG. 24 is a side view of a bone screw.

FIG. 25 is a side view of an alternative form of a bone screw.

FIG. 26 is a bottom view of the bone screws shown in FIG. 24.

FIG. 27 is a top view of the bone screw shown in FIG. 24.

FIG. 39B is a side partial cross sectional view of another embodiment of a plate holder attached to a plate.

FIG. 39C is an end view of the plate holder shown in FIG. 39B.

FIG. 39D is an enlarged fragmentation view of the tip of the plate holder shown in FIG. 39B.

FIG. 55 is a perspective view of a single locking plate installed along a bone with locking caps installed in two bone screw receiving holes.

FIG. 56 is a partial cross sectional view of a locking cap engaged to a driver for installing the locking cap.

FIG. 57 is a partial cross sectional view of the plate, bone screws and locking cap of FIG. 55.

FIG. 58 is an enlarged fragmentary view of area 58 of FIG. 57.

FIG. 70E is a side elevational view of a plate in accordance with the present invention shown applied to a long bone.

FIG. 70F is an enlarged detailed view along line 70F of FIG. 70E.

FIG. 82 is a partial side sectional view of a passive dynamic screw-plate-lock system of the present invention.

FIG. 83 is a top plan view of an opening in the plate shown in FIG. 82.

FIG. 84 is a partial side sectional view of the passive dynamic screw-plate-lock system of FIG. 82 indicating motion in response to a force being applied to the screw in the direction of Arrow A.

FIG. 85 is a partial side sectional view of the self-compressing screw-plate-lock system of the present invention with the lock partially inserted.

FIG. 86 is a partial side sectional view of the self-compressing screw-plate-lock system of FIG. 85 in with the lock fully inserted and the screw seated.

FIG. 96A is a side perspective view of an alternative embodiment of a plate in accordance with the present invention.

FIG. 96B is a top perspective view of the plate in FIG. 96A.

FIG. 96C is a bottom perspective view of the plate in FIG. 96A.

FIG. 97A is a side perspective view of an alternative embodiment of a plate in accordance with the present invention.

FIG. 97B is a top perspective view of the plate in FIG. 97A.

FIG. 97C is a bottom perspective view of the plate in FIG. 97B.

FIG. 97D is a bottom plan view of the plate in FIG. 97B.

DETAILED DESCRIPTION OF THE DRAWINGS

Figure 9:
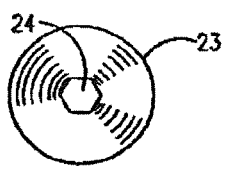
FIG. 9 is a locking element capable of use with the plates of FIGS. 1-6.

In a first embodiment of the present invention a plurality of bone screws are locked to a plate with a pre-installed locking element. This is referred to as the multiple locking plate system. The multiple locking plates will be described, then the locking elements for locking the bone screws to the plate, and then novel bone screws for use with the plates of the present invention. In an alternative embodiment, a single locking element locks a single bone screw to the plate and is referred to as the single lock system.

It is appreciated that the features associated with each of the embodiments of the present invention are not limited to the particular embodiment for which the features are described and are combinable with features described in association with all the embodiments of the present invention.

1. General Use Skeletal Plating-System a. Multiple Locking Plate System

The preferred embodiment of the multiple locking plate 2 according to the present invention is shown in FIGS. 1-5. Plate 2 has a generally elongated form whose outline is generally rectangular. It is recognized that other shapes for plate 2 may be employed. Plate 2 has a bottom surface 27 for placement against bone portions, wherein a substantial portion of bottom surface 27 is either flat or convex along the longitudinal axis of the plate. Plate 2 is for general skeletal use other than in the anterior cervical spine.

As an example only, plate 2 is provided with three locking screw holes 12, each of which in the preferred embodiment is internally threaded 3, and each of which is surrounded by a shallow countersunk region 14. As will be described in greater detail below, in the preferred embodiment, bone screws are inserted in the bone screw receiving holes and a single locking element associated with each of the locking screw holes 12 locks a number of bone screws 30 in position at one time. The locking element may be pre-installed to the plate.

In the embodiment illustrated in FIGS. 1-5, each end locking element 20 will lock three bone screws 30 in place, while locking screw 21 in central locking hole 12 locks two bone screws 30 in place. As shown in FIG. 7, central locking element 25 can also be configured so that four bone screws 30 are locked at one time. Plate 2 may have a thickness appropriate for the strength required for the bone or bones to which it is to be applied and generally in a range from 2 to 8 mm is preferred.

As shown in FIG. 5, at least a portion of bottom surface 27 of plate 2, preferably has a porous, and/or textured surface and may be coated with, impregnated with, or comprise of fusion promoting substances (such as bone morphogenetic proteins) so as to encourage the growth of bone along the underside of plate 2 from bone portion to bone portion. The textured bottom surface 27 also provides a medium for retaining fusion promoting substances with which the bottom surface 27 layer can be impregnated prior to installation. The bottom surface 27 of plate 2 may be given the desired porous textured form by rough blasting or any other conventional technology, such as etching, plasma spraying, sintering, and casting for example. If porous so as to promote bone ingrowth, the bottom surface 27 is formed to have a porosity or pore size in the order of 50-500 microns, and preferably 100-300 microns. Bone growth promoting substances with which the porous, textured bottom surface 27 can be impregnated include, but are not limited to, bone morphogenetic proteins, hydroxyapatite, or hydroxyapatite tricalcium phosphate. The plate 2 may comprise of at least in part a resorbable material which can further be impregnated with a bone growth material so that as the resorbable material is resorbed by the body of the patient, the bone growth material is released, thus acting as a time release mechanism. By having plate 2 itself made from a material that is resorbable and by having bone growth promoting material present permits the bone portions to be joined to do so in a more natural manner as the plate becomes progressively less load bearing thereby avoiding late stress shielding of that bone area.

As further shown in FIGS. 4 and 5, at least one end of plate 2 may have a recess 18 that can cooperate with a compression apparatus.

FIG. 6 is a top plan view of plate 2 of FIG. 1 with locking elements 20, 21 inserted. In the preferred embodiment the locking elements are in the form of screws that cooperate with the threaded interior 3 of the locking holes 12. Each of these locking elements 20, 21 is shown in its initial open orientation, where the orientation of the cutouts 22 in the head 23 of each locking element 20, 21 is oriented so as to permit introduction of bone screws 30 into adjacent bone screw receiving holes 6,8 without interference by the head 23 of the locking element 20, 21.

FIG. 8 is a top view of another embodiment of plate 2 of FIGS. 1-5, and is generally referred to as plate 120. Plate 120 is provided with a longitudinally extending elongated slot 122 along its longitudinal axis which is superimposed on the middle locking hole 12. Elongated slot 122 allows additional relative movement between plate 120 and a compression post 54 associated with a compression tool during a compression procedure.

Figure 15:
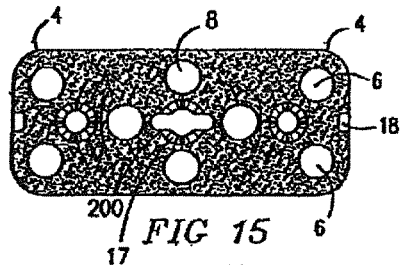
FIG. 15 is a bottom view of the multiple locking plate of FIG. 14.
Figure 14:
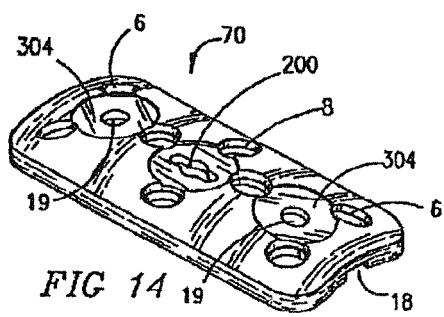
FIG. 14 is a perspective view of an alternative embodiment of cervical spine locking plate using locking rivets.

Referring to FIGS. 14 and 15, an alternative embodiment of a multiple locking plate referred to by the number 70 is shown. In plate 70, rather than the threaded locking hole 12, a central opening 200 for receiving a removable rivet 202, of the type shown in FIGS. 17-20, is provided. FIG. 15 is a bottom view of the plate 70 shown in FIG. 14. The contour of plate 70 is the same as that of plate 2 shown in FIGS. 1-5. The rivet 202 is removable and fits within the unthreaded opening 200, comparable to the locking hole 12 and slot 122 described above. Other embodiments may employ a rivet that is not removable, but is manufactured as part of plate 70 as would be used in the end locking holes 19 of FIGS. 14 and 15.

Referring to FIG. 22, another alternative embodiment of a multiple locking plate is shown and is generally referred to by the number 230. The plate 230 uses threaded caps, such as cap 300 shown in FIGS. 9 and 23, for a locking element or preferably one with cut outs as described herein having an appearance in a top view such as the locking screw element in FIGS. 10-11, for example. The central locking hole 602 has an elongated slot 234 for providing an increased compression capability, if desired.

Figure 10:
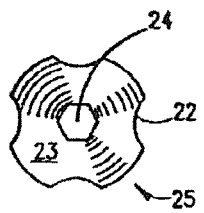
FIG. 10 is a top view of a locking element for use with the central opening of the plate of FIGS. 7 and 22.
Figure 11:
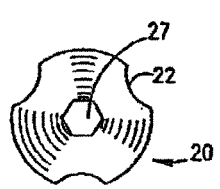
FIG. 11 is a top view of a locking cap for use in the end openings shown in FIGS. 1, 6 and 7.
Figure 16:
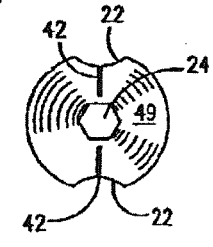
FIG. 16 is a top view of a preinstallable two bone screw locking element.

Referring to FIGS. 10-13, a first embodiment of locking elements 20, 21, and 25 in the form of locking screws according to the present invention for use with plate 2 are shown. FIG. 10 is a top plan view illustrating the head 23 of the central locking element 25 shown in FIG. 7. The shaft 46 of locking element 25 is threaded 47 to mate with the threading 3 within the associated locking hole 12 of plate 2. As shown in FIG. 21, each segment 49 on each side of cutouts 22 of the locking element 21 has a bearing surface 48 formed at the lower surface of locking element head 23. As shown in FIG. 16, the locking element head 23 can be provided with two slits 42 for providing flexibility to the locking element head 23 to assist in the locking element's ability to ride over the top of the bone screw head 32 during the locking action when the locking element is rotated.

Referring to FIGS. 6 and 10-13, it will be appreciated that when the locking elements 20, 21 are rotated in the clockwise direction with respect to the view of FIG. 6, a respective bearing surface 48 will ride upon the curved top surface 39 of a respective bone screw head 32 in order to positively lock the associated bone screws 30 and the locking elements 20, 21 in place. This bearing feature can be used with the other locking elements described herein. Similarly, the bearing surface of the locking elements 20, 21, 25 can be also cammed.

Figure 12:
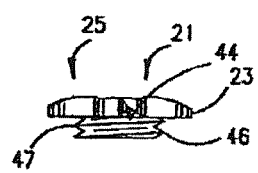
FIG. 12 is a side view of the locking element of FIG. 16.
Figure 13:
FIG. 13 is a side view of another embodiment of the locking element of FIG. 16.
Figure 17:
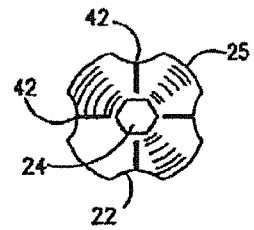
FIG. 17 is a top view of an alternative embodiment of a four bone screw locking element having head slots for increased flexibility of the locking tabs.

Alternatively, as shown in FIGS. 12 and 13, in place of a flat bearing surface 48, a ramp or wedge shaped surface 44 may be used to increase the force applied to the bone screw head 32. In an alternative embodiment cam design when locked, the leading end of the ramped portion 44 of locking element 21 would be lower than the prominence of the bone screw head 32 so that more force is needed to lift the locking element 21 and untighten it than is needed for the locking element 21 to remain tight and locked. However, the locking element head 23 need not have slits, be cammed or have a ramped surface to achieve the locking of bone screw 30 in place. Pressure, friction, interference fits, or other engagement means capable of preventing the locking element from moving from its locked position may be employed.

Figure 18:
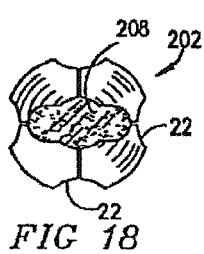
FIG. 18 is a bottom view of the rivet type locking element for use with the central opening of the plate of FIG. 14.

Referring to FIGS. 17-20 a rivet 202 intended for use in association with plate 70 of FIGS. 14-15, is shown and is also shown in detail in cross section in FIGS. 19 and 20. Rivet 202 has a head 204, a shaft 206, and an elongated bottom segment 208 for fitting within the corresponding opening 200 in plate 70. The lower surface 210 of the head 204 of the rivet 202 has a bearing surface, such as on the bottom of locking element 20, 21, for engaging the top surface 39 of the bone screw head 32. For use in the end locking holes 19, the upper surface of the elongated bottom segment 208 can have a camming surface for cooperating with the camming surface 17 of the bottom of plate 70 to hold the rivet 202 in the locked position against the bone screw head 32, as shown in FIG. 15. While the rivet of FIG. 18 is a separate, removable component from the plate, the rivets, and particularly those for use with the end locking holes, can be formed as part of the plate during the manufacturing process of the plate and rivet can be non removable if so desired. The bearing surface of the rivet 202 may also be cammed to prevent the rivet from unlocking once the cammed portion passes over the screw head.

Each of the above embodiments provides tight attachment of the locking element relative the bone screw 30 and relevant plate.

In the alternative embodiment of multiple locking plate 23 shown in FIG. 22, the locking element can be in the form of threaded locking cap 300 shown in FIG. 23. The threaded locking cap 300 has a thread 302 on its outer circumference corresponding to the thread 303 on the inner circumference of the locking element depressions 304 in the top of plate 230 shown in FIG. 22. The locking cap 300 is relatively thin, particularly compared to its width. The top 305 of locking cap 300 may be provided with a noncircular recess or through hole 306 for receiving a similarly configured driving tool or employ other tool engaging means.

Figure 28:
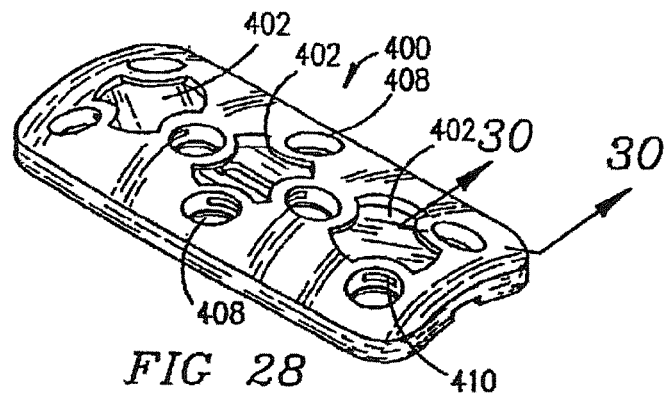
FIG. 28 is a top perspective view of a fourth embodiment of a multiple locking plate.
Figure 29:
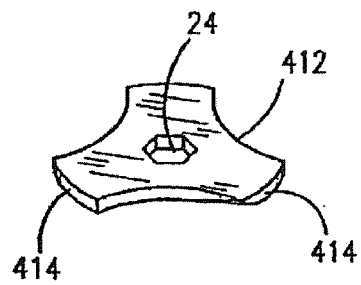
FIG. 29 is a perspective view of locking element for use with the plate of FIG. 28.
Figure 30A:
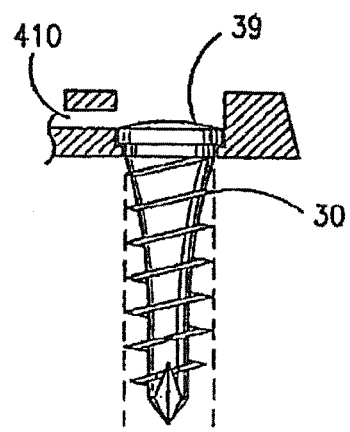
FIG. 30A is a partial side sectional view of the plate of FIG. 28 along lines 30-30 with a bone screw in place.

Referring to FIGS. 28, 29, and 30A another embodiment of the multiple locking plate generally referred to by the number 400 and a locking element in the form of a thin locking member 412 are shown. Plate 400 has an opening in its top surface for insertion of the thin locking member 412, a recess 402 associated with each of the bone screw receiving holes 408 and a slot 410 in the side wall of the bone screw receiving holes 408 to permit the thin locking member 412, having a series of thin projections or blades 414, thinner than the slot 410, that give this locking member 412 an appearance similar to that of a propeller. The thin locking member 412 is able to be rotated within the plate so as to not cover the bone screw holes, thus allowing the thin locking member 412 to be pre-installed prior to the installation of the bone screws by the surgeon. Limited rotation of the thin locking member 412 allows the blades 414 to protrude through the slot 410 and to cover a portion of the top of the associated bone screws 30. The blades 414 of the thin locking member 412 are flexible and, when rotated, slide over the top surface 39 of the bone screw head 32 to lock the bone screw 30 in place. As with the other embodiments discussed, each of the embodiments of the locking element is capable of locking more than one bone screw 30. It is appreciated that the various multiple locking plates and locking element combinations are capable of locking as many as four bone screws at once, but are equally effective for locking a lesser number or none at all, that is securing itself to the plate.

It will be noted that one characteristic of each of the above described locking element embodiments is to have a driver engagement means, in these cases for example, a recess 24 as large as the recess 34 in the bone screws 30 so that the same tool can be used to turn both the bone screws 30 and the locking elements. Also, the locking elements are sufficiently strong and have sufficient mass so as to be able to withstand being locked without breakage.

Figure 30B:
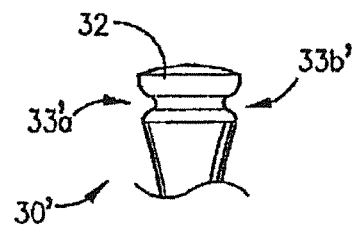
FIG. 30B is an alternative embodiment of the bone screw of the present invention.
Figure 31A:
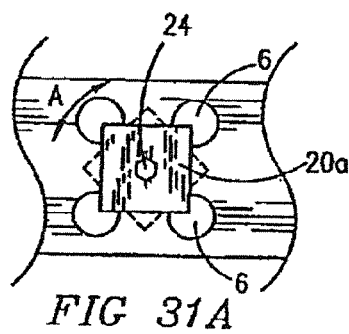
FIGS. 31A-31E illustrates top plan views of alternative embodiments of the multiple locking elements of the present invention.
Figure 31B:
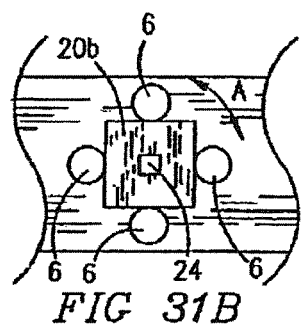
Figure 31C:
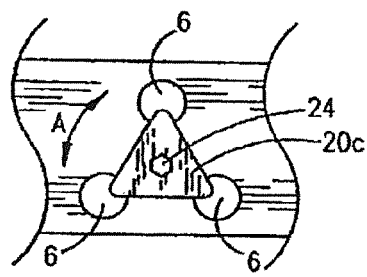
Figure 31D:
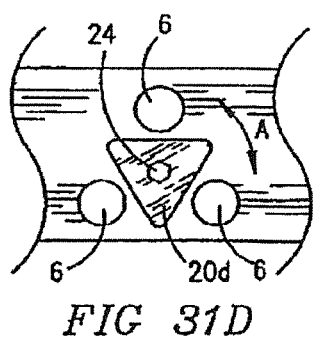
Figure 31E:
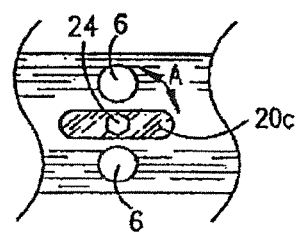

Referring to FIG. 30B an alternative embodiment of the bone screw 30 of the present invention is shown. Bone screw 30' is a variable angle screw having a head 32' with a rounded top and has neck below the head 32' with relieved portions 33'a and 33'b to allow universal motion of the bone screw 30' within the bone screw receiving hole of a plate as the relieved portions provide clearance for the screw to move. In one embodiment, bone screw 30' may be secured to the plate by a locking element that prevents the screw from backing out, but allows the locking element to bear down on the top of the screw head 32' still move relative to the plate. Alternatively, the bottom surface of the seat of the bone screw receiving hole and the bottom of the screw head 32' may be roughened to provide some resistance to movement of the screw head 32' within the bone screw receiving hole and/or the lock may bind the screw head with sufficient force such that once the lock is tightened no movement of the screw within the plate is possible.

The above-described examples of the multiple locking elements have a number of cutout portions having an arc with a radius greater than that of the bone screw head. However, it is appreciated that preinstallable multiple locking elements can have a configuration without any cutout portions and still permit for clearance of the bone screw head. Some examples of such locking elements are shown in FIGS. 31A-31D in which alternative embodiments of locking elements 20a-20d without cutout portions and in which the bone screws can be installed into the bone screw receiving hole 6 even when the locking element is pre-installed to the plate. The locking elements may be rotated in the direction of arrow A to bear upon at least a portion of the screw head to lock the bone screws to the plate.

Figure 33:
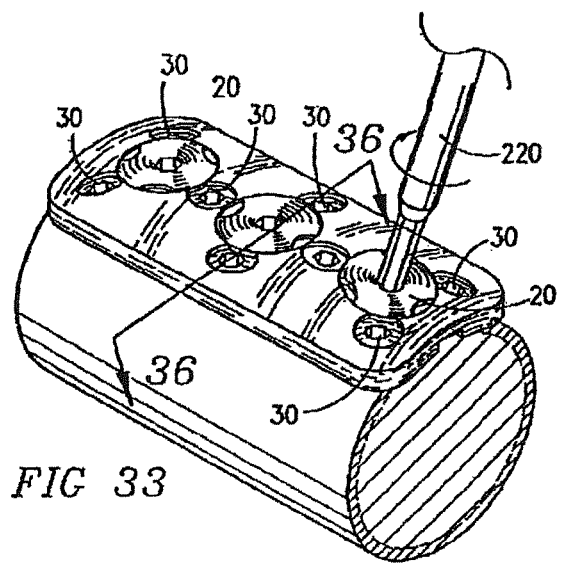
FIG. 33 is a perspective view showing the locking of the bone screws to the plate.
Figure 34A:
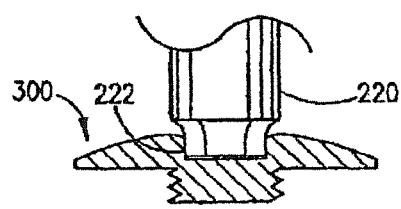
FIG. 34A is a partial side sectional view of a shielded locking element attached to a driver instrument.
Figure 34B:
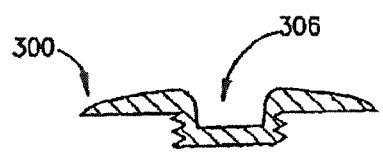
FIG. 34B is a partial side sectional view of an alternative embodiment of a locking element.
Figure 35:
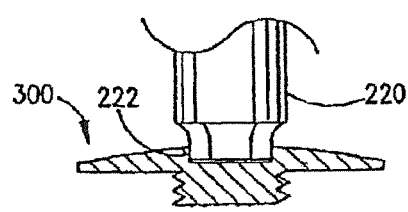
FIG. 35 is a partial side sectional view of another embodiment of the locking element.

In addition, the head 23 of each locking element 20, 21 is provided at its center with a noncircular recess 24, such as shown in FIG. 9 which is engageable by an appropriate manipulation tool, such as shown in FIGS. 33-35. In the embodiment of head 23 shown in FIG. 9, the associated tool would have a hex head, it is appreciated that other shapes of recesses in the head 23 may be used or other male or female driver engaging means may be used without departing from the scope of the present invention. The thread of each locking hole 12 and of each locking element 20, 21 has a close tolerance so that they will reliably retain their orientations so as to permit introduction of bone screws 30 into bone screw receiving holes 6, 8 without interference. Alternatively, the threads can be slightly mismatched or a thread or threads can be made irregular or imperfect.

Figure 71:
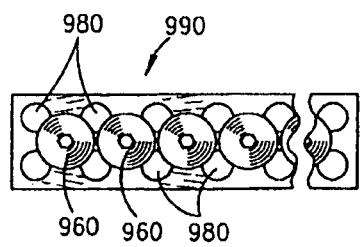
FIG. 71 is a top plan view of a further embodiment of the multiple locking plate for use in stabilizing multiple segments of the spine or portions of a long bone.
Figure 72A:
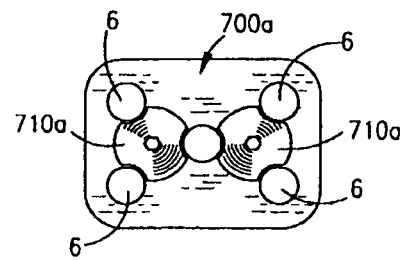
FIGS. 72A-72H are top plan view of various embodiments of multiple locking plates of the present invention.
Figure 72B:
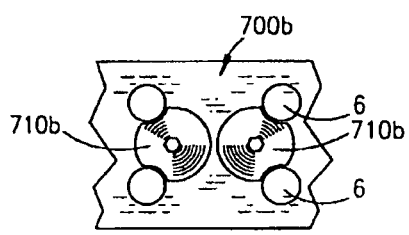
Figure 72C:
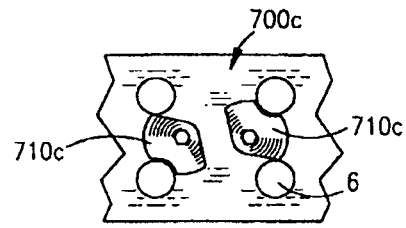
Figure 72D:
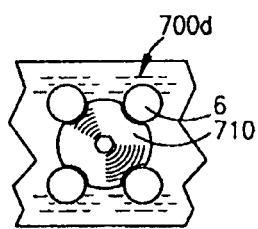
Figure 72E:
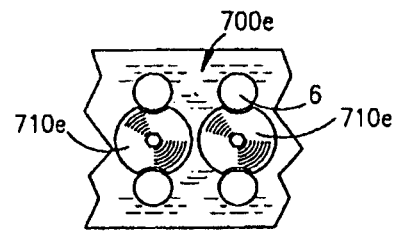
Figure 72F:
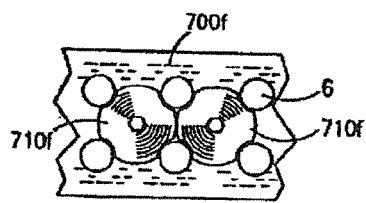
Figure 72G:
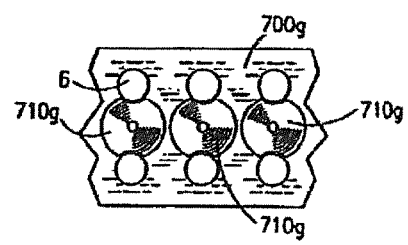
Figure 72H:
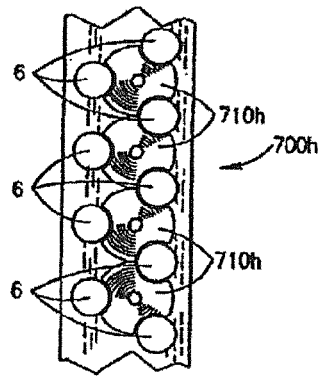

It is appreciated that while various forms of locking elements have been disclosed, in light of the teaching, other equivalent means can be used for the purpose of locking the bone screws 30 in place. In FIG. 71, an alternative multiple locking plate 990 is shown having additional intermediate bone screw receiving holes 980 and, associated locking elements 960 for locking the bone screws 30 in place.

In FIGS. 72A-72H various plates 700a-h are shown. Each of these plates 700a-h have bone screws inserted through the bone screw receiving holes 6 and then locked in place. As shown in FIGS. 72A-72H, one locking element 710, or two locking elements can be used to lock four bone screws in place. In FIGS. 72A-72H, each of plates 700a-h is shown with the locking elements in their open orientation, before being rotated to lock the bone screws. Plates 700a-700h each have locking elements 710 for locking bone screws inserted into bone screw receiving hole 6 of the plate.

FIG. 24 provides a side view of one embodiment of a bone screw 30 according to the present invention. Bone screw 30 has a bone screw head 32, a shaft 33, and a tip 36. FIG. 27 is a top view of the bone screw 30. At the center of bone screw head 32 is a profiled recess 34 which may have the same form as the recess 24 of each locking element 20, 21 in which case it may be turned with the same tool as that employed for turning locking elements 20, 21. It is appreciated that the driver engaging portion of the bone screw 30 could be slotted, and be either male or female.

In the embodiment of bone screw 30 shown in FIG. 24, the bone screw head 32 is stepped, with the first lower head portion 35 being contiguous with the screw shank 33 and has a smaller diameter than the upper portion of the bone screw head 32. Preferably, but without limitation, when this embodiment of bone screw 30 is employed, each bone screw receiving hole 6, 8 of plate 2 has a countersunk region 14 matching the diameter of the upper portion of the bone screw head 32 and dimensioned for an interference fit. The lower portion 35 of the bone screw head 32 is dimensioned to achieve an interference fit with its associated portion of bone screw receiving holes 6, 8. The larger diameter upper portion of bone screw head 32 assures that the bone screw 30 cannot be advanced completely through bone screw receiving holes 6, 8 of plate 2. The bone screw 30 passes completely through the upper surface of plate 2 without engaging the upper surface in any way.

Figure 37:
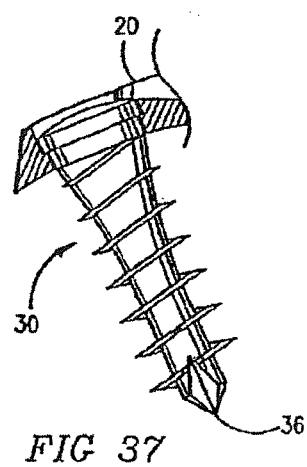
FIG. 37 is an enlarged portion of detail along line 37 of FIG. 36.

As shown in FIG. 37, preferably, but without limitation, the head 32 of screw 30 passes unobstructed through the upper surface of the plate until the lower surface of enlarged screw head 32 engages the upper face of the narrowed bone screw receiving portion at the midsubstance or below the midsubstance of the plate. This is considered optimal for allowing for the greatest screw to plate stability, even absent the lock, against all forces except those reverse the path of insertion, while still providing for the greatest plate strength beneath the bone screw head 23. A sheer vertical circumferential wall is best able to constrain the motion of a screw, if the head is similarly configured and there is little tolerance between them. Placing the support of the head near the mid thickness of the plate is preferred as it allows the upper head to remain large to accommodate the recess for the driver without being weakened, while placing the support of the head away from the upper surface of the plate allows the screw head to be deep into the plate. Placing the support of the head at approximately the mid thickness of the plate assures plenty of plate material beneath the head to support while providing adequate head length above and below the contact point to prevent the contact point from acting as a fulcrum by providing adequate lever arms to prevent unwanted motion.

In the alternative embodiment of bone screw 30', as shown in FIG. 25, bone screw head 32' is tapered in the direction from the top of the bone screw head 32' toward screw tip 36'. Again, the bone screw head 32' is dimensioned to achieve an interference fit in the associated bone screw receiving hole 6,8 when the bone screw 30' has been fully installed. When this embodiment of bone screw 30' is employed, bone screw receiving holes 6, 8 need not be provided with a countersunk region 14.

In each of the above embodiments of the bone screws, the bone screws 30 and 30' present a unique combination of a tapered screw shaft 33 and a helical thread 31. The diameter of screw shaft 33 generally increases from a distal portion of the shaft near the screw tip 36 toward proximal portion of the shaft near screw head 32. In the preferred embodiment, the rate of increase in diameter is also greater near the bone screw head 32. Such a shape avoids stress risers and provides increased strength to the screw at the screw-plate junction, where it is needed the most. The tapering of screw shaft 33 may have a concave form, as shown in FIG. 24, or may be linear. The distal portion of the screw shaft 33 may assume a constant diameter.

The thread 31 of the bone screw 30 has a substantially constant outer, or crest, diameter "d" from below the bone screw head 32 to near the bone screw tip 36. In the screw tip 36, the crest diameter of thread 31 may be reduced for preferably one to two turns to facilitate the insertion and penetration of the bone screw 30 into the bone.

In the preferred embodiment, the thread 31 of each bone screw 30 has an outer diameter slightly smaller than the diameter of the lowest portion 35 of the bone screw head 32, which is adjacent the trailing, or upper, end of the associated thread 31. In addition, the thread 31 is relatively thin, in the direction of the longitudinal axis of the screw, and tapers outwardly, and has a cross section of a triangle, though the sides need not be straight.

Figure 38:
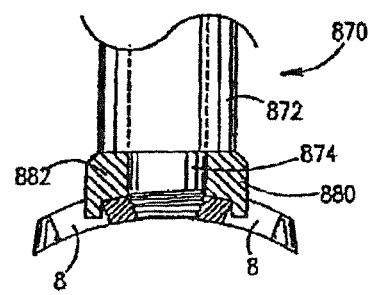
FIG. 38 is a side partial cross sectional view of a plate holder attached to a plate.

As shown in FIG. 38, plate holder 870 has a hollow tubular housing 872, with a central rod 874 having a thread 878 at one end for engaging one of the threaded locking holes 12 in plate 2. The bottom end of the housing 872 has projections 880, 882 that extend outwardly and then downwardly to fit into the bone screw receiving holes 8 of plate 2 preventing the housing 872 from rotating. The central rod 874 is located in the housing 872 such that it can be rotated by rotating a handle (not shown) which is fixed to the central rod 874 at its upper end.

Figure 39A:
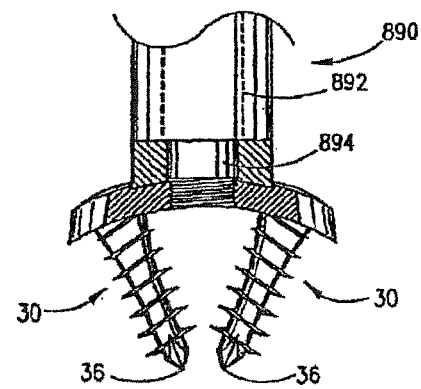
FIG. 39A is a side partial cross sectional view of another embodiment of a plate holder attached to a plate.
Figure 40:
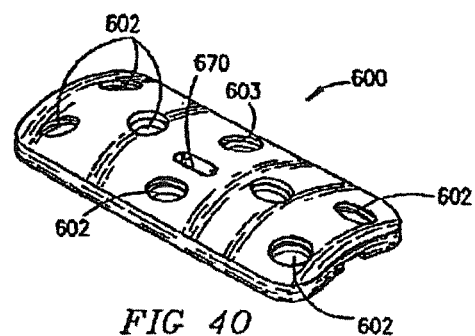
FIG. 40 is a top perspective view of an embodiment of a single locking plate.

In FIG. 39A an alternative embodiment of the plate holder 890 is shown. A single solid member 890 has a threaded projection 894 at its bottom end for attachment to the central threaded locking hole 12 in the plate. The bottom surface of the holder 890 of this embodiment is contoured so as to match the contours of the top surface of the plate adjacent to the locking hole 12, shown as a depression 14.

Referring to FIG. 39B-39D, an alternative embodiment of the plate holder 890' is shown. Plate holder 890' has a hollow tubular housing 872' having a handle 891' at its top end and a bottom end 873' configured for insertion into a bone screw receiving holes 6 of a plate. A rod 874' having a sharp tip 875' is contained within housing 872' and is spring biased by a spring 875'. A lever 893' is provided for advancing rod 874' from within housing 872'. Lever 893' has a cammed portion 892' to lock rod 874' in position.

The bottom end of the housing 872 is slitted to form projections 880, 881, 882, and 883' that are moved outwardly by the shaft of rod 872' above tip 875' in the direction indicated by arrow A when rod 874' is advanced from within housing 872' to engage and lock into the bone screw receiving holes 6 of plate 2 preventing the housing 872' from separating from plate 2. In this manner the plate holder 890' functions as both a holder for a plate and also as a temporary plate fixation device to hold the plate in the correct position to the bone prior to the insertion of the bone screws. Further, holder 890' can be used to form pilot holes for screw insertion into the bone portions.

Figure 32B:
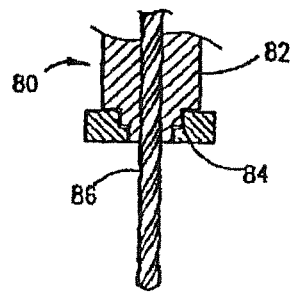
FIG. 32B is an alternative embodiment showing a cross-sectional view through the plate with a drill guide to guide a hole forming instrument.
Figure 32C:
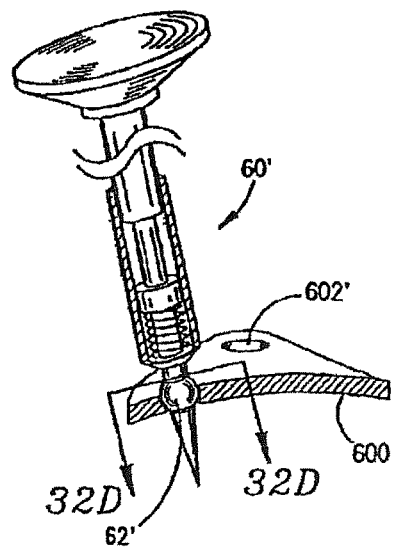
FIG. 32C is an elevational, cross-sectional detail view of a portion of an alternative embodiment of a bone forming device engaged to a portion of the plate of the present invention.
Figure 32D:
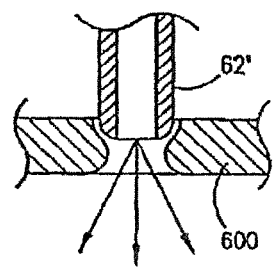
FIG. 32D is a cross-sectional view along line 32D-32D of FIG. 32C.
Figure 32A:
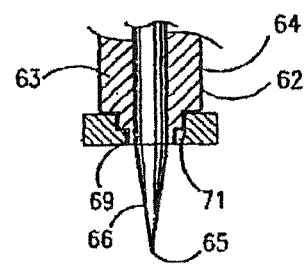
FIG. 32A is an elevational, cross-sectional detail view of a portion of the bone forming device engaged to a portion of the plate of the present invention.

Certain structural features of hole forming apparatus 60 are shown in greater detail in FIG. 32A. In particular, it can be seen that the bottom end of housing 62 has a projecting portion 69 dimensioned to fit precisely in a bone screw receiving hole 6 or 8 of plate 2. The bottom 71 of the projecting portion 69 is flat in a plane perpendicular to the axis of housing 62. When the projecting portion 69 of housing 62 is snugly inserted into a bone screw receiving hole 6, 8 and the flat bottom 71 is placed flush against the upper surface of plate 2, it is assured that the leading end 66 of shaft 64 will form a pilot hole in the vertebral bone having an axis perpendicular to the plane of the associated portion of plate 2, thereby assuring that the bone screw 30 will be subsequently installed so that its axis is also perpendicular to the plane which is parallel to the upper and lower surfaces of the associated portion of plate 2.

When a plate is used which has a threaded bone screw receiving hole, the lower end of the pilot hole forming apparatus 60 is threaded so as to engage the thread in the bone screw receiving hole 6, 8 thereby fixing the plate and the pilot hole forming apparatus together, assuring a stable fit between the pilot hole forming apparatus and plate 2. It should be noted that the diameter of the leading end 66 of the shaft 64 is small since it has to fit within the small space left between the inside wall of the pilot hole forming apparatus. Since it is only a pilot hole for a self tapping bone screw 30 that is being formed, the small diameter is satisfactory.

Referring to FIG. 32B, if for any reason it should be desired to form the pilot hole in the bone 50 by drilling, rather than by the use of the pilot hole forming apparatus 60, use can be made of a drill guide 80, having a lower end as shown in FIG. 32B. The drill 80 guide consists of a tubular member 82 and a small diameter lower end 84 which is dimensioned to achieve a precise interference fit in the associated bone screw receiving hole 6, 8 of plate 2. Along the small diameter lower end 84, drill guide 80 has an axial end surface in a plane perpendicular to the longitudinal axis of the drill guide 80 so that when the small diameter portion 84 is fitted into the bone screw receiving hole 6 and the surface surrounding the small diameter portion 84 is flush against the upper surface of plate 2, the axis of the drill guiding bore 86 in drill guide 80 will be precisely perpendicular to the upper and lower surfaces of the associated portion of plate 2. As with the case described above, the bottom end of the drill guide 80 can be threaded so as to engage to the threaded opening of plate 2.

Referring to FIGS. 32C and 32D, an alternative embodiment of hole forming apparatus 60' is shown. Hole forming apparatus 60' is similar to hole forming apparatus 60, except that it has a ball end 62' that fits within bone screw receiving hole 6. As shown in FIG. 32D, the ball end 62' may be oriented at any angle relative to the plate for angular hole formation into the bone. Hole forming apparatus 60' provides for variable angle preparation of the pilot holes for the bone screws relative to the plate.

After the bone screw receiving holes 6, 8 are formed in the bone 50 through the upper two bone screw securing holes 6 of plate 2 by means of either hole forming apparatus 60 or drill guide 80, bone screws 30 are threaded into the bone 50 while holding plate 2 firmly against the bone 50 with plate holder 800.

FIG. 33 is a perspective view showing plate 2 of FIGS. 1-5, at a stage of a surgical procedure when bone screws 30 have been fully installed in bones or pieces of the same bone, and locking screws 20, 21 have been rotated to lock three bone screws 30 in place; the left-hand locking screw 20 as viewed has been rotated through an angle of about 45° to lock three bone screws 30 in place and the central locking element 21 has been rotated through an angle of about 90° to lock two other bone screws 30 in place. At this time, one of the bearing surfaces 44 of each locking element 20, 21 rests atop the screw head 32 of a respective bone screw 30. Ideally locking elements 20, 21 are provided to the user almost fully tightened, but in the open position such that bone screws can be inserted. Full locking of the bone screw requires 90° or less of turning of the locking element and often 45° will suffice to lock the bone screws.

Installation of the multilock locking element 300 can also be performed with a tool 220 such as shown in FIGS. 34A and 35 having a suitably shaped tip 222 with a length corresponding to the depth of hole 306 in a locking cap 300. The end 222 of tool 220 is flared just proximal to the most distal end so that it creates a friction fit with the screw cap 300 for ease of manipulation, and prevents the locking element 300 from falling off the tool 200. As shown in FIG. 34B, in the alternative, the tool receiving hole 306 can be flared to cooperatively engage a tool having a tip with a corresponding configuration.

Figure 36:
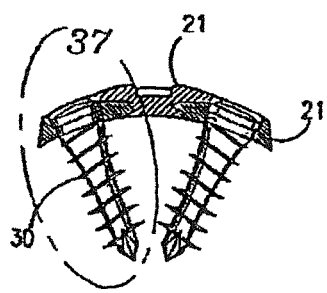
FIG. 36 is a partial cross-sectional view showing a plate, locking element and bone screws along lines 36-36 of FIG. 33.

FIG. 36 is a cross-sectional view in the plane of the center of the two end locking screw holes 6 of plate 2, with two bone screws 30 in their installed positions and locking element 21 in its locking position. FIG. 37 is an enlarged view of one of the bone screws 30 in plate 2 of FIG. 36. In a preferred embodiment, the axis of each screw 30 is generally perpendicular to tangents to the upper and lower surfaces of plate 2 at points which are intersected by the longitudinal axis of the associated bone screw 30. Thus, because of the curvature of plate 2 in the plane of FIG. 36, bone screws 30 can be directed so as to converge toward one another at a desired angle. The axis of the two bone screws 30 shown in FIG. 36 may subtend an angle sufficient to cause the paths of bone screws in the same plate to cross within the substance of the bone. Alternatively, the curvature of the plate from side to side may be so as to conform to the surface of the bone to which the plate is being applied and the axis of the paired screw hole may deviate from being perpendicular to the plate when viewed on end to achieve the optimal convergence.

Because the bone screws 30, once inserted, are locked to the plate, a "claw" of a rigid triangular frame structure is obtained at each pair of bone screws 30 such that the attachment of plate 2 to the bone would be highly secure due to the trapping of a wedged mass of bone material between the angled bone screws, even if any thread stripping should occur. The "claw" may be further formed by three angled bone screws in a tripod configuration or by four bone screws in a four sided claw configuration.

b. Single-Lock Plate Systems

Figure 43:
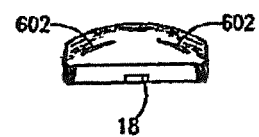
FIG. 43 is an end view of the plate shown in FIG. 40.
Figure 41:
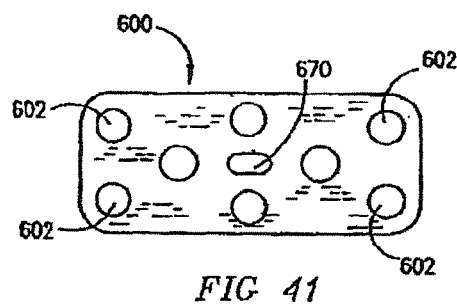
FIG. 41 is a top plan view of the plate shown in FIG. 40.
Figure 44:
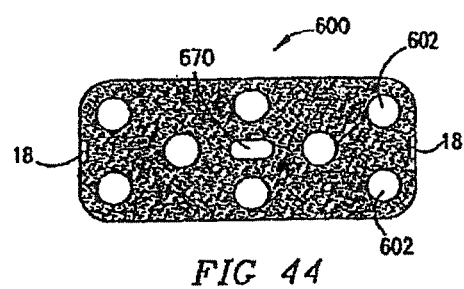
FIG. 44 is a bottom plan view of the plate shown in FIG. 40.
Figure 42:
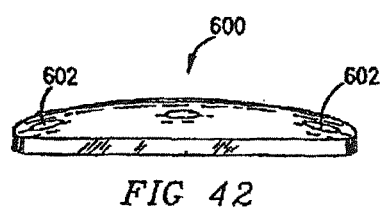
FIG. 42 is a side view of the plate shown in FIG. 40.

Another embodiment of the present invention, the single locking plate system will now be described. FIGS. 40-45 are views of a first embodiment of a single locking plate system generally referred to by the numeral 600. Plate 600 has the same contour as plate 2 shown in FIGS. 1-5. Plate 600 has a bottom surface 27 for placement against bone portions, wherein a substantial portion of bottom surface 27 is either flat and/or convex along the longitudinal axis of the plate though a lesser portion of bottom surface 27 may be otherwise configured. As shown in FIG. 43, in another embodiment plate 600' has a bottom surface 627' that is substantially flat along the transverse axis of plate 600'.

In a preferred embodiment, plate 600 contains bone screw receiving holes 602 which are internally threaded 603 for receiving corresponding locking elements in the form of a locking cap 610, shown in FIGS. 49-52. For example, in plate 600, the bone screw hole 602 may have an outer diameter appropriate to the screw diameter appropriate to the bone(s) for which the plating system is to be applied. By way of example only, for use on a long bone such as the humerus, a bone screw of a diameter of 4.0 to 6.5 mm would be used and generally the screw head would be slightly larger in diameter. If a threaded locking cap were to be used then allowing for the space occupied by the cap is threads, the opening in the upper plate surface to receive the locking cap would be similar to generally 0.2 mm to 4.0 mm greater than the screw head size which could be 0.2 mm to 6 mm larger in diameter than the threaded shaft diameter of the bone screw of approximately 5 mm with a preferred range of 4-6 mm though possibly greater. Cap attaching means other than threads may be used, such as bayonet type attachment elements.

Figure 46:
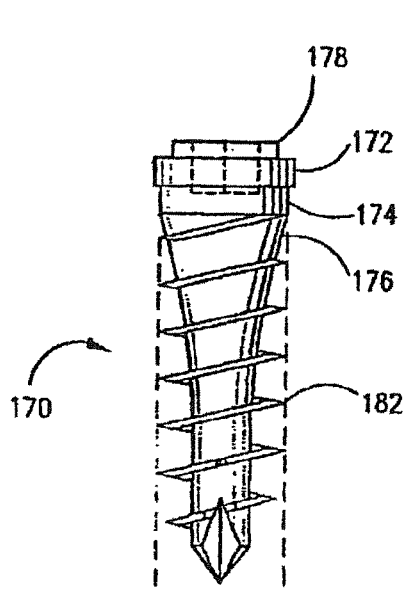
FIG. 46 is a side view of a bone screw used with the plate shown in FIG. 40.
Figure 47:
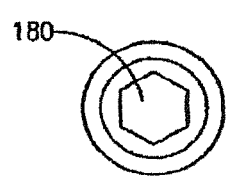
FIG. 47 is a top view of the bone screw shown in FIG. 46.
Figure 48:
FIG. 48 is a bottom view of the bone screw of FIG. 46.

The bottom of each bone screw receiving hole 602 of plate 600 has an inwardly stepped portion of properly selected dimensions for retaining an associated bone screw 170, as shown in FIGS. 46-48. As described in greater detail below, in this embodiment, a single locking element in the form of a locking cap 610 having threads 608 shown in FIGS. 49-52, is associated with each of the bone screws receiving holes 602.

The difference between the bone screw 170 used in the single locking embodiment of the plate from the bone screw used in association with the multiple locking plate is essentially due to the fact that whereas in the multiple locking plate embodiment the locking elements slide over a portion of the top 39 of the screw head 32 by a pressing, camming, or ramp action, in the single locking embodiment the locking cap 610 presses directly on the head 172 of the bone screw 170. Therefore, the head 172 of the bone screw 170 of the present embodiment need not be smooth.

FIG. 55 shows two bone screws 170 and associated threaded locking caps 610 in their fully installed positions. In these positions, head portions 174 and 176 of each bone screw 170 form an interference fit with corresponding portions of an associated bone screw receiving hole 602. Rim 612 of each threaded locking cap 610 forms an interference fit with upper portion 178 of the head of its associated bone screw 170. Because the thread 608 of each locking cap 610 mates precisely with the internal thread in an associated bone screw receiving hole 602, each threaded locking cap 610 is additionally subjected to a clamping force between associated head portion 178 and the internal threads 603 of associated bone screw receiving hole 602. Preferably the rounded head 614 of each threaded locking cap 610 assures that the upper surface of an assembled plating system will be free of sharp edges, or projections.

Figure 45:
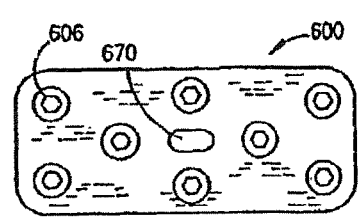
FIG. 45 is a top plan view of the plate shown in FIG. 40, with locking elements in place.

FIG. 45 is a top plan view of the plate 600 partially installed, with threaded locking caps 600 installed in bone screw receiving holes 602.

Figure 49:
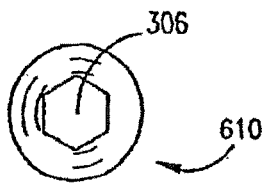
FIG. 49 is a top view of a locking cap for use with the single locking plate of FIG. 40.
Figure 50:
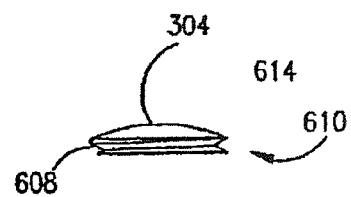
FIG. 50 is a side view of the locking cap shown in FIG. 49.
Figure 51:
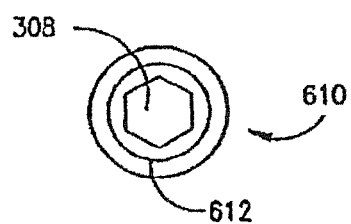
FIG. 51 is a bottom view of the locking cap shown in FIGS. 49 and 50.
Figure 52:
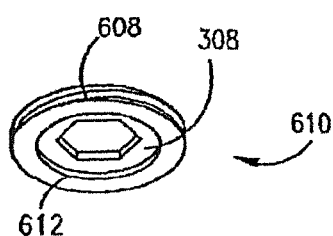
FIG. 52 is a bottom perspective view of the locking cap of FIGS. 49-51.
Figure 53:
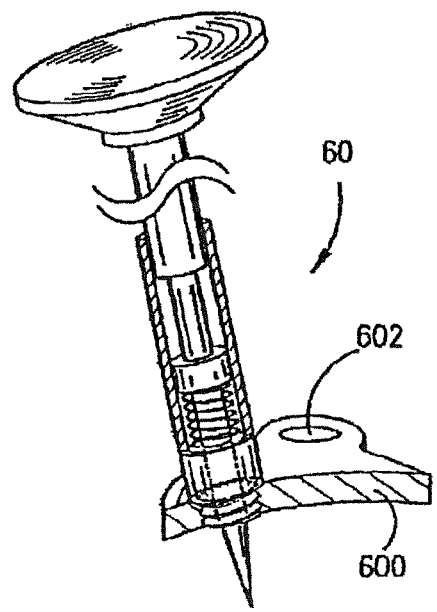
FIG. 53 is a cutaway view of the hole forming instrument threaded to a bone screw hole of a plate.
Figure 54:
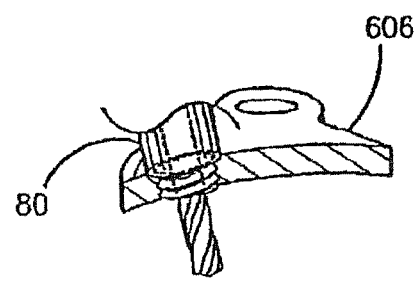
FIG. 54 is a perspective side sectional view of a drill and drill guide threadably engaged to the plate for drilling the hole for insertion of a bone screw.

FIGS. 47-49 show a bone screw 170 for use with the single locking plating system according to the invention. Bone screw 170 differs from bone screw 30 previously described in detail, only with regard to the stepped configuration of head 172. Preferably, bone screw 170 includes a lower portion 174 which is contiguous with the screw shank and has a reduced diameter equal to the maximum diameter of the shank 176. Portion 178 of head 172 also has smaller diameter than lower portion 174. The thread 182 has the same configuration as for the bone screw 30 discussed above. However, either embodiment of bone screws can be used with any of the plates.

As in the case of the multiple locking plating system described above, the bone screws 170 for use in the single locking plating system are preferably solid, where the screws adjoin the lower plate surface, where as some screws used with prior art plates are hollow and are prone to breakage, the only recess in the heads of the present invention screws being for engagement of the tip 222 of driving tool 220 and with the recess being above the critical area of the lower plate surface screw junction. Therefore, these bone screws 170 remain robust. The screw heads are not deeply slitted into portions as per some prior art screws and the locking caps do not impose a radial outer force to expand the bone screw heads, so again the screw heads of the present invention are not spread apart and stressed and weakened, and so remain robust. It is appreciated that variable angle screws 30' shown in FIG. 30B may be used in association with the single-lock plating system of the present invention.

Figure 59:
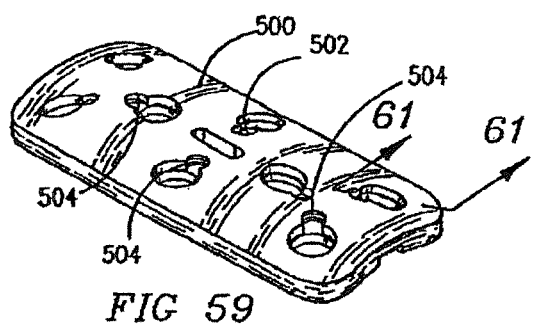
FIG. 59 is a perspective view of a second embodiment of a single locking plate having individual locking elements to lock each bone screw.
Figure 62:
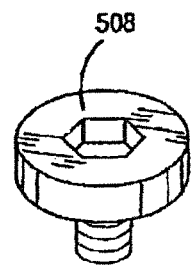
FIG. 62 is a perspective view of an alternative locking element for use with a first modification of the single locking plate of FIG. 59.
Figure 60:
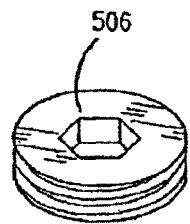
FIG. 60 is a perspective view of a threaded locking element for use with the single locking plate of FIG. 59.
Figure 61:
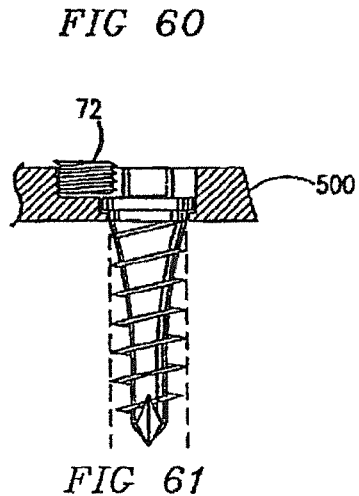
FIG. 61 is a partial side sectional view of the plate of FIG. 59 viewed along lines 73-73 with the locking element of FIG. 60 in place to hold a bone screw, but not fully tightened.
Figure 63:
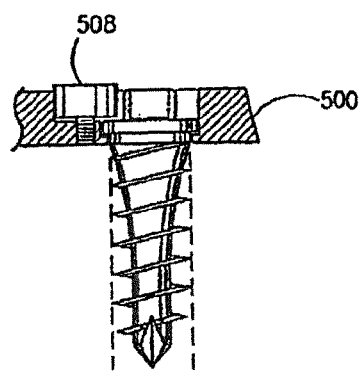
FIG. 63 is a side sectional view of the first modification of the plate of FIG. 59 with the locking element of FIG. 62.
Figure 64:
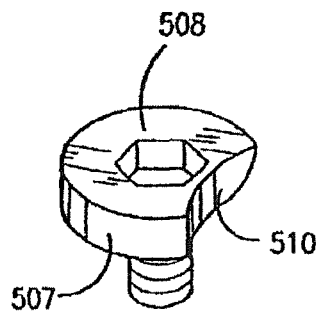
FIG. 64 is a perspective view of an alternative locking element for use with the first modification of the plate of FIG. 59.
Figure 66:
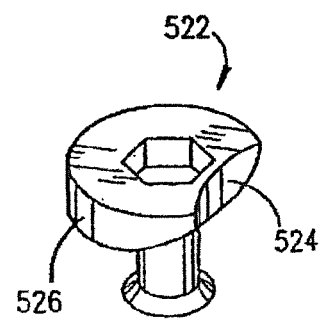
FIG. 66 is a perspective view of another alternative locking element in the form of a rivet for use with a second modification of the locking plate of FIG. 59.
Figure 65:
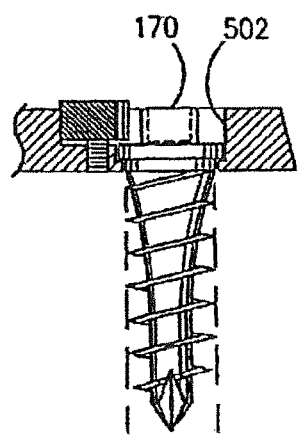
FIG. 65 is a side sectional view of the first modification of the plate of FIG. 59 with the locking element of FIG. 64 in place.
Figure 67:
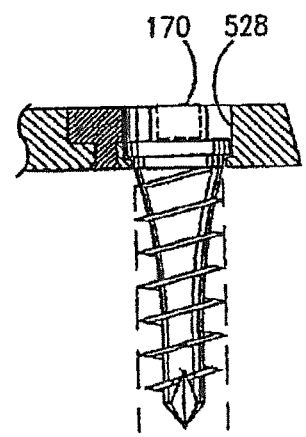
FIG. 67 is a partial side sectional detail view of the plate of FIG. 59 modified to use a locking element of FIG. 66 shown in place.

Referring to FIGS. 59, 61 and 63 another alternative embodiment of the plate system of the present invention is shown and referred to by the number 500. The plate 500 may have any contour as any of the plates of the present invention appropriate for skeletal use and in which a substantial portion of the lower surface of the plate is either flat or convex along the longitudinal axis of the plate. Associated with each of the bone screw openings 502, are threaded openings 524 offset from the bone screw openings 502 for receiving the locking element 506, 508, shown in FIGS. 60 and 62 as a threaded locking set screw or cap 506 or screw 508. Alternatively, locking element 506 may have a cutout portion with a radius greater than the radius of a bone screw head as is shown in connection with locking element 508 in FIG. 64.

It is appreciated that other configurations of single locking plates may be employed.

Referring to FIGS. 64-67 the heads 507 and 526 of the locking elements 508 and 522 have a recess 510 and 524 corresponding to the radius of the bone screw openings 502 and 528 so that the locking element 508 and 522 may be installed in place prior to the insertion of the bone screw 170 into the bone screw receiving hole 502 and 528. When the locking elements 508 and 522 are rotated, a portion of its head extends over the top of the head of bone screw 170 to lock it in place. As with the above embodiments, the bottom surface of the locking screws 508 and 522 can have a ramped, cammed, or other configuration for engagement with at least a portion of the screw head.

Figure 68:
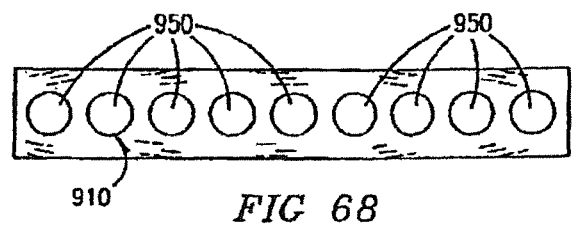
FIG. 68 is a top plan view of a single-lock plate.

Referring to FIG. 68, a locking plate 900 is shown in which there are a number of bone screw receiving holes 950 along the longitudinal axis of plate 900. With plate 900 of FIG. 68, the close spacing and increased number of bone screw receiving holes permits the surgeon to locate appropriate holes to be aligned with each of the bone portions to be fixated, as well as allowing for more points of fixation to the bone.

2. Crossing Screw Plating System

Figure 69A:
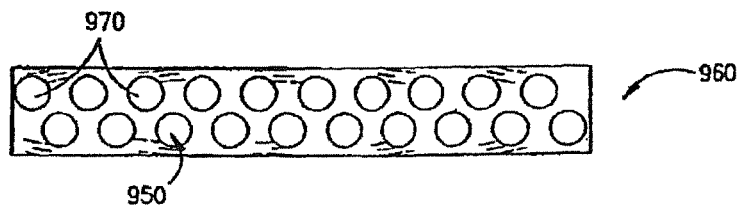
FIG. 69A is a top plan view of plate of a single-lock the present invention having a staggered screw hole pattern to provide crossing over of the bone screws into bone.

Referring to FIG. 69A, an alternative embodiment of the plate of the present invention is shown and generally referred to by the numeral 960. The plate 960 has multiple bone screw receiving holes 970 passing through plate 960. The bone screw receiving holes 970 are spaced apart in a staggered configuration such that the center point of each of the bone screw receiving holes 970 are on transverse lines that are offset from one another. The center point of the bone screw receiving holes 970 are also offset from the midline of plate 970, but with less longitudinal distance between one another, while providing for sufficient distance between holes 970 to assure plate strength, than plate 900 shown in FIG. 68.

Figure 69B:
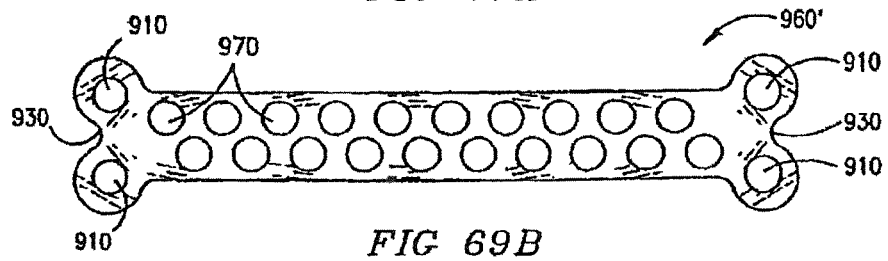
FIG. 69B is an alternative embodiment of the plate shown in FIG. 69A.

Referring to FIG. 69B, an alternative embodiment of plate 960 is shown and generally referred to by the numeral 960'. Plate 960' has the same staggered pattern of bone screw holes 970 as plate 960 to permit crossing over of two bone screws 30. In addition, plate 960' has an overall configuration suitable for use in the spine including the anterior cervical spine. For such use, an embodiment could have openings 910 in lobed portions at the corner of plate 960' and recesses 930 for use with a compressing apparatus. Plate 960 could have additional pairs of lobes along the plate length. It is appreciated that the overall configuration of plate 960' can vary as can the offset pattern of the bone screw holes.

Figure 70A:
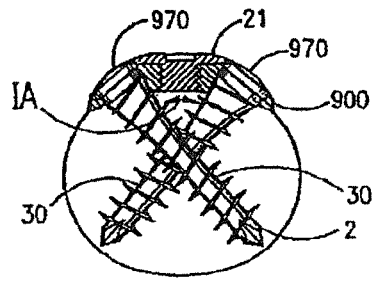
FIG. 70A is cross sectional view of a bone with the plate of FIG. 69A or 69B engaged to the bone with two bone screws shown crossed over and penetrating the bone in different planes.

As shown in FIG. 70A, the offset pattern of bone screw receiving holes 970 permits longer bone screws 30 to be used than would otherwise be possible if the screws were aligned in transverse pairs without having bone screws 30 touch each other, due to the fact that the bone screws 30 are in different planes, and each bone screw 30 gets to travel a much longer diagonal path in crossing the sagittal midline, providing greater fixation.

In the preferred embodiment of plate 960, the shafts of two bone screws 30 cross over in close proximity to each other and define an included angle IA preferably between 25 to 90 degrees. Such a crossed configuration of bone screws 30 provides an extremely stable engagement of plate 960 to the bone as they are diagonally crossed within the same bone, thus trapping an area of bone between them.

Figure 70B:
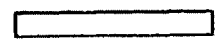
FIGS. 70B-70D are end views of alternative embodiments of the plate shown in FIG. 70A.
Figure 70C:
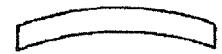
Figure 70D:
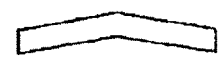

For example, as shown in FIGS. 70B-70D, end views of alternative embodiments of plate 960' are shown wherein the bottom surface of the plate may be in the transverse plane relatively flat, curved, or otherwise configured to fit the surface configuration of the bone or bones to which the plate is to be applied. As shown in FIGS. 70E and 70F, plates 960' overall are generally shaped to conform to the bone(s) B to which they are applied.

3. Segmentable Plating System

Figure 73:
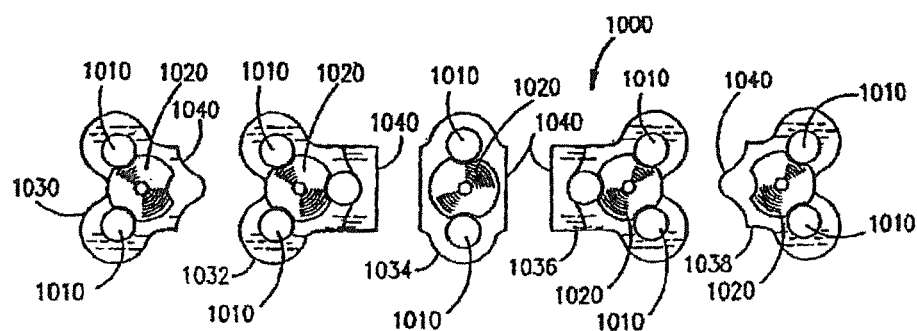
FIG. 73 is a top plan view of an alternative embodiment of the present invention in the form of a multiple locking segmentable plate shown in a separated state.

Referring to FIG. 73, a further embodiment of the present invention in the form of a segmentable plate generally referred to by the number 1000 is shown in an separated state. Segmentable plate 1000 has an elongated body with a plurality of bone screw receiving holes 1010 spaced apart along a substantial portion of the length of the segmentable plate 1000. Segmentable plate 1000 has a multiple locking system 1020 for locking bone screws to plate 1010 as described above in connection with multi-lock plate 2 shown in FIGS. 1-7. Plate 1000 is preferably, but not limited to being made of a malleable material, such as titanium or one of its surgically acceptable alloys.

Plate 1000 comprises a plurality of segments 1030-1038 which can be separated from each other. A first segment 1030 of plate 1000 is marked by a segmentation zone 1040 along which the plate may be separated to separate first segment 1030 from the remainder of plate 1000. Segmentation zone 1040 can be any type of scoring which creates a place of least resistance along which when the plate 1000 is bent sufficiently to create a separation in the material of plate 1000, the separation will occur along the segmentation zone. By way of example only, in an anterior cervical plate having a thickness of 3 mm segmentation zone 1040 may be formed by removing approximately 0.25 mm to 0.5 mm of material in total from the upper surface, lower surface or both upper and low plate surfaces combined of the plate. The scoring can be relatively thicker or thinner in width, variable in depth and of variable shape (e.g. "V" notched, rounded, etc.) to achieve the desired qualities.

If plate 1000 is made of titanium, the inherent qualities of titanium are such that the plate may be separated simply by bending the plate sufficiently along segmentation zone 1040 while supporting the plate with appropriate plate holders to either side of segmentation zone 1040 and then bending the plate towards its original position at which time the plate will separate apart along the segmentation zone 1040, providing a sufficiently clean edge suitable for surgical use.

In use in the cervical spine as few as, only four different segmentable plates 1000 may be required to cover the wide range of different longitudinal spacing distances between bone screw receiving holes 1010 for application to one to four levels of the cervical spine. For example, a set of four segmentable plates 1000 to cover the various combinations required for application to one to four levels of the cervical spine would include a first segmentable plate having a first segment with a spacing distance between the bone screw receiving holes of 10 mm, and subsequent segments similarly spaced at 10 mm intervals between the holes; a second segmentable plate having a first segment with a spacing distance between the bone screw receiving holes of 12.5 mm, and subsequent segments spaced at 12.5 mm intervals between the screw holes; a third segmentable plate having a first segment with a spacing distance between the bone screw receiving holes of 15 mm and subsequent segments spaced apart at 15 mm intervals between the holes; and a fourth segmentable plate having a first segment with a spacing distance between the bone screw receiving holes of 17.5 mm and subsequent segments spaced apart at 17.5 mm intervals between the holes.

Figure 74:
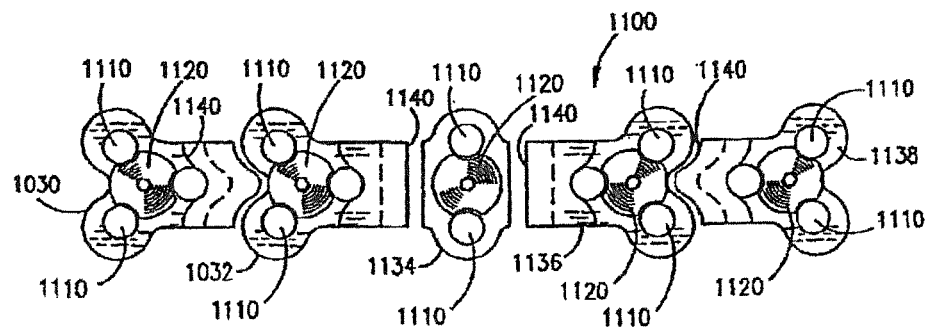
FIG. 74 is a top plan view of an alternative embodiment of a multiple locking segmentable plate of FIG. 73 shown in a separated state.
Figure 75:
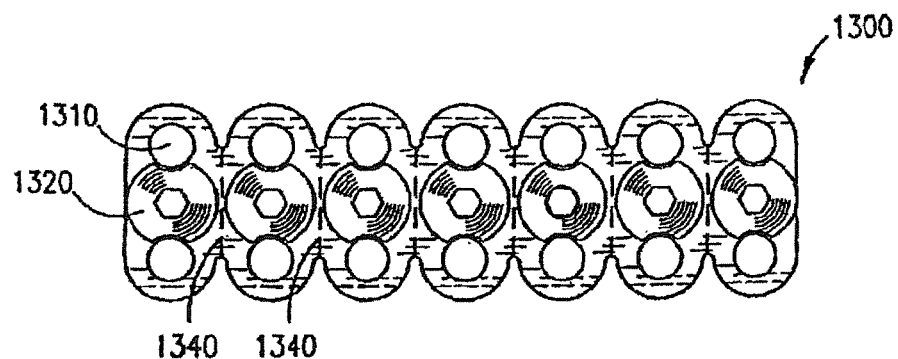
FIG. 75 is a top plan view of an alternative embodiment of a multiple locking segmentable plate shown in an unseparated state.
Figure 76:
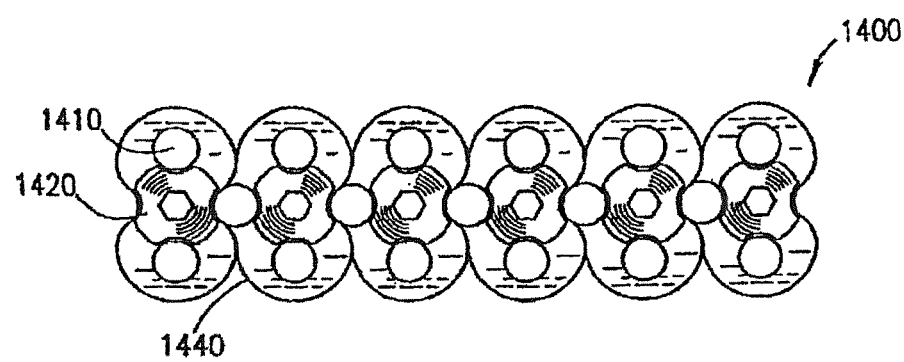
FIG. 76 is a top plan view of an alternative embodiment of a multiple locking segmentable plate shown in an unseparated state.
Figure 77:
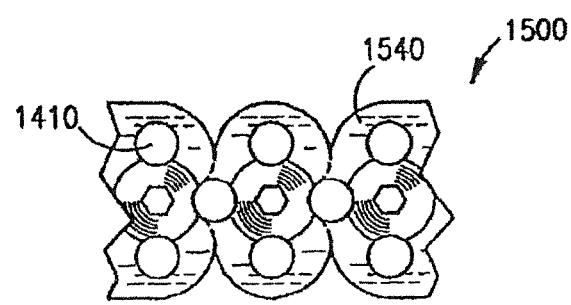
FIG. 77 is a top plan view of a portion of an alternative embodiment of a multiple locking segmentable plate shown in an unseparated state.
Figure 78:
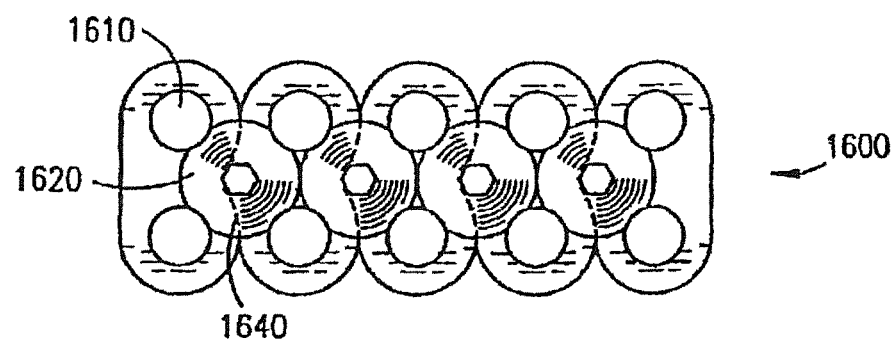
FIG. 78 is a top plan view of an alternative embodiment of a multiple locking segmentable plate shown in an unseparated state.

The longitudinal spacing between the bone screw receiving holes 1010 may be varied by changing the length of the portion of plate 1000 between bone screw receiving holes 1010 as illustrated by the dotted lines in FIG. 74.

Figure 79:
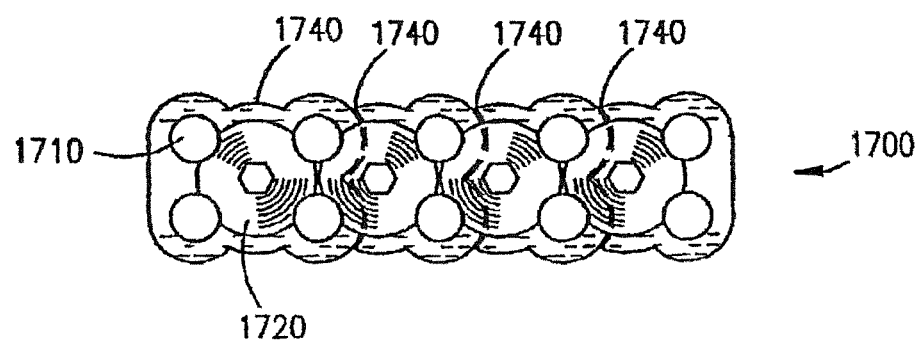
FIG. 79 is a top plan view of the multiple locking segmentable plate of FIG. 78 shown in a separated state.

While the described plates may be separable into a multitude of usable portions, as would be desirable for manufacturing purposes and possibly for clinical use, because of regulatory issues involving the identification of each implant with a distinct and singular implant identification number for tracking purposes it may be desirable to configure the plates of the present invention such that each plate will yield only one usable portion. In order to accomplish this goal, the segmentation zone 1040 is made as shown in FIG. 79, such that the unused, separated pieces of the segmentable plates would not be usable as plates and would be discarded.

The ability to separate a plate into segments also provides significant advantages in the manufacturing process. By way of example, in the process of investment casting, a process commonly used to produce plates, the cost of the material is not as significant as the labor involved in the manufacturing. Therefore, the manufacturer can cast one long segmentable plate which can then be separated in the later manufacturing stages to yield multiple plates at an overall lower cost. Similarly, if the plate were in the alternative to be manufactured by machining from solid stock, great labor could be saved by fixturing and securing a single long plate that is later separable into multiple plates rather than having to fixture and secure each of those plates individually.

Referring to FIGS. 75-79, various segmentable plates 1300-1700 are shown for application in reconstructive surgery. Plates 1300-1700 have bone screw receiving holes 1310-1710, locking elements 1320-1720, and separation zones 1340-1740 respectively. For example, during repair of a broken eye socket, the segmentable plates 1300-1700 can be used to align and maintain the broken bone portions in correct spatial relationship. The curved characteristics of an eye socket would require the plate used to repair the socket to match the curvature. The segmentable plates 1300-1700 are made of a malleable metal, the malleability of which is enhanced by the segmentation of the plate, and can be easily contoured by the surgeon to the appropriate curvature. The correct length of the segmentable plate can also be easily selected by the surgeon by separating the plate at the appropriate segment as described above in connection with plate 1000 shown in FIG. 73.

It should be noted that if for example surgical titanium alloy is selected for the plate material, then the separation zones allow the plate to be more easily bent, but without separating. The present invention makes a virtue of the material property of that alloy in that it may be bent without damage, but fails with surprisingly little force if first bent and then bent back. Back bending is therefore only done for plate separation and is not needed for contouring which requires only primary bending.

Figure 80:
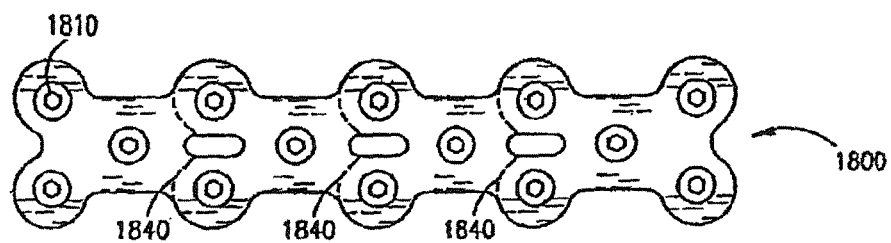
FIG. 80 is a top plan view of an alternative embodiment of the present invention in the form of a single-lock segmentable plate shown in an unseparated state.
Figure 81:
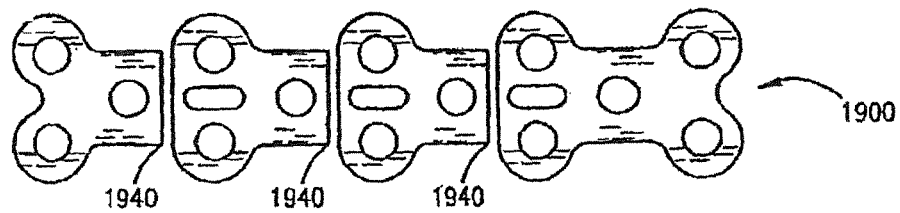
FIG. 81 is a top plan view of the single-lock segmentable plate of FIG. 80 shown in a separated state.
Figure 87:
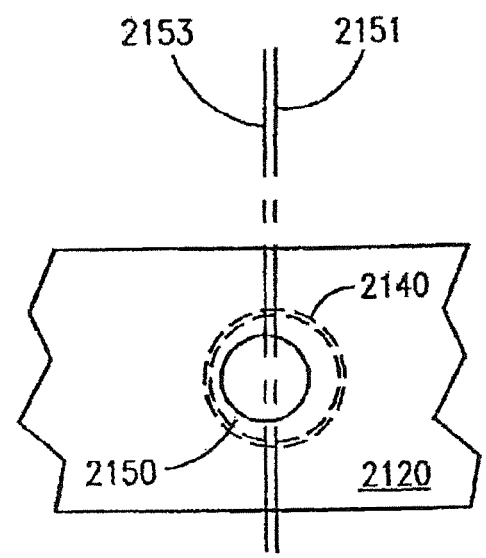
FIG. 87 is a top plan view and opening in the plate shown in FIG. 86.
Figure 88:
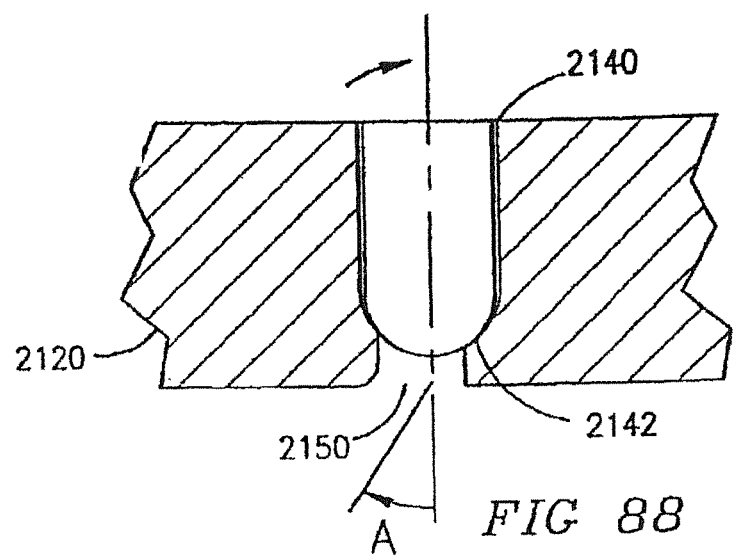
FIG. 88 is a side sectional view of the opening in the plate shown in FIG. 87.
Figure 91:
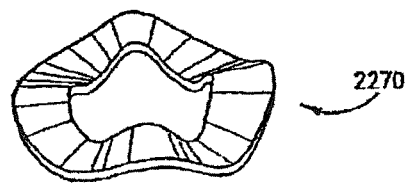
FIG. 91 is a top perspective view of the Belville type washer of the active dynamic screw-plate-lock system of FIG. 89.
Figure 89:
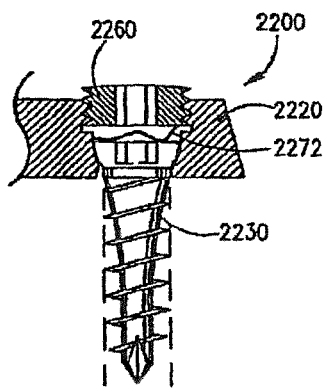
FIG. 89 is a partial side sectional view of an active dynamic screw-plate-lock system of the present invention.
Figure 90:
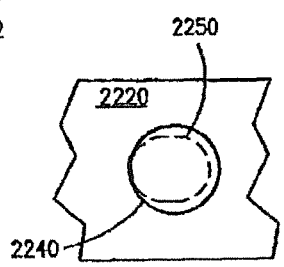
FIG. 90 is a top plan view of the opening in the plate shown in FIG. 89.
Figure 92:
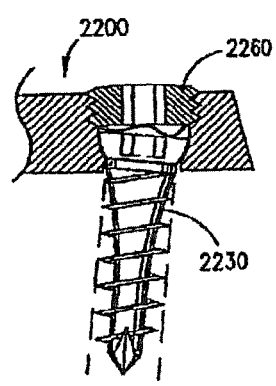
FIG. 92 is a partial side sectional view of the active dynamic screw-plate-lock system of FIG. 82 with the lock further tightened and the screw seated.

Referring to FIGS. 80 and 81, alternative embodiments of the segmentable plate are shown and generally referred to by the numeral 1800 and 1900. Plates 1800-1900 having locking elements 1820 that are inserted into bone screw receiving holes 1810 and correspond to the single lock plate configuration described above in connection with FIGS. 40-49. Segmentable plates 1800-1900 may be segmented at segmentation zones 1840 and 1940 as described above in connection with the multiple lock embodiment of the segmentation plate 1000.

4. Combination Screw-Lock-Plating System a. Passive Dynamic

Referring to FIGS. 82-84 the passive dynamic system 2000 is shown having a plate with a screw hole 2010 passing through the top and bottom surfaces of the plate 2020 for receiving a bone screw 2030. The screw hole 2010 has a round opening 2040 at the top of the plate 2020 and an opening 2050 in the bottom of the plate that is in part coaxial with the top opening 2040, but extends in one direction to form an oblong. The rounded head 2032 of bone screw 2030 is prevented from backing out of plate 2020 with a locking element 2060 that is engaged to plate 2020, while the shaft of bone screw 2030 is capable of angular motion in the direction of arrow A relative to plate 2020, since there is space in the oblong-shaped bottom opening 2040 of the screw hole 2010 for the shaft of the bone screw 2030 to travel in the one permitted direction relative to the plate 2020.

The passive dynamic system allows bone screw 2030 to move relative to plate 2020 even after being locked to plate when a force is presented against the screw. This system does not cause screw movement, but only allows for movement of the screw to occur and this is a "passive" system. Nevertheless, screw 2030 retains the ability to resist any unwanted motion in all other directions. The use of variable screw 30' as already described may also allow for passive dynamic action, but is not generally preferred as it does not limit the motion to but a single direction.

b. Self-Compressing

Referring to FIGS. 85-88, a self-compressing system 2100 is shown comprising a plate 2120 having a bone screw receiving 2110 hole with a top opening 2140 that is preferably but not necessarily round, and having a rounded recessed portion 2142 is shown. The bone screw receiving hole has bottom opening 2150 that is smaller in diameter than the top opening 2140 and has a central longitudinal axis 2153 that is offset from the central longitudinal axis 2151 of the top opening 2140. The bone screw has a rounded head portion 2132 which fits within the rounded bottom 2142 of the top opening 2140 and permits movement of the screw head 2132 within the top opening in order to provide the appropriate angle A of the bone screw shaft with respect to the plate 2120 as the bone screw shaft passes through the bottom opening 2150.

In the self-compressing system, as the bone screw 2130 is being locked to the plate 2120 with a locking element 2160, the locking element 2160 puts pressure on the bone screw head 2132 to make the bone screw 2130 move in one direction. The bone screw 2130 cannot move back once it is locked to the plate 2120 by the locking element 2160. The purpose of the self-compressing system 2100 is to provide a fixed and locked angle A on the bone screw 2130 for providing compression of bone portions.

c. Active Dynamic

Referring to FIGS. 89-92, the active dynamic system 2200 of the present invention is shown comprising a screw 2230 that is mounted to a plate 2220 under a spring loaded force, such as with a Belville type washer 2270 that applies a selected force to the screw 2230. The bone screw 2230 will move in the direction of the force that is being applied as bottom opening 2250 of the bone screw receiving hole is oblong shaped. For example, the big end 2272 of the spring formed by washer 2270 bears down on the screw head 2232 away from the direction that the bone screw 2230 is to be moved. For any given use, (plate, screw, hole, and spring) it is simple to determine correct resistance, that being an amount less than would separate the bone.

Figure 93:
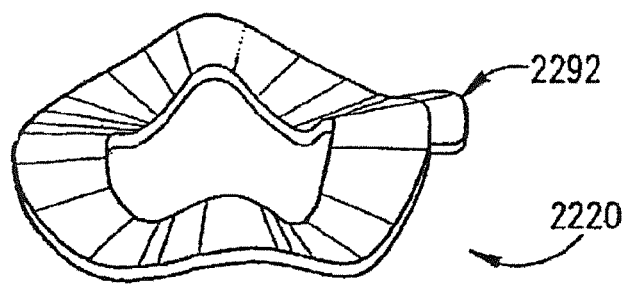
FIG. 93 is a top perspective view of an alternative embodiment of the washer of FIG. 94 having a tab for insertion into a corresponding recess in the plate.
Figure 94:
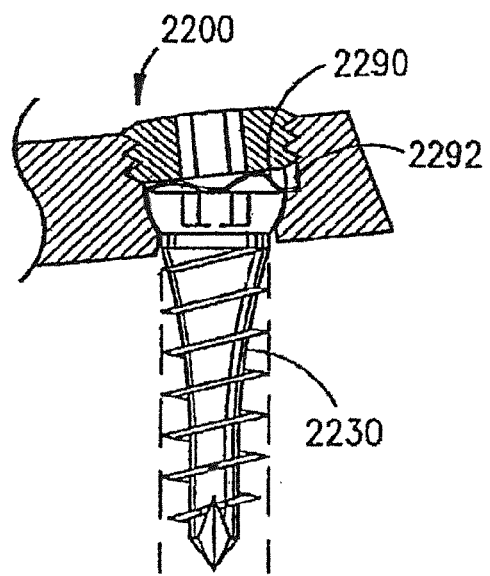
FIG. 94 is a partial side sectional view of the active dynamic screw-plate-lock system of FIG. 93 with the lock fully inserted, the screw seated, and the tab of the washer inserted into a corresponding recess in the plate.

Referring to FIGS. 93-94, the washer 2270 may also have a tab 2290 which fits into a recess 2292 formed within the top opening in order to facilitate proper orientation of the washer when placed within the opening or alternatively the washer 2270 may have a non-circular shape so as to not rotate when positioned.

In an active dynamic system, a pre-loaded force is applied to a bone screw that keeps the screw in a certain orientation with respect to the plate. The bone screw will only move further in the pre-oriented direction if there is space available and if there is no opposing force present to counteract the pre-loaded force on the screw. These teachings may be readily and beneficially combined so as to for example form a system that compresses on full screw seating, continues to urge the bone portions together, and can permit still further shortenings.

Figures 95A, 95B, 95C:
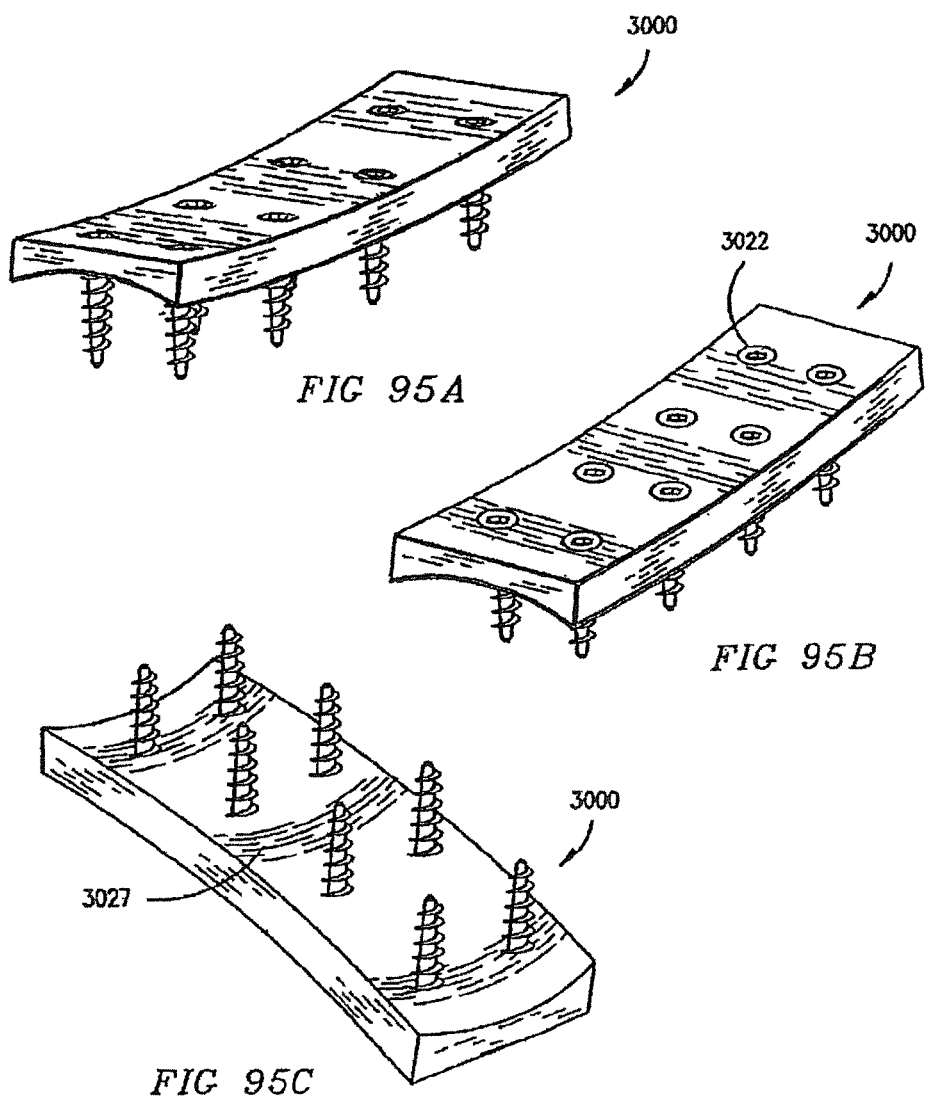
FIG. 95A is a side perspective view of an alternative embodiment of a plate in accordance with the present invention.
FIG. 95B is a top perspective view of the plate in FIG. 95A.
FIG. 95C is a bottom perspective view of the plate in FIG. 95A.

Referring to FIGS. 95A-95C, an alternative embodiment of a plate of the present invention is shown and generally referred to by the numeral 3000. Plate 3000 has a bottom surface 3027 that is convex along a substantial portion of the longitudinal axis of the plate and is concave along the transverse axis of the plate 3000. Plate 3000 has a single-locking element 3022 for locking a single bone screw 3030 to plate 3000.

Referring to FIGS. 96A-96C, an alternative embodiment of a plate of the present invention is shown and generally referred to by the numeral 3100. Plate 3100 has a bottom surface that is flat along a substantial portion of the longitudinal axis of the plate and is concave along the transverse axis of the plate. Plate 3100 has a multiple locking element 3120 for locking two bone screws 3130 and single locking elements 3122 for locking individual bone screws 3130 to plate 3100. Bone screw receiving holes 3140 are staggered such that the center point of each of the bone screw receiving holes 3142 and 3144 are on transverse lines that are offset from one another. The center point of the bone screw receiving holes 970 are also offset from the midline of plate. The shafts of two bone screws 30 cross over in close proximity to each other and define an included angle IA between 25 to 90 degrees. Such a crossed configuration of bone screws 30 provides an extremely stable engagement of plate 960 to the bone as they are very close together and diagonally crossed within the same bone, thus trapping an area of bone between them.

Plate 3100 comprises a plurality of segments 3150-3156 which can be separated from each other. A first segment 3150 of plate 3100 is marked by segmentation zones 3160-3164 along which the plate may be separated to separate segments 3150, 3152, 3154, or 3156 from the remainder of plate 3100. Segmentation zones 3160-3164 can be any type of scoring which creates a place of least resistance along which when the plate 3100 is bent sufficiently to create a separation in the material of plate 3100, the separation will occur along the segmentation zone.

It is appreciated that plate 3100 may include one or more of the screw-lock-plating systems 2000, 2100, or 2200 described above in FIGS. 82-84.

Referring to FIGS. 97A-97D, an alternative embodiment of a plate of the present invention is shown and generally referred to by the numeral 3200. Plate 3200 has a bottom surface that is flat along a substantial portion of the longitudinal axis of the plate and is concave along the transverse axis of the plate and has an upper surface that is concave along the transverse axis of the plate 3200.

As shown in FIG. 97D, plate 3000 may include one or more of the screw-lock-plating systems 2000, 2100, or 2200 described above in FIGS. 82-94.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

While specific innovative features may have been presented in reference to specific examples, they are just examples, and it should be understood that various combinations of these innovative features beyond those specifically shown are taught such that they may now be easily alternatively combined and are hereby anticipated and claimed.

What is claimed is:

1. An orthopedic implant for engaging at least one non-vertebral bone of the human body, said implant comprising:
   a body having a first end, a second end, a length therebetween, and a width perpendicular to the length, said body including a bone-contacting surface along the length of said body, said bone-contacting surface configured to be placed against the at least one non-vertebral bone;
   at least two bone screw receiving holes extending through said body from a screw receiving side to a screw exit side proximate said bone-contacting surface, each of said bone screw receiving holes having a central longitudinal axis extending therethrough from said screw receiving side to said screw exit side, and being adapted to receive a bone screw for engaging said implant to the at least one non-vertebral bone, said each of said bone screw receiving holes having a seat configured to contact said respective one of said at least two bone screws;
   at least two bone screws each having a central longitudinal axis, each of said at least two bone screws having a leading end for insertion through one of said at least two bone screw receiving holes, respectively, and into the at least one non-vertebral bone and a trailing end opposite said leading end, said at least two bone screws each having a head and including proximate said trailing end a contact surface area generally transverse to the central longitudinal axis and oriented toward said trailing end of said each of said at least two bone screws, respectively, said generally transverse contact surface areas being formed on said heads, said heads each including a downward facing surface being configured to contact said implant and oriented at least in part away from said trailing end of said each of said at least two bone screws, respectively, said heads each including a side surface between said trailing end and said downward facing surface of said each of said at least two bone screws, said side surface being closer to said trailing end than said generally transverse contact surface area is to said trailing end; and
   at least one locking element, each of said at least one locking element adapted to lock to said implant only said respective one of said at least two bone screws inserted in one of said at least two bone screw receiving holes, said each of said at least one locking element contacting said generally transverse contact surface area and said side surface of said head of said respective one of said at least two bone screws so as to retain said respective one of said at least two bone screws to said implant, said each of said at least one locking element having an outer perimeter contacting at least a portion of a perimeter of said one of said at least two bone screw receiving holes when said each of said at least one locking element contacts said generally transverse contact surface area and said side surface of said head of said respective one of said at least two bone screws, said each of said at least one locking element being removably coupled to said implant, said each of said at least one locking element having a round inner surface adapted to contact said side surface of said head of said respective one of said at least two bone screws, wherein, when said each of said at least one locking element contacts said respective one of said at least two bone screws to retain said respective one of said at least two bone screws to said implant, said each of said at least one locking element has an upper surface oriented toward said screw receiving side of said implant, said upper surface of said each of said at least one locking element is convex in a plane parallel to the central longitudinal axis of said respective one of said at least two bone screws.

2. The implant of claim 1, wherein said each of said at least two bone screw receiving holes has a side wall, said side wall having a groove configured to receive one of said at least one locking element.

3. The implant of claim 2, wherein said groove in said side wall of a first of said at least two bone screw receiving holes encircles the entire perimeter of said first bone screw receiving hole, and said groove in said side wall of a second of said at least two bone screw receiving holes encircles the entire perimeter of said second bone screw receiving hole.

4. The implant of claim 1, wherein said head of said respective one of said at least two bone screws has a round cross section through said side surface thereof and transverse to the central longitudinal axis of said respective one of said at least two bone screws.

5. The implant of claim 4, wherein said each of said at least one locking element forms an interference fit with said side surface of said respective one of said at least two bone screws.

6. The implant of claim 4, wherein said each of said at least one locking element clamps onto said side surface of said respective one of said at least two bone screws.

7. The implant of claim 4, wherein said side surface of said head of said respective one of said at least two bone screws has a height and said round cross section of said head of said respective one of said at least two bone screws is through a midpoint of said height, said round inner surface of said each of said at least one locking element is adapted to contact said side surface of said head of said respective one of said at least two bone screws at said midpoint.

8. The implant of claim 1, wherein said respective one of said at least two bone screws has a recess in said trailing end thereof for engagement by a tool for rotation of said respective one of said at least two bone screws, said each of said at least one locking element having an opening through the center thereof, said recess having a first cross sectional dimension transverse to the central longitudinal axis of said respective one of said at least two bone screws, and said opening having a second cross sectional dimension transverse to the central longitudinal axis of said respective one of said at least two bone screws when said each of said at least one locking element contacts said respective one of said at least two bone screws to retain said respective one of said at least two bone screws to said implant, said first cross sectional dimension of said recess being less than said second cross sectional dimension of said opening.

9. The implant of claim 1, further in combination with a fusion promoting substance.

10. The implant of claim 9, wherein said fusion promoting substance is at least in part other than bone.

11. The implant of claim 9, wherein said fusion promoting substance comprises bone morphogenetic protein.

12. The implant of claim 1, wherein said bone contacting surface extends along the entire length of said body.

13. The implant of claim 1, wherein at least one of said bone screw receiving holes is configured to form an interference fit with a properly dimensioned bone screw to be received therein.

14. The implant of claim 1, wherein at least a portion of one of said implant, said locking element, and said bone screws is a bioresorbable material.

15. The implant of claim 1, wherein said bone-contacting surface is textured for engagement of said body with the at least one bone.

* * * * *

UNITED STATES PATENT AND TRADEMARK OFFICE
CERTIFICATE OF CORRECTION

PATENT NO.       : 8,480,717 B2
APPLICATION NO.  : 13/610281
DATED            : July 9, 2013
INVENTOR(S)      : Gary K. Michelson Page 1 of 1

It is certified that error appears in the above-identified patent and that said Letters Patent is hereby corrected as shown below:

Title Page 3, Item (56) References Cited, Column 2:
Line 12, Foreign Patent Documents: change "WO 05/28164" to -- WO 95/26164 --; and
Line 60, Other Publications: change "Usa" to -- USA --.

Title Page 4, Item (56) References Cited, Other Publications, Column 1:
Lines 5 and 22: change "Usa" to -- USA --.

Title Page 5, Item (56) References Cited, Other Publications, Column 2:
Line 50: change "Diclosure" to -- Disclosure --;
Line 64: change "Incluing" to -- Including --; and
Line 70: change "PTO-82" to -- PTO-892 --.

Title Page 6, Item (56) References Cited, Other Publications:
Column 1, line 53: change "Feb. 7" to -- Feb. 17 --; and
Column 2, line 15: change "om" to -- from --.

Signed and Sealed this
Eighteenth Day of March, 2014

Michelle K. Lee
*Deputy Director of the United States Patent and Trademark Office*